US011191773B2

(12) United States Patent
Kahne et al.

(10) Patent No.: US 11,191,773 B2
(45) Date of Patent: Dec. 7, 2021

(54) METHODS OF TREATMENT FOR BACTERIAL INFECTIONS

(71) Applicants: President and Fellows of Harvard College, Cambridge, MA (US); Ohio State Innovation Foundation, Columbus, OH (US)

(72) Inventors: Daniel E. Kahne, Cambridge, MA (US); Michael D. Mandler, Cambridge, MA (US); Vadim Baidin, Cambridge, MA (US); Natividad Ruiz, Columbus, OH (US)

(73) Assignees: President and Fellows of Harvard College, Cambridge, MA (US); The Ohio State University, Columbus, OH (US)

( * ) Notice: Subject to any disclaimer, the term of this patent is extended or adjusted under 35 U.S.C. 154(b) by 0 days.

(21) Appl. No.: 16/631,717

(22) PCT Filed: Jul. 16, 2018

(86) PCT No.: PCT/US2018/042283
§ 371 (c)(1),
(2) Date: Jan. 16, 2020

(87) PCT Pub. No.: WO2019/018286
PCT Pub. Date: Jan. 24, 2019

(65) Prior Publication Data
US 2020/0163985 A1   May 28, 2020

Related U.S. Application Data

(60) Provisional application No. 62/533,554, filed on Jul. 17, 2017.

(51) Int. Cl.
| | |
|---|---|
| *A61K 31/7048* | (2006.01) |
| *A61K 38/12* | (2006.01) |
| *A61K 31/7056* | (2006.01) |
| *A61P 31/04* | (2006.01) |

(52) U.S. Cl.
CPC ...... *A61K 31/7056* (2013.01); *A61K 31/7048* (2013.01); *A61K 38/12* (2013.01); *A61P 31/04* (2018.01)

(58) Field of Classification Search
CPC .. A61K 31/7048; A61K 38/12; C07H 17/075; C07K 7/62
See application file for complete search history.

(56) References Cited

U.S. PATENT DOCUMENTS

| | | | |
|---|---|---|---|
| 4,510,132 A | * 4/1985 | Vaara | C07K 7/62 514/2.4 |
| 8,198,419 B2 | 6/2012 | Thorson | |

(Continued)

FOREIGN PATENT DOCUMENTS

WO    WO-2019/178119 A1    9/2019

OTHER PUBLICATIONS

Kapur et al. Treatment of clinical cases of mastitis with special Formula 17900-Forte. Indian Journal of Veterinary Medicine. 1985, vol. 5, No. 2, p. 107. (Year: 1985).*

(Continued)

*Primary Examiner* — Jeffrey E. Russel
(74) *Attorney, Agent, or Firm* — Foley Hoag LLP

(57) ABSTRACT

This invention features new compositions and methods that are useful in treating a host with a Gram-negative bacterial infection. Combination therapies comprising an aminocoumarin compound and a polymyxin compound are disclosed, including certain combinations that exhibit synergistic effects. Furthermore, aminocoumarin compounds are described having altered inhibition of DNA gyrase in Gram-negative bacteria and/or the ability to target the transport proteins responsible for assembling lipopolysaccharide in the outer membrane of Gram-negative bacteria.

18 Claims, 32 Drawing Sheets

Specification includes a Sequence Listing.

(56) References Cited

U.S. PATENT DOCUMENTS

| | | | |
|---|---|---|---|
| 9,763,996 | B2 | 9/2017 | Vaara et al. |
| 2011/0082098 | A1 | 4/2011 | Calvet et al. |
| 2012/0252745 | A1 | 10/2012 | Blagg et al. |
| 2012/0264924 | A1 | 10/2012 | Thorson |
| 2013/0244230 | A1* | 9/2013 | Luider .................. C12Q 1/02 435/6.1 |
| 2016/0206684 | A1 | 7/2016 | Vaara et al. |
| 2016/0222061 | A1 | 8/2016 | Brown et al. |
| 2016/0289217 | A1 | 10/2016 | Blagg et al. |
| 2017/0000831 | A1* | 1/2017 | Pouillot .................. A61P 31/04 |
| 2021/0009621 | A1 | 1/2021 | Kahne et al. |

OTHER PUBLICATIONS

Loutet et al. Identification of synergists that potentiate the action of polymyxin B against Burkholderia cenocepacia. International Journal of Antimicrobial Agents. 2015, vol. 46, pp. 376-380. (Year: 2015).*

Mandler et al. Novobiocin Enhances Polymyxin Activity by Stimulating Lipopolysaccharide Transport. Journal of the American Chemical Society. May 10, 2018, vol. 140, pp. 6749-6753. (Year: 2018).*

Garneau-Tsodikova et al., "Installation of the pyrrolyl-2-carboxyl pharmacophore by CouN1 and CouN7 in the late biosynthetic steps of the aminocoumarin antibiotics clorobiocin and coumermycin A1," Biochemistry, 45(28):8568-8578 (2006).

International Search Report and Written Opinion for International Application No. PCT/US2018/042283 dated Oct. 17, 2018.

International Search Report and Written Opinion for International Application No. PCT/US2019/021883 dated Jul. 3, 2019.

Invitation to Pay Additional Fees for International Application No. PCT/US2019/021883 mailed April 24, 2019.

May et al., "The antibiotic novobiocin binds and activates the ATPase that powers lipopolysaccharide transport," Journal of the American Chemical Society, 139(48):17221-17224 (2017).

Sherman et al., "Decoupling catalytic activity from biological function of the ATPase that powers lipopolysaccharide transport," PNAS, 111(13):4982-4987 (2014).

Xu et al., "New aminocoumarin antibiotics formed by a combined mutational and chemoenzymatic approach utilizing the carbamoyltransferase NovN," Chemistry and Biology, 11(5):655-662 (2004).

Zhao et al., "Engineering an antibiotic to fight cancer: optimization of the novobiocin scaffold to produce anti-proliferative agents," Journal of Medicinal Chemistry, 54(11):3839-3853 (2011).

* cited by examiner

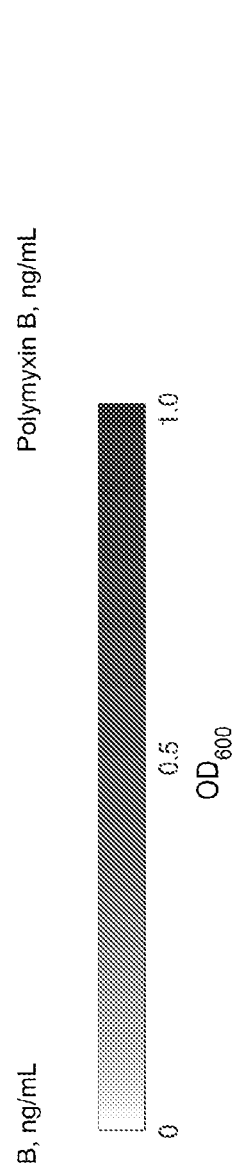

FIG. 2A
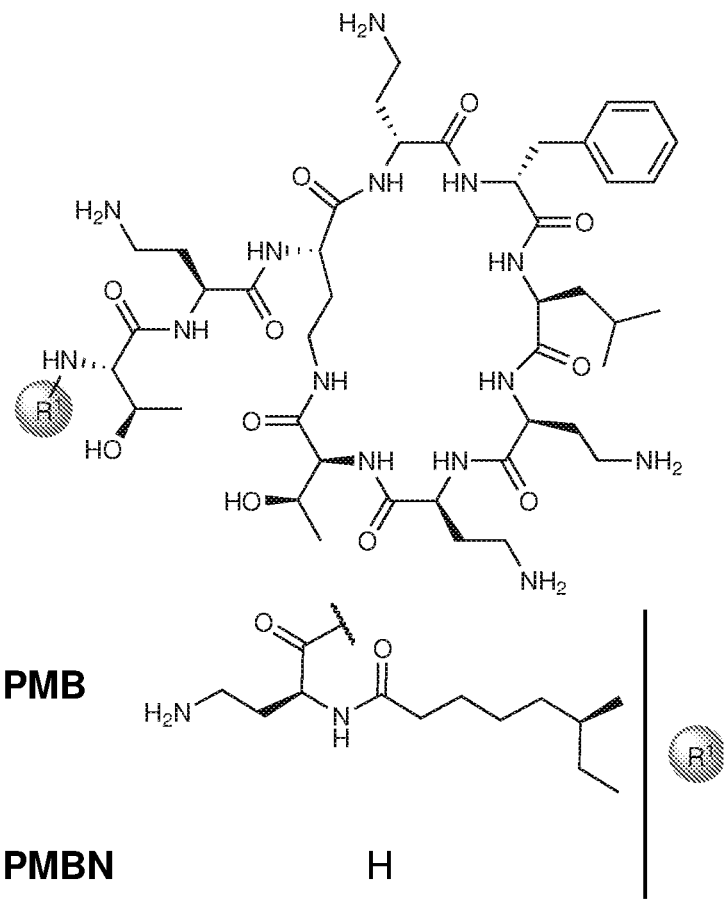
PMB
PMBN     H
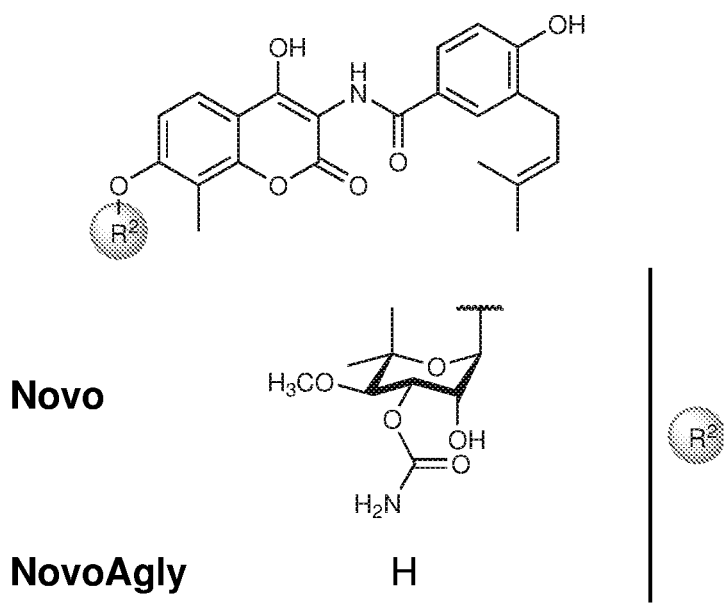
Novo
NovoAgly     H

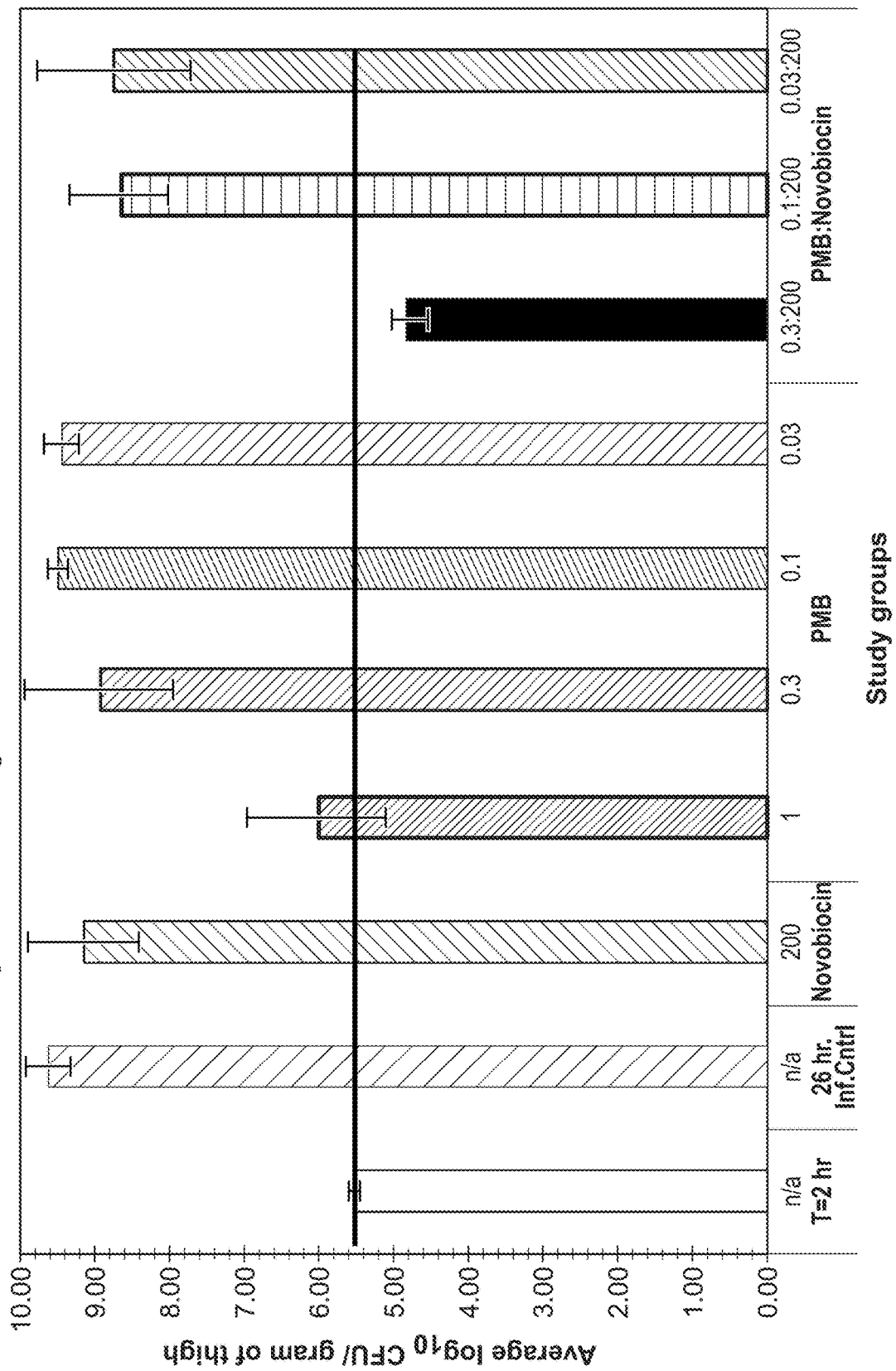

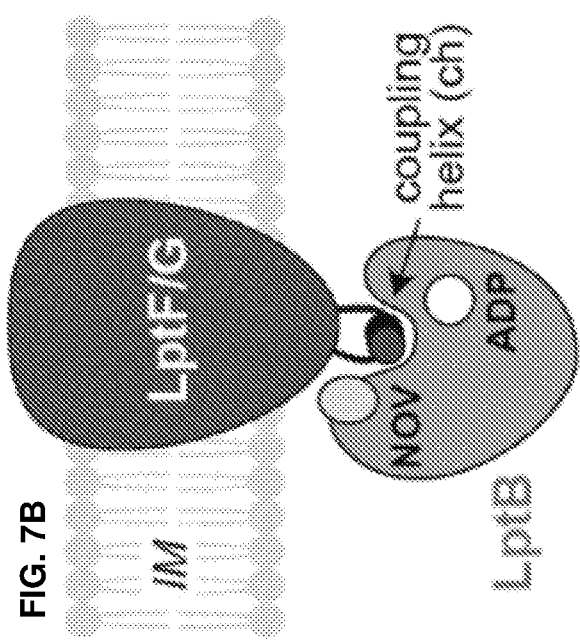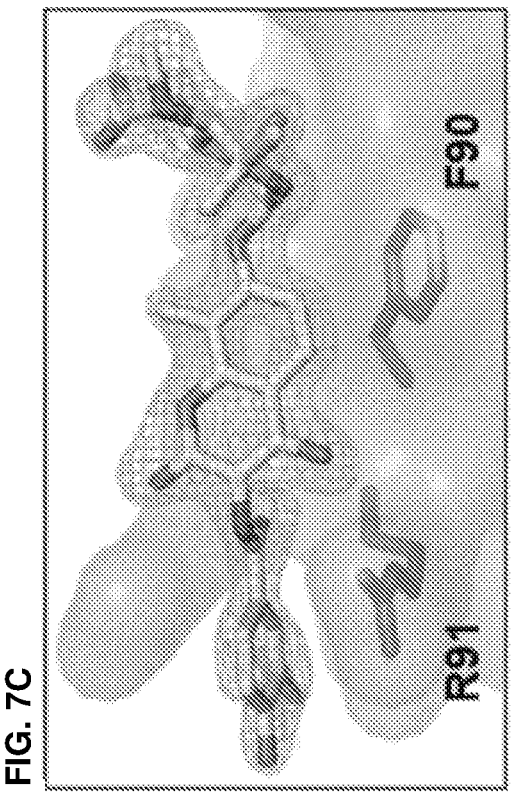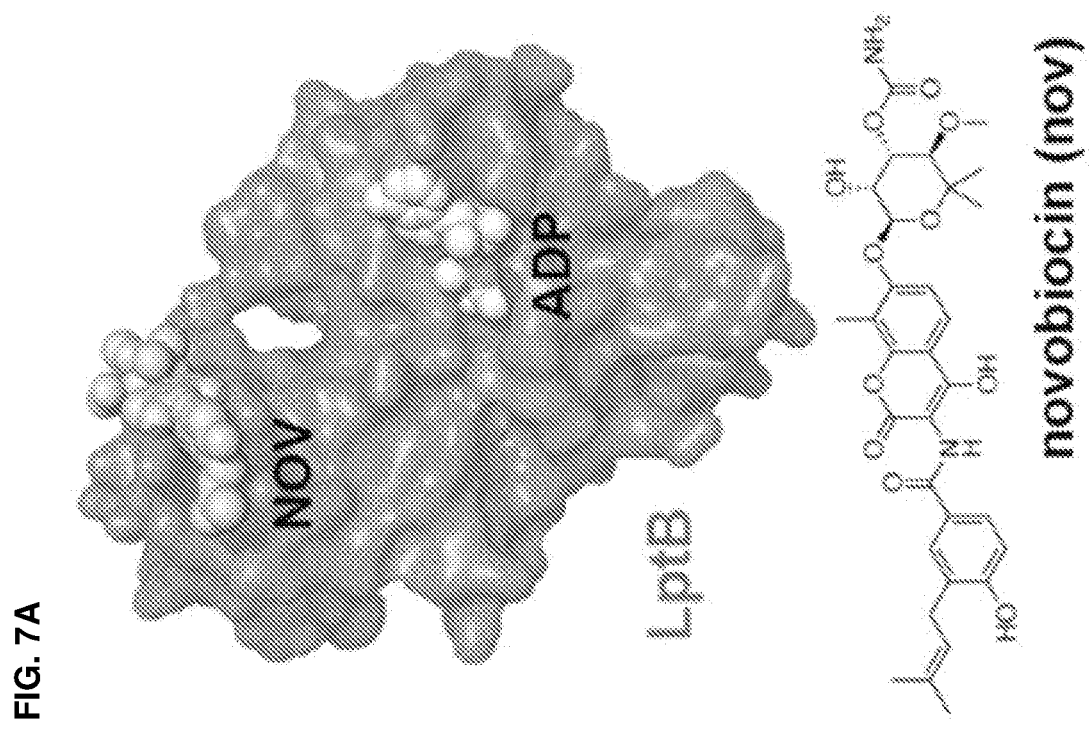
FIG. 7A
FIG. 7B
FIG. 7C

METHODS OF TREATMENT FOR BACTERIAL INFECTIONS

RELATED APPLICATIONS

This application is the U.S. National Stage of International Application No. PCT/US2018/042283, filed Jul. 16, 2018, which designates the U.S., published in English, and claims the benefit of U.S. Provisional Application No. 62/533,554, filed on Jul. 17, 2017.

STATEMENT AS TO FEDERALLY FUNDED RESEARCH

This invention was made with government support under AI109764 awarded by the National Institutes of Health, and DGE-1144152 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy is named HUQ-00625_Sequence_Listing_8919_ST25.txt and is 1492 bytes in size.

BACKGROUND OF THE INVENTION

Gram-negative bacterial pathogens, including *Escherichia coli, Acinetobacter baumannii, Pseudomonas aeruginosa*, and *Klebsiella pneumoniae*, are responsible for more than 35% of the most common hospital-acquired infections. These nosocomial infections can cause severe pneumonia and infections of the urinary tract, site of surgery, and bloodstream, and today, more than 70% of these infections are resistant to at least one of the most commonly used antibiotics. Antibiotic resistance has emerged to all classes of clinically used antibiotics and poses a growing threat to public health. The majority of resistant infections are caused by six problematic pathogens (the so-called ESKAPE pathogens), of which four are Gram-negative (*Pseudomonas aeruginosa, Acinetobacter baumannii, Klebsiella pneumoniae*, and *Enterobacter* species). Thus, there remains a need for new therapies that are effective against Gram-negative bacteria.

SUMMARY OF THE INVENTION

Provided herein are compositions and methods useful in the treatment an individual (e.g., human) having a Gram-negative bacterial infection (e.g., an infection caused by *Escherichia coli, Acinetobacter baumannii, Pseudomonas aeruginosa*, or *Klebsiella pneumoniae*).

In a first aspect, provided herein are methods of treating an individual having a bacterial infection caused by a Gram-negative bacterium. The method includes administering to the individual an effective amount of a pharmaceutical composition including an aminocoumarin compound or salt thereof in combination with a pharmaceutical composition including a polymyxin compound or salt thereof.

In certain embodiments, the Gram-negative bacterium is a polymyxin-resistant bacterium. In further embodiments, the Gram-negative bacterium is a novobiocin-resistant bacterium. In particular embodiments, the Gram-negative bacterium is a novobiocin- and polymyxin-resistant bacterium.

In some embodiments of the methods described herein, the aminocoumarin compound is a novobiocin compound or a salt thereof. In particular embodiments, the novobiocin compound may be descarbamyl novobiocin or a salt thereof, novobiocin-adamantyl or a salt thereof, or novobiocin-aglycone or a salt thereof. In some embodiments, the novobiocin compound exhibits reduced inhibition of DNA gyrase relative to novobiocin. In certain embodiments, the aminocoumarin compound is a novobiocin analog that exhibits same or greater inhibition of DNA gyrase relative to novobiocin. In some embodiments, the novobiocin compound is administered at a dose of about 1 mg/kg/day to about 250 mg/kg/day.

In some embodiments of the methods described herein, the aminocoumarin compound is a clorobiocin compound or a salt thereof. In some embodiments, the clorobiocin compound or salt thereof exhibits reduced inhibition of DNA gyrase relative to clorobiocin. In other embodiments, the aminocoumarin compound is a coumermycin A1 compound or a salt thereof. In some embodiments, the coumermycin A1 compound or salt thereof exhibits reduced inhibition of DNA gyrase relative to coumermycin A1.

In some embodiments of the methods described herein, the aminocoumarin compound (e.g., novobiocin, clorobiocin, or coumermycin, or salt thereof) binds a lipopolysaccharide (LPS) transport (Lpt) protein in the Gram-negative bacterium. In some embodiments, the Lpt protein is LptB.

In any of the methods described herein, the pharmaceutical composition including the aminocoumarin compound or salt thereof may be administered one or more times per day, one or more times week, or one or more times per month. In some embodiments, the pharmaceutical composition including the aminocoumarin compound or salt thereof is administered parenterally, intranasally, orally, or topically.

In some embodiments of the methods described herein, the polymyxin compound is a polymyxin B compound or a salt thereof. In some embodiments, the polymyxin compound is a polymyxin E compound or a salt thereof. In some embodiments, the polymyxin compound or salt thereof, is administered at a dose of about 0.01 mg/kg/day to about 6 mg/kg/day. In some embodiments, the polymyxin compound or salt thereof, is administered at a dose equal to or less than about 1.5 mg/kg/day. In some embodiments, the polymyxin compound or salt thereof, is administered at a dose equal to or less than about 0.5 mg/kg/day. In some embodiments, the polymyxin compound or salt thereof, is administered at a dose equal to or less than about 0.1 mg/kg/day.

In any of the methods described herein, the pharmaceutical composition comprising the polymyxin compound or salt thereof may be administered one or more times per day, one or more times per week, or one or more times per month. In some embodiments, the pharmaceutical composition comprising the polymyxin compound or salt thereof may be administered parenterally, orally, intranasally, or topically.

In any of the methods described herein, the pharmaceutical composition comprising the aminocoumarin compound or salt thereof and/or the polymyxin compound or salt thereof may further comprise a pharmaceutically acceptable excipient.

In some embodiments of the methods described herein, the pharmaceutical composition comprising the aminocoumarin compound and/or the polymyxin compound are administered within one to 60 minutes of each other. In some embodiments, the pharmaceutical composition comprising the aminocoumarin compound and the pharmaceutical composition comprising the polymyxin compound are administered within one to 24 hours of each other. In some embodiments, the pharmaceutical composition comprising the aminocoumarin compound and the pharmaceutical composition comprising the polymyxin compound are administered within one to seven days of each other. In some embodiments, the pharmaceutical composition comprising the aminocoumarin compound and the pharmaceutical composition comprising the polymyxin compound are administered within one to four weeks of each other. In some embodiments, the pharmaceutical composition may be a single pharmaceutical composition comprising the aminocoumarin compound and the polymyxin compound.

In some embodiments of the methods described herein, the individual may be a human. In other embodiments, the individual may be a non-human animal.

In some embodiments of the methods described herein, the bacterial infection is a urinary tract infection, meningeal infection, eye infection, lung infection, or bacteremia. In some embodiments, the bacterial infection is a nosocomial infection.

In some embodiments, the Gram-negative bacterium belongs to (i) a phylum selected from the group consisting of Acidobacteria, Aquificae, Chlamydiae, Bacteroidetes, Chlorobi, Cyanobacteria, Fibrobacteres, Verrucomicrobia, Planctomycetes, and Spirochetes; (ii) a class selected from the group consisting of Alphaproteobacteria, Epsilonproteobacteria, Deltaproteobacteria, and Gammaproteobacteria; or (iii) an order selected from the group consisting of Hydrogenophilales, Methylophilales, Neisseriales, Nitrosomonadales, Procabacteriales, and Rhodocyclales. In some particular embodiments, the Gram-negative bacterium is *Klebsiella pneumoniae, Acinetobacter baumannii, Pseudomonas aeruginosa, Escherichia coli*, or an *Enterobacter* spp. In some embodiments of the methods described herein, the Gram-negative bacterium is a non-opportunistic pathogen.

In any of the methods described herein, the method may be effective to substantially reduce or eliminate the bacterial infection. In some embodiments, the method may further exhibit a decreased level of toxic side effects in the individual relative to monotherapies comprising effective amounts of either the aminocoumarin compound or the polymyxin compound alone.

In another aspect, provided herein are pharmaceutical compositions comprising an aminocoumarin compound or salt thereof. In some embodiments, the aminocoumarin compound or salt thereof may (a) bind a Lpt protein in the Gram-negative bacterium and (b) exhibit decreased inhibition of DNA gyrase relative to the aminocoumarin. In some embodiments, the Lpt protein is LptB.

In a further aspect, provided herein are pharmaceutical compositions comprising an aminocoumarin compound or salt thereof and a polymyxin compound or salt thereof. In some embodiments, the aminocoumarin compound or salt thereof (a) binds a Lpt protein in the Gram-negative bacterium and (b) exhibits decreased inhibition of DNA gyrase relative to the aminocoumarin. In some embodiments, the polymyxin compound may be polymyxin B or a salt thereof. In some embodiments, the polymyxin compound is polymyxin E or a salt thereof. In some embodiments, the Lpt protein is LptB.

In some embodiments of the pharmaceutical compositions provided herein, the aminocoumarin compound may be a novobiocin compound or a salt thereof. In some embodiments, the novobiocin compound is descarbamyl novobiocin or a salt thereof, novobiocin-adamantyl or a salt thereof, or novobiocin-aglycone or a salt thereof.

In some embodiments of the pharmaceutical compositions provided herein, the aminocoumarin compound may be a clorobiocin compound or a salt thereof.

In some embodiments of the pharmaceutical compositions provided herein, the aminocoumarin compound may be a coumermycin A1 compound or a salt thereof.

In any of the pharmaceutical compositions provided herein, the pharmaceutical composition may further comprise a pharmaceutically acceptable excipient. In some embodiments, the pharmaceutical composition may be in unit-dose form. In some embodiments, the pharmaceutical composition may be formulated for parenteral administration, intranasal administration, topical administration, or oral administration. In some embodiments, the pharmaceutical composition is formulated for intramuscular administration, intravenous administration, intrathecal administration, or ophthalmic administration.

In a further aspect, provided herein is a method of treating an individual having a bacterial infection caused by a Gram-negative bacterium, the method including administering to the individual any of the above pharmaceutical compositions, wherein the pharmaceutical composition is administered as a monotherapy.

Additionally, provided herein are kits useful in the treatment of an individual having a bacterial infection caused by a Gram-negative bacterium.

In some embodiments, the kit includes (i) a composition comprising an aminocoumarin compound or salt thereof; (ii) a composition comprising a polymyxin compound; and (iii) instructions for administrating the aminocoumarin compound or salt thereof and the polymyxin compound or salt thereof to an individual having a bacterial infection, wherein the bacterial infection is caused by a Gram-negative bacterium.

In some embodiments, the kit includes (i) a composition comprising an aminocoumarin compound or salt thereof; and (ii) instructions for administrating the aminocoumarin compound or salt thereof and a polymyxin compound or salt thereof to an individual having a bacterial infection, wherein the bacterial infection is caused by a Gram-negative bacterium.

In some embodiments, the kit includes (i) a composition comprising a polymyxin compound or salt thereof; and (ii) instructions for administrating the polymyxin compound or salt thereof and an aminocoumarin compound or salt thereof to an individual having a bacterial infection, wherein the bacterial infection is caused by a Gram-negative bacterium.

In some embodiments of the kits described herein, the aminocoumarin compound may be a novobiocin compound or a salt thereof. In some embodiments, the novobiocin compound is descarbamyl novobiocin or a salt thereof, novobiocin-adamantyl or a salt thereof, or novobiocin-aglycone or a salt thereof. In some embodiments, the aminocoumarin compound is clorobiocin compound or a salt thereof. In some embodiments, the aminocoumarin compound is a coumermycin A1 compound.

In some embodiments of the kits described herein, the polymyxin compound is polymyxin B or a salt thereof. In some embodiments, the polymyxin compound is polymyxin E or a salt thereof.

In some embodiments of the kits described herein, the Gram-negative bacterium is a non-opportunistic pathogen. In some embodiments, the Gram-negative bacterium belongs to (i) a phylum selected from the group consisting of Acidobacteria, Aquificae, Chlamydiae, Bacteroidetes, Chlorobi, Cyanobacteria, Fibrobacteres, Verrucomicrobia, Planctomycetes, and Spirochetes; (ii) a class selected from the group consisting of Alphaproteobacteria, Epsilonproteobacteria, Deltaproteobacteria, and Gammaproteobacteria; or (iii) an order selected from the group consisting of Hydrogenophilales, Methylophilales, Neisseriales, Nitrosomonadales, Procabacteriales, and Rhodocyclales. In some embodiments, the Gram-negative bacterium is *Klebsiella pneumoniae*, *Acinetobacter baumannii*, *Pseudomonas aeruginosa*, *Escherichia coli*, or an *Enterobacter* spp. In some embodiments, the bacterial infection is a urinary tract infection, meningeal infection, eye infection, lung infection, or bacteremia. In some embodiments, the bacterial infection is a nosocomial infection.

Definitions

The term "aminocoumarin compound," as used herein, refers to compounds and salts thereof including novobiocin, coumermycin A1, clorobiocin, novobiocin aglycone, descarbamyl novobiocin, 1-adamantyl novobiocin, novobiocin sodium, fluorobiocin, and any compounds, prodrugs, or analogs with structural similarity to these compounds. Aminocoumarin compounds also include molecules having similar structures and antibacterial properties and that function with a similar mechanism as any of the compounds listed above. Aminocoumarin compounds include those described in U.S. Pat. Nos. 9,120,774, 8,618,269, 8,212,012, 8,212,011, 7,960,353, 7,811,998, 7,622,451, 7,608,594, 4,169,940, and 4,147,704, and US Publication Nos. 20120264924, 20120252745, 20110082098, 20100105630, 20100048882, 20090187014, 20090163709, 20070270452, and 20060199776. Aminocoumarin compounds also include molecules having similar structures and antibacterial properties and that function with a similar mechanism as any of the compounds listed above.

The term "polymyxin compound," as used herein, refers to antibiotic compounds and salts thereof including polymyxin A, polymyxin B, polymyxin C, polymyxin D, and polymyxin E (also known as colistin), and any compounds, prodrugs, or analogs with structural similarity to these compounds. Polymyxin compounds include those described in U.S. Pat. Nos. 9,096,649, 9,090,669, 9,067,974, 8,680,234, 8,642,535, 8,329,645, 8,193,148, 7,807,637, 7,507,718, 6,579,696, 6,380,356, and 5,177,059, and US Publication Nos. 20170137469, 20170073373, 20160287661, 20160206684, 20140162937, 20140142030, 20140134669, 20120316105, 20120283176, 20100292136, 20100279347, 20090215677, 20090203881, and 20080281684. Polymyxin compounds also include molecules having similar structures and antibacterial properties and that function with a similar mechanism as any of the compounds listed above. Polymyxin compounds do not include polymyxin B nonapeptide.

The term "bacterial infection," as used herein, refers to the invasion of an individual's cells, tissues, and/or organs by bacteria (e.g., *Escherichia coli*, *Acinetobacter baumannii*, *Pseudomonas aeruginosa*, or *Klebsiella pneumoniae*), thus, causing an infection. In some embodiments, the bacteria may grow, multiply, and/or produce toxins in the individual's cells, tissues, and/or organs. In some embodiments, a bacterial infection can be any situation in which the presence of a bacteria population(s) is latent within or damaging to a host body. Thus, an individual is "suffering" from a bacterial infection when a latent bacterial population is detectable in or on the individual's body, an excessive amount of a bacterial population is present in or on the individual's body, or when the presence of a bacterial population(s) is damaging to the cells, tissues, and/or organs of the individual.

The term "protecting against a bacterial infection" or "preventing a bacterial infection" as used herein, refers to preventing an individual from developing a bacterial infection or decreasing the risk that an individual may develop a bacterial infection (e.g., a bacterial infection caused by *Escherichia coli*, *Acinetobacter baumannii*, *Pseudomonas aeruginosa*, or *Klebsiella pneumoniae*). Prophylactic drugs used in methods of protecting against a bacterial infection in an individual are often administered to the individual prior to any detection of the bacterial infection. In some embodiments of methods of protecting against a bacterial infection, an individual (e.g., an individual at risk of developing a bacterial infection) may be administered a pharmaceutical composition of the invention to prevent the bacterial infection development or decrease the risk of the bacterial infection development.

The term "treating" or "to treat," as used herein, refers to a therapeutic treatment of a bacterial infection in an individual. In some embodiments, a therapeutic treatment may slow the progression of the bacterial infection, improve the individual's outcome, and/or eliminate the infection. In some embodiments, a therapeutic treatment of a bacterial infection in an individual may alleviate or ameliorate of one or more symptoms or conditions associated with the bacterial infection, diminish the extent of the bacterial infection, stabilize (i.e., not worsening) the state of the bacterial infection, prevent the spread of the bacterial infection, and/or delay or slow the progress of the bacterial infection, as compared to the state and/or the condition of the bacterial infection in the absence of therapeutic treatment.

The term "effective amount," as used herein, is meant the amount of drug (e.g., an aminocoumarin compound or salt thereof and/or a polymyxin compound or salt thereof) required to treat or prevent a bacterial infection or a disease associated with a bacterial infection. The effective amount of drug used to practice the methods described herein for therapeutic or prophylactic treatment of conditions caused by or contributed to by a bacterial infection varies depending upon the manner of administration, the age, body weight, and general health of the individual. Ultimately, the attending physician will decide the appropriate amount and dosage regimen. Such amount is referred to as an "effective amount."

The term "salt," as used herein, refers to any pharmaceutically acceptable salt, such as a non-toxic acid addition salt, metal salt, or metal complex, commonly used in the pharmaceutical industry. Examples of acid addition salts include organic acids, such as acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxaloacetic, oxalosuccinic, propionic, pyruvic, ascorbic, succinic, benzoic, palmitic, suberic, salicylic, tartaric, methanesulfonic, toluenesulfonic, and trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

The term "pharmaceutically acceptable," as used herein, refers to those compounds, materials, compositions, and/or dosage forms, which are suitable for contact with the tissues of an individual (e.g., a human), without excessive toxicity, irritation, allergic response and other problem complications commensurate with a reasonable benefit/risk ratio.

The term "pharmaceutical composition," as used herein, refers to a mixture containing a therapeutic compound to be administered to an individual (e.g., a human), in order to prevent, treat or control a particular disease or condition affecting the individual, such as bacterial infection, among others, e.g., as described herein.

The term "excipient," as used herein refers to a substance formulated alongside the active ingredient of a medication. They may be included, for example, for the purpose of long-term stabilization, or to confer a therapeutic enhancement on the active ingredient in the final dosage form.

The term "monotherapy," as used herein, refers to a treatment of a disease with one drug.

The term "combination therapy," as used herein, refers to a treatment of a disease with two or more drugs.

The term "between," as used herein, refers to any quantity within the range indicated and enclosing each of the ends of the range indicated.

Other than in the operating examples, or where otherwise indicated, all numbers expressing quantities of ingredients, concentrations, or reaction conditions used herein should be understood as modified in all instances by the term "about."

The term "about," as used herein, indicates a deviation of ±10%. For example, about 10% refers to from 9% to 11%.

BRIEF DESCRIPTION OF THE DRAWINGS

FIGS. 1A-1F are a set of graphs of checkerboard microdilution assays between polymyxin B and novobiocin in wild-type strains (unless otherwise noted) grown at 37° C. for 24 h, showing that novobiocin synergizes with polymyxin B to kill Gram-negative pathogens in vitro. Checkerboard data are representative of at least three biological replicates. FIG. 1A is a graph of wild-type Escherichia coli, ATCC 15692; FIG. 1B is a graph of wild-type Enterobacter cloacae, ATCC 13047; FIG. 1C is a graph of wild-type Klebsiella pneumoniae, ATCC 700721; FIG. 1D is a graph of wild-type Pseudomonas aeruginosa, ATCC 15692 (PAO1); FIG. 1E is a graph of wild-type Acinetobacter baumannii, ATCC 19606; FIG. 1F is a graph of novobiocin-resistant Acinetobacter baumannii, ATCC 19606 gyrB (R150C).

FIGS. 2A-2G are a set of structures, graphs, and gels of a checkerboard microdilution assays showing that polymyxin B nonapeptide (PMBN) potentiates the gyrase inhibitor novobiocin (Novo), while having no effect on the gyrase-inactive novobiocin aglycone (NovoAgly). FIG. 2A is a drawing of the structures of PMB, PMBN, novobiocin (Novo), and novobiocin aglycone (NovoAgly). FIG. 2B is a checkerboard assay showing wild-type A. baumannii exhibits synergy between PMBN and novobiocin. FIG. 2C is a checkerboard assay showing novobiocin-resistant A. baumannii exhibits this same synergy but at higher [novobiocin]. FIG. 2D is a checkerboard assay showing novobiocin aglycone does not synergize with PMBN in wild-type A. baumannii (and novobiocin-resistant A. baumannii 19606 gyrB(R150C) point mutant (Novo$^R$), which has 300-fold resistance towards novobiocin; data not shown).

FIG. 2E is a checkerboard assay showing novobiocin aglycone synergizes with PMB in wild-type A. baumannii. FIG. 2F is a checkerboard assay showing novobiocin aglycone synergizes with PMB in Novo$^R$ A. baumannii. FIG. 2G is a gel showing supercoiling assays that show that novobiocin aglycone has at least 70× reduced activity against A. baumannii and at least 100× reduced activity against E. coli gyrase.

FIG. 3A is a growth curve of Klebsiella pneumoniae. FIG. 3B is a growth curve of Acinetobacter baumannii Novo$^R$. FIG. 3C is a plot of CFU/ml over time of Pseudomonas aeruginosa. FIG. 3D is a growth curve of Escherichia coli.

FIG. 4 is a graph showing in vivo data of mice infected with E. coli and then treated with novobiocin, polymyxin B, or a combination of the two.

FIG. 7A is a surface representation of the structure of an LptB monomer bound to one molecule of novobiocin and one molecule of ADP.

FIG. 7B is a schematic drawing showing the orientation of the novobiocin-binding site relative to the groove in LptB that accommodates the coupling helices from LptFG.

FIG. 7C is a surface representation showing novobiocin contacts LptB at residues F90 and R91, previously shown to interact with LptFG. The Fo-Fc omit map is contoured at 3σ.

DETAILED DESCRIPTION

Figure 10:
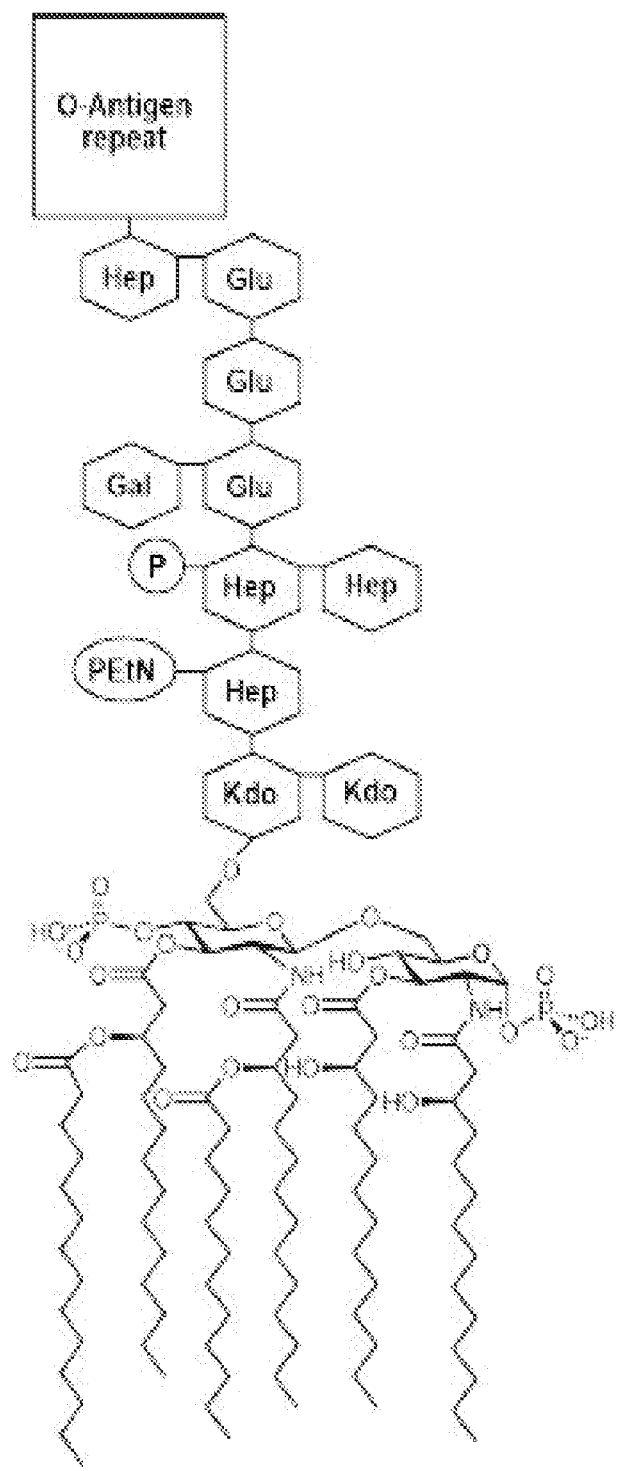
FIG. 10 is a schematic drawing of the structure of *E. coli* lipopolysaccharide. Kdo=3-deoxy-D-manno-oct-2-ulosonic acid, Hep=L-glycero-D-manno-heptose, PEtN=phosphoethanolamine, P=phosphate, Glu=D-glucose, Gal=D-galactose.

The invention provides novel methods and compositions for treating an individual having a bacterial infection caused by Gram-negative bacteria. Gram-negative bacteria are naturally resistant to many antibiotics due to the presence of the outer membrane, a unique asymmetric bilayer with phospholipids in the inner leaflet and lipopolysaccharide (LPS) in the outer leaflet. LPS is a large glycolipid containing multiple fatty acyl chains that comprise the hydrophobic region of the outer leaflet. Phosphate groups attached to the core sugars bind divalent metal cations to form a well-ordered polyelectrolyte barrier (FIG. 10). Many anti-bacterial agents are unable to penetrate this barrier, and many of those agents that somehow cross the barrier are immediately exported by multi-drug efflux pumps.

The present invention is based, in part, on the discovery that aminocoumarin compounds (e.g., novobiocin or analogs thereof) administered in combination with polymyxin compounds have a powerful synergistic bactericidal effect against Gram-negative bacteria in vitro and in vivo. Based on the synergistic effect achieved when the compounds are administered in combination, an effective dosage of the aminocoumarin compound and/or the polymyxin compound in the combination therapies provided herein is reduced relative to dosage regimens based on either drug alone. By creating a broader therapeutic window, the methods provided herein reduce or eliminate the risk of toxic side effects in patients and reduce the risk of antibacterial resistance associated with the higher dosages required in treatment regimens based on aminocoumarin compounds or polymyxin compounds alone. Moreover, aminocoumarin compounds (e.g., novobiocin) and polymyxin compounds may synergistically act to kill polymyxin- and/or novobiocin-resistant, gram-negative bacteria.

Gram-negative organisms contain DNA gyrase, which is inhibited by certain aminocoumarins, such as novobiocin. Novobiocin activity against these organisms is limited, however, by a combination of poor penetration and efflux. In a related aspect, the invention is further based on the discovery that some aminocoumarin compounds (e.g., novobiocin) can not only target DNA gyrase but, in some instances, can additionally or alternatively bind a different target in Gram-negative bacteria: the transport machine responsible for assembling LPS in the outer membrane. For example, novobiocin compounds provided herein can bind to the conserved ATPase that powers LPS transport. Aminocoumarin compounds that can bind Lpt proteins may have advantageous activity against Gram-negative bacteria. However, other aminocoumarin compounds described herein exhibit reduced ability to bind or inhibit DNA gyrase yet still produce an antibiotic effect.

The synthesis of LPS is completed at the inner membrane and from there LPS must be transported to the cell surface. This transport requires a machine because it is highly unfavorable to extract a molecule containing as many as six long hydrocarbon chains from a membrane. *E. coli* contains seven essential LPS transport (Lpt) proteins, Lpt-ABCDEFG, which are proposed to form a trans-envelope complex (FIG. 6A). LptB$_2$FG comprise an ABC system with a homodimer of cytoplasmic ATPases complexed to a transmembrane heterodimer. ATP hydrolysis by LptB is required for LPS extraction from the inner membrane and transport through the periplasm. LptC receives LPS from an inner membrane component of the ABC system and passes it to LptA for transit across the periplasm to the outer membrane translocon, LptDE.

Gram-Negative Bacteria

Gram-negative bacteria are a group of bacteria characterized by their cell envelopes, which are composed of a thin peptidoglycan cell wall sandwiched between and inner cytoplasmic cell membrane and a bacterial outer membrane. The outer membrane contains LPS, which consist of lipid A, a core polysaccharide, and O antigen in its outer leaflet and phospholipids in its inner leaflet.

The compositions and methods of this invention may be used to treat any Gram-negative bacteria. Exemplary Gram-negative bacteria are the proteobacteria such as *Escherichia coli*, *Salmonella*, *Shigella*, and other Enterobacteriaceae, *Pseudomonas*, *Moraxella*, *Helicobacter*, Stenotrophomas, *Bdellovibrio*, and *Legionella*. Other medically relevant Gram-negative bacteria include *Neisseria gonorrhoeae*, *Neisseria meningitides*, *Moraxella catarrhalis*, *Haemophilus influenzae*, *Klebsiella pneumoniae*, *Legionella pneumophila*, *Pseudomonas aeruginosa*, *Proteus mirabilis*, *Enterobacter cloacae*, *Serratia marcescens*, *Helicobacter pylori*, *Salmonella enteritidis*, *Salmonella typhi*, *Burkholderia cenocepacia*, and *Acinetobacter baumannii*.

Certain bacteria that may be treated with this invention include bacteria from the phyla including Acidobacteria, Aquificae, Chlamydiae, Bacteroidetes, Chlorobi, Cyanobacteria, Fibrobacteres, Verrucomicrobia, Planctomycetes, and Spirochetes, or the classes including Alphaproteobacteria, Epsilonproteobacteria, Deltaproteobacteria, and Gammaproteobacteria, or the orders including Hydrogenophilales, Methylophilales, Neisseriales, Nitrosomonadales, Procabacteriales, and Rhodocyclales, or the genus and species of *Klebsiella pneumoniae*, *Acinetobacter baumannii*, *Pseudomonas aeruginosa*, *Escherichia coli*, or an *Enterobacter* spp.

Indications

Gram-negative bacteria infections can be community acquired or hospital acquired. They can lead to a number of different types of infections in humans, including infection of the skin and soft tissue, urinary tract infection, bloodstream infection, or meningeal infection, eye infection, lung infection, or any other bacteremia. The methods and compositions of this invention may be used to treat or prevent any of these types of infections or at least substantially reduce the infection. In some instances, the Gram-negative bacteria may be either an opportunistic pathogen or a non-opportunistic pathogen. An opportunistic pathogen infects an individual who is immunocompromised.

Aminocoumarins and Analogs Thereof

Aminocoumarin compounds are a class of antibiotics including novobiocin, clorobiocin, and coumermycin A1, the structures of which are shown below. Aminocoumarin compounds may bind a LPS transport (Lpt) protein (e.g., LptB) in Gram-negative bacteria.

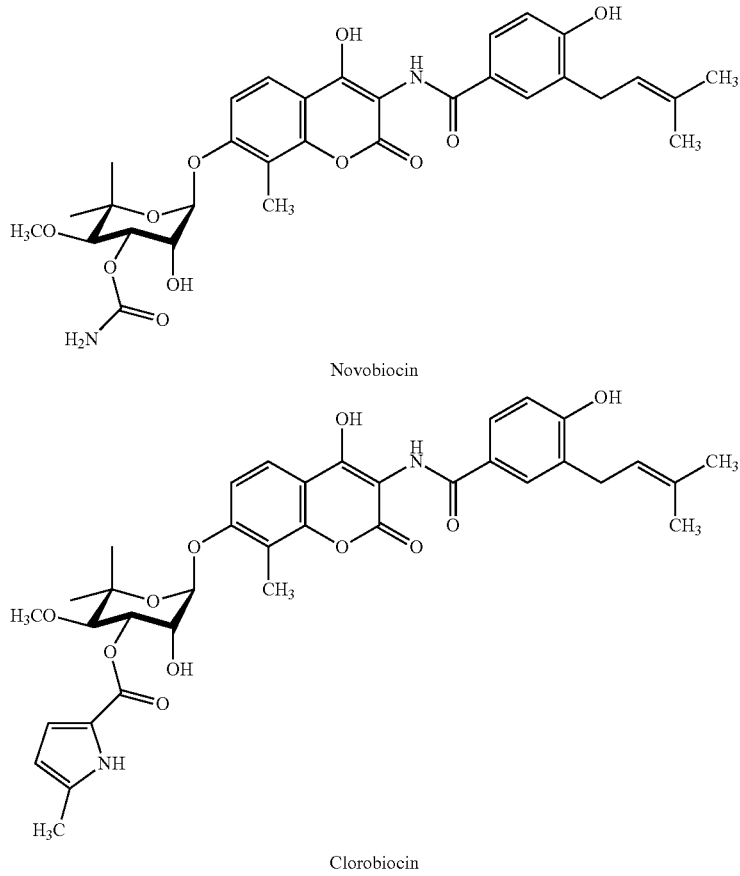

Novobiocin

Clorobiocin

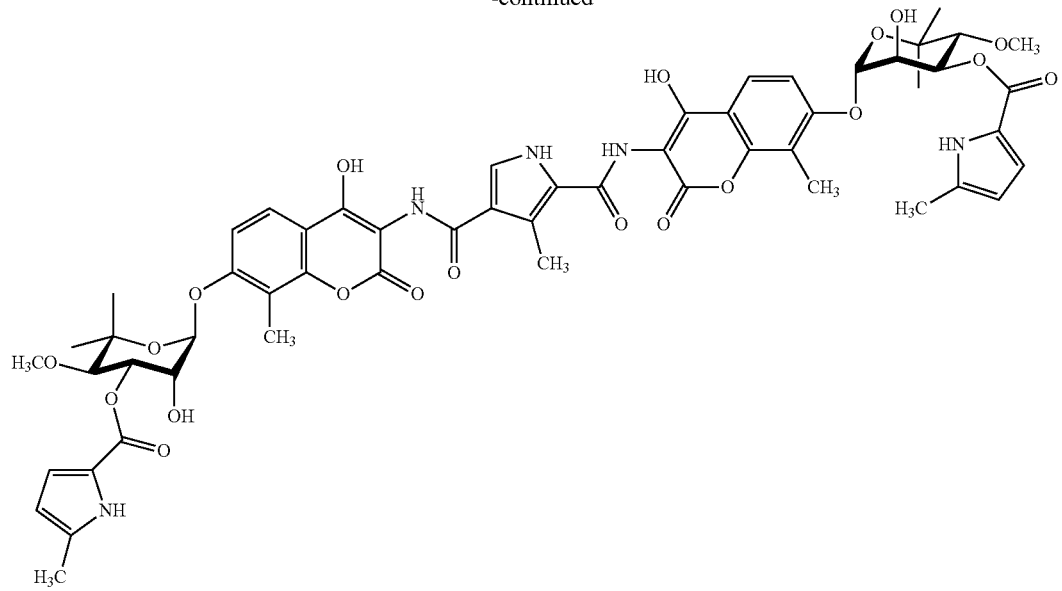

Coumermycin A1

Novobiocin, also known as albamycin or cathomycin, is an antibiotic naturally produced by the Actinobacterium *S. niveus*. Novobiocin is an inhibitor of DNA gyrase and may function by targeting the GyrB subunit of the enzyme by acting as a competitive inhibitor of ATP. The structure of novobiocin includes three components: a benzoic acid derivative, a coumarin residue, and a sugar noviose. In some instances, novobiocin compounds may be in salt form (e.g., novobiocin sodium). The novobiocin compound may be modified by adding or removing substituents from the molecule. For example, novobiocin compounds are disclosed in which the coumarin substituents are varied. Exemplary salts and compounds are novobiocin sodium (Novo), descarbamyl novobiocin (Desc), and novobiocin aglycone (NovoAgly), 1-adamantyl-novobiocin (adn), and fluorobiocin (fbn), the structures of which are shown below. While novobiocin has the ability to inhibit DNA gyrase, some novobiocin compounds exhibit either increased, reduced, or substantially the same ability to inhibit DNA gyrase. DNA gyrase inhibition properties may be compared relative to any other aminocoumarin compound.

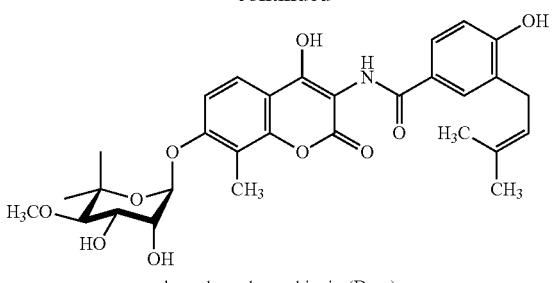

descarbamyl novobiocin (Desc)

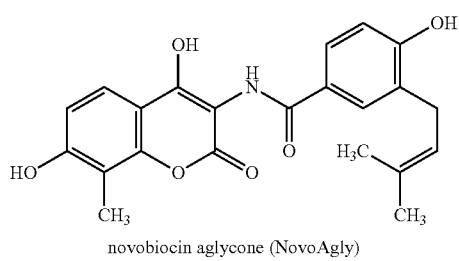

novobiocin aglycone (NovoAgly)

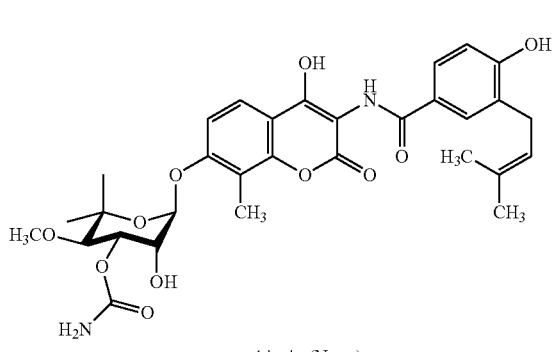

novobiocin (Novo)

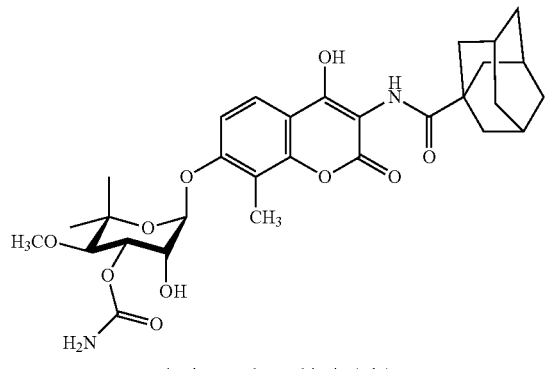

1-adamantyl-novobiocin (adn)

-continued

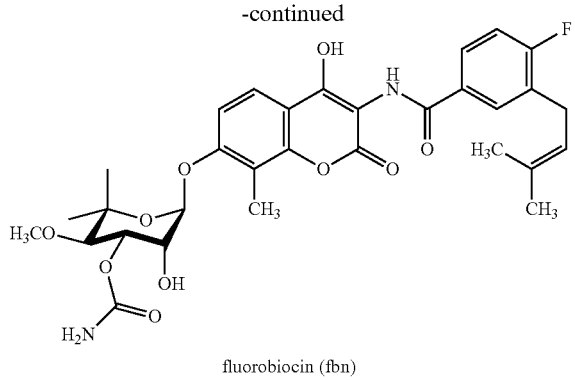

fluorobiocin (fbn)

Aminocoumarin compounds have been described in the art, such as those described in U.S. Pat. Nos. 9,120,774, 8,618,269, 8,212,012, 8,212,011, 7,960,353, 7,811,998, 7,622,451, 7,608,594, 4,169,940, 4,147,704, and US Publication Nos. 20120264924, 20120252745, 20110082098, 20100105630, 20100048882, 20090187014, 20090163709, 20070270452, and 20060199776, the disclosures of each of which are herein incorporated by reference as they pertain to novobiocin compounds and salts thereof. Further, the identification and isolation of clorobiocin has previously been described in the art, e.g., U.S. Pat. Nos. 3,682,886 and 3,793,147, the disclosures of each of which are herein incorporated by reference.

Polymyxin Compounds

Polymyxin compounds are antibiotics such as those that are naturally produced by Gram-positive bacteria such as *P. polymyxa*. Polymyxins may be useful in the treatment of Gram-negative bacterial infections and function by disruption of the bacterial cell membrane. They are often neurotoxic and nephrotoxic, so they are commonly used as a last resort of antibiotics if other treatments are ineffective, such as in the case of multi-drug resistant infections. Polymyxins include both polymyxin B, and polymyxin E (also known as colistin), the structures of which are shown below. Other naturally-occurring polymyxins are polymyxin A, polymyxin C, and polymyxin D.

Polymyxin B

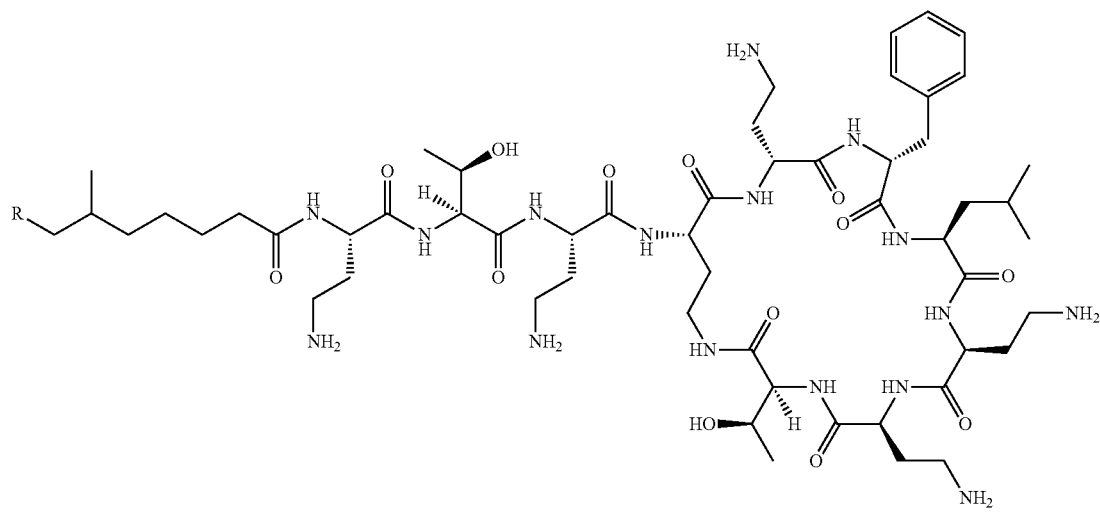

Polymyxin E

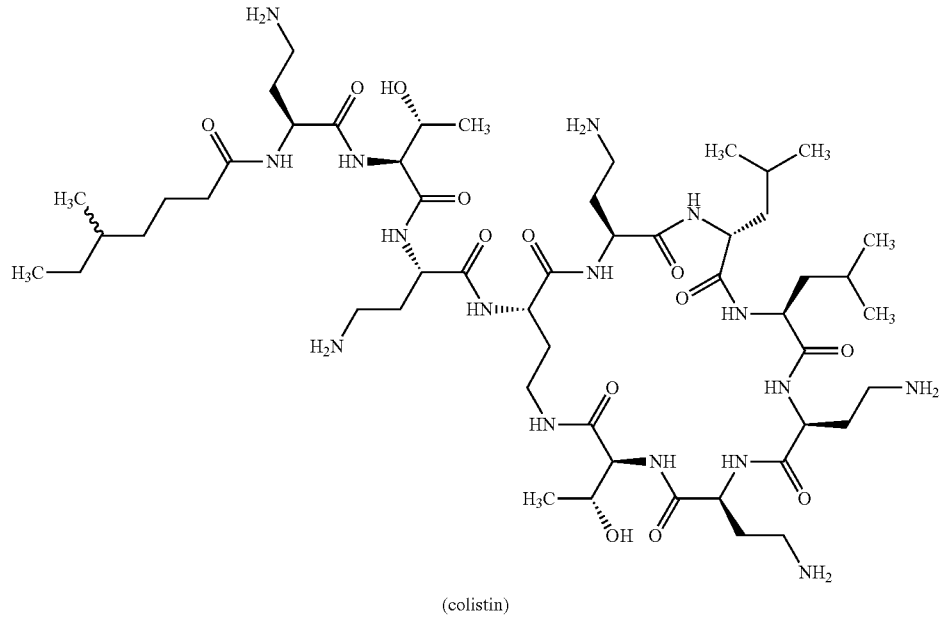

(colistin)

Polymyxins may be in a salt form (e.g., colistin sulfate, colistin methanesulfonate sodium, colistin sulfomethate sodium). Polymyxin B may be any of polymyxin B1, B1-I, B2, B3, or B6, or a mixture thereof.

Polymyxin compounds have been described in the art, such as in U.S. Pat. Nos. 9,096,649, 9,090,669, 9,067,974, 8,680,234, 8,642,535, 8,329,645, 8,193,148, 7,807,637, 7,507,718, 6,579,696, 6,380,356, and 5,177,059, and US Publication Nos. 20170137469, 20170073373, 20160287661, 20160206684, 20140162937, 20140142030, 20140134669, 20120316105, 20120283176, 20100292136, 20100279347, 20090215677, 20090203881, and 20080281684, the disclosures of each of which are herein incorporated by reference as they pertain to polymyxin molecules and derivatives thereof.

Methods of Treatment

Formulations and Carriers

This invention describes methods of treatment for bacterial infections by administering a pharmaceutical composition. The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types).

A pharmaceutical composition is typically formulated to be compatible with its intended route of administration. For oral administration, agents can be formulated by combining the active compounds with pharmaceutically acceptable carriers well known in the art. Such carriers enable the compounds of the invention to be formulated as a powder, tablet, pill, capsule, lozenge, liquid, gel, syrup, slurry, suspension, and the like. It is recognized that some pharmaceutical compositions, if administered orally, must be protected from digestion. This is typically accomplished either by complexing the protein with a composition to render it resistant to acidic and enzymatic hydrolysis or by packaging the protein in an appropriately resistant carrier such as a liposome. Suitable excipients for oral dosage forms include, for example, fillers such as sugars, including lactose, sucrose, mannitol, or sorbitol; cellulose preparations such as, for example, starch, gelatin, gum tragacanth, methyl cellulose, hydroxypropylmethyl cellulose, sodium carboxymethylcellulose, and/or polyvinylpyrrolidone (PVP). Disintegrating agents may be added, for example, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

For topical application, a pharmaceutical composition may be formulated in a suitable ointment, lotion, gel, or cream containing the active components suspended or dissolved in one or more pharmaceutically acceptable carriers suitable for use in such compositions.

Dosage and Administration

The pharmaceutical compositions used in this invention can be administered to an individual (e.g., patient) in a variety of ways. The compositions must be suitable for the individual receiving the treatment and the mode of administration. Furthermore, the severity of the infection to be treated affects the dosages and routes. The pharmaceutical compositions used in this invention can be administered orally, sublingually, parenterally, intravenously, subcutaneously, intramedullary, intranasally, as a suppository, using a flash formulation, topically, intradermally, subcutaneously, via pulmonary delivery, via intra-arterial injection, ophthalmically, optically, intrathecally, or via a mucosal route.

In general, the dosage of a pharmaceutical composition or the active agent in a pharmaceutical composition may be in the range of from about 1 pg to about 1 kg (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g, e.g., 10 g-100 g, e.g., 20 g, 30 g, 40 g, 50 g, 60 g, 70 g, 80 g, 90 g, 100 g, e.g., 100 g-1 kg, e.g., 200 g, 300 g, 400 g, 500 g, 600 g, 700 g, 800 g, 900 g, 1 kg).

The dose may also be administered as in a unit dose form or as a dose per mass or weight of the patient from about 0.01 mg/kg to about 1000 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg, e.g., 100-1000 mg/kg, e.g., 200 mg/kg, 300 mg/kg, 400 mg/kg, 500 mg/kg, 600 mg/kg, 700 mg/kg, 800 mg/kg, 900 mg/kg, 1000 mg/kg). The dose may also be administered as a dose per mass or weight of the patient per unit day (e.g., 0.1-10 mg/kg/day).

The dosage regimen may be determined by the clinical indication being addressed, as well as by various patient variables (e.g., weight, age, sex) and clinical presentation (e.g., extent or severity of disease). Furthermore, it is understood that all dosages may be continuously given or divided into dosages given per a given time frame. The composition can be administered, for example, every hour, day, week, month, or year.

The compositions of this invention may be prepared into a kit. For example, the kit may contain a composition (e.g., comprising an aminocoumarin compound and/or a polymyxin compound) and instructions for administering the composition (e.g., the aminocoumarin compound and/or the polymyxin compound) to treat a bacterial infection.

Combination Therapies

As the methods of the invention described herein include treating or preventing bacterial infections, it may be useful to design combination therapies comprising two or more pharmaceutical agents (e.g., an aminocoumarin or salt thereof, and a polymyxin compound or salt thereof). The two or more agents may be administered sequentially, or at substantially the same time. For example, the second agent may be administered about 1 minute, 1 hour, 1 day, or 1 week after the first agent. The two or more agents may be administered in the same formulation or as separate formulations.

The combination therapies of the invention may be useful in providing synergistic effects of the two or more pharmaceutical agents. For example, the minimum inhibitory concentration (MIC) or minimum bactericidal concentration (MBC) of a certain drug may be lowered upon administration with a second agent. Additionally, the cumulative treatment effect of two drugs in combination may be greater than the sum of the treatment effects of each individual drug. This behavior may be beneficial by lowering the amount of drug required to treat certain indications. When a drug exhibits toxicity, it is preferable to use the lowest dosage possible to achieve a treatment effect in order to minimize detrimental side effects while still maintaining efficacy. In some embodiments, the effects of the combination therapy will be synergistic but the side effects will not.

EXAMPLES

Example 1. Synergy of Novobiocin Compounds and Polymyxin Compounds

Checkerboard microdilution assays between polymyxin B and novobiocin were performed in wild-type strains (unless otherwise noted) grown at 37° C. for 24 h. Checkerboard data (FIG. 1A-1F) are representative of at least three biological replicates. The following strains were tested: A) Wild-type *Escherichia coli*, ATCC 25922; B) Wild-type *Enterobacter cloacae*; ATCC 13047) Wild-type *Klebsiella pneumoniae*, ATCC 700721; D) Wild-type *Pseudomonas aeruginosa*, ATCC 15692 (PAO1); E) Wild-type *Acinetobacter baumannii*, ATCC 19606; F) novobiocin-resistant *Acinetobacter baumannii*, ATCC 19606 gyrB(R150C). The data indicate that novobiocin synergizes with polymyxin B to kill Gram-negative pathogens in vitro. Table 1 below shows the minimal inhibitory concentrations (MIC) of polymyxin B and novobiocin.

TABLE 1

MIC inhibitory concentrations of polymyxin B and novobiocin.

|  | Polymyxin B (ng/mL) | Novobiocin (µg/mL) |
| --- | --- | --- |
| *Klebsiella pneumoniae* | 1000 | 270 |
| *Acinetobacter baumannii* Novo[R] | 280 | 190 |

TABLE 1-continued

MIC inhibitory concentrations of polymyxin B and novobiocin.

|  | Polymyxin B (ng/mL) | Novobiocin (µg/mL) |
| --- | --- | --- |
| *Pseudomonas aeruginosa* | >1000 | >450 |
| *Escherichia coli* | 110 | 20 |

Figure 1A:
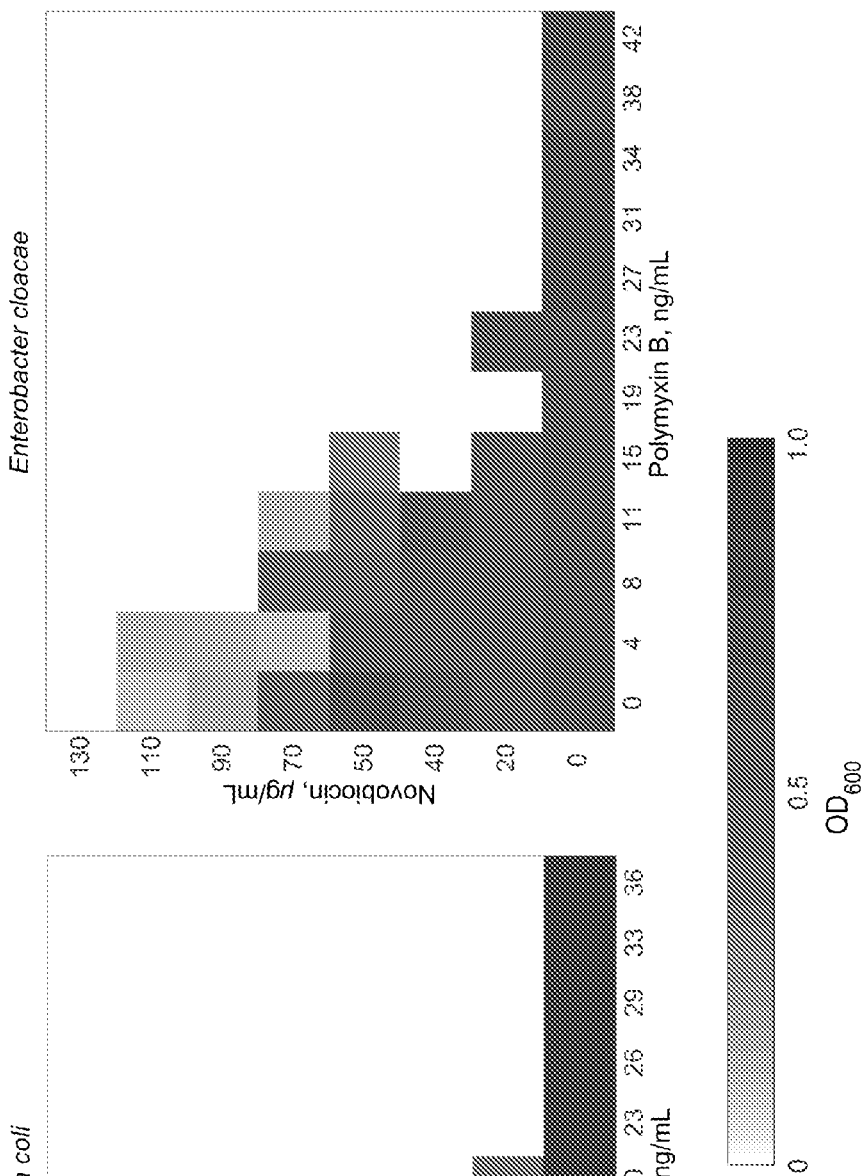
Figure 1B:
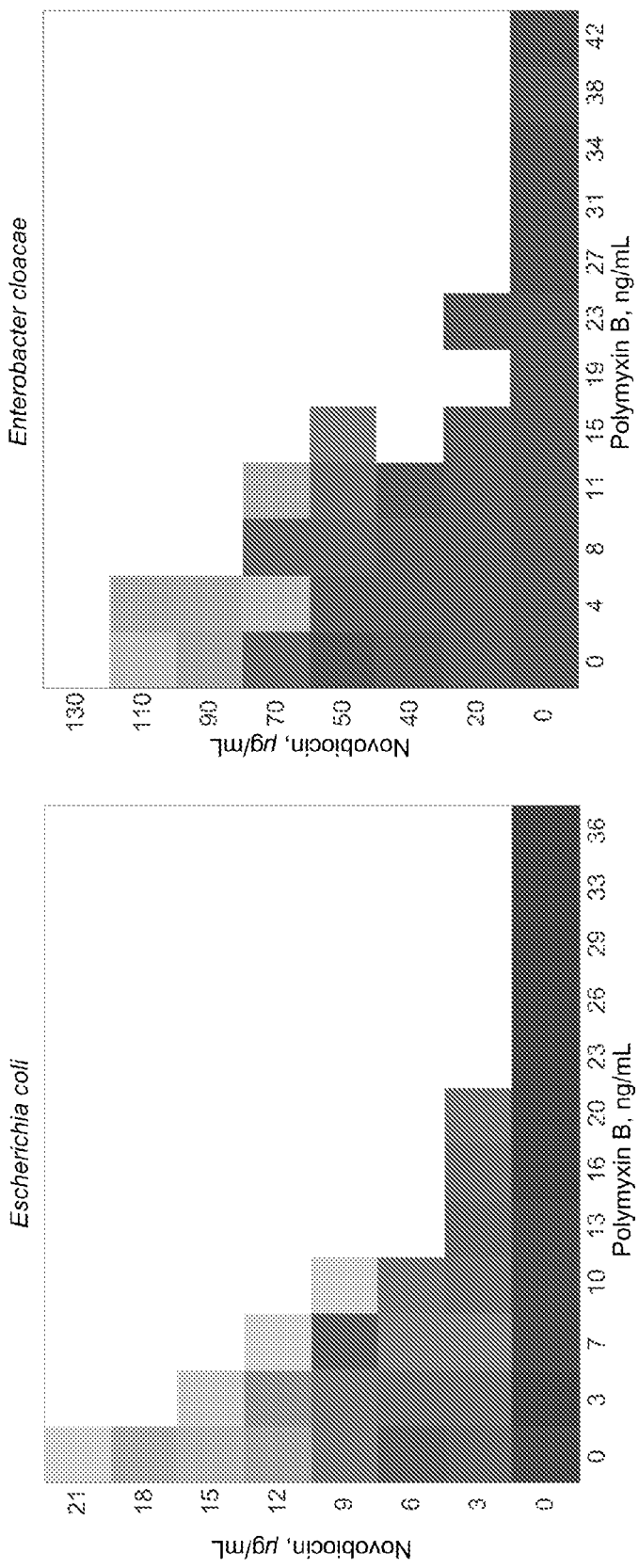
Figure 1D:
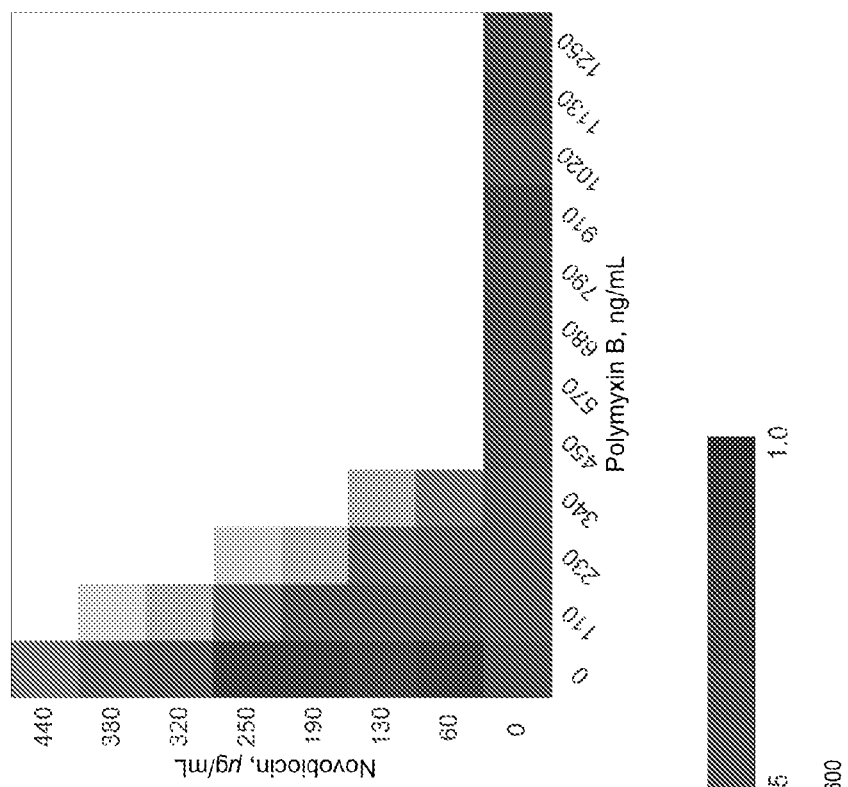
Figure 1C:
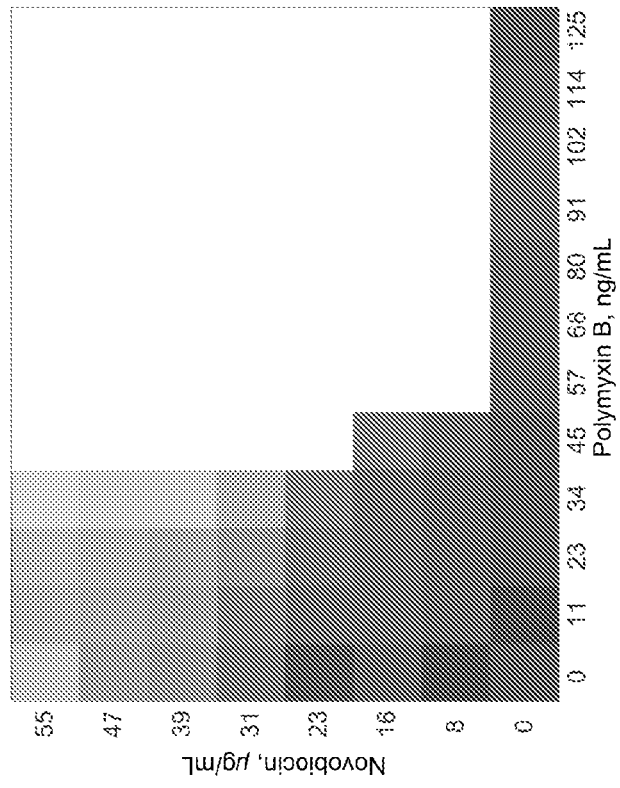
Figure 2C:
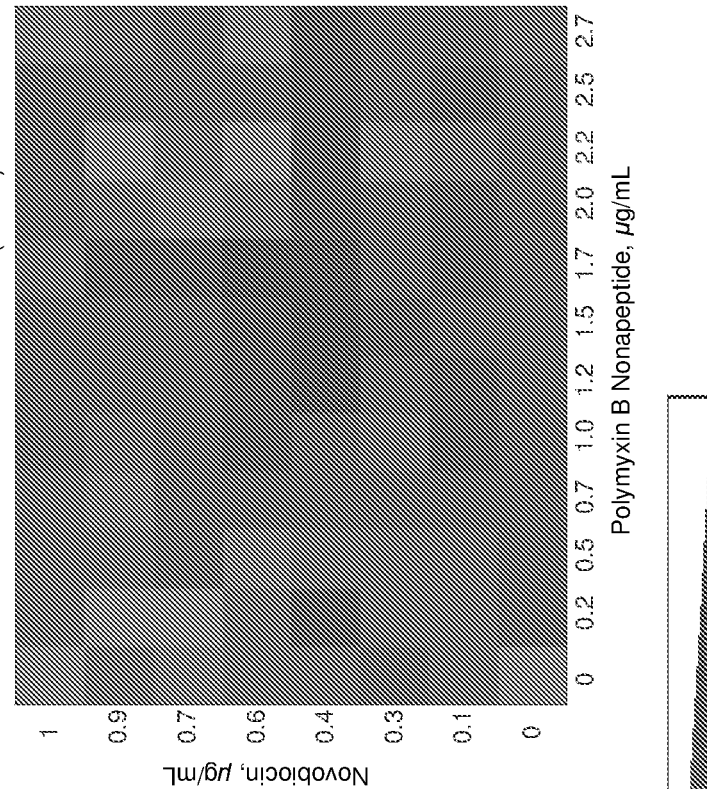
Figure 2B:
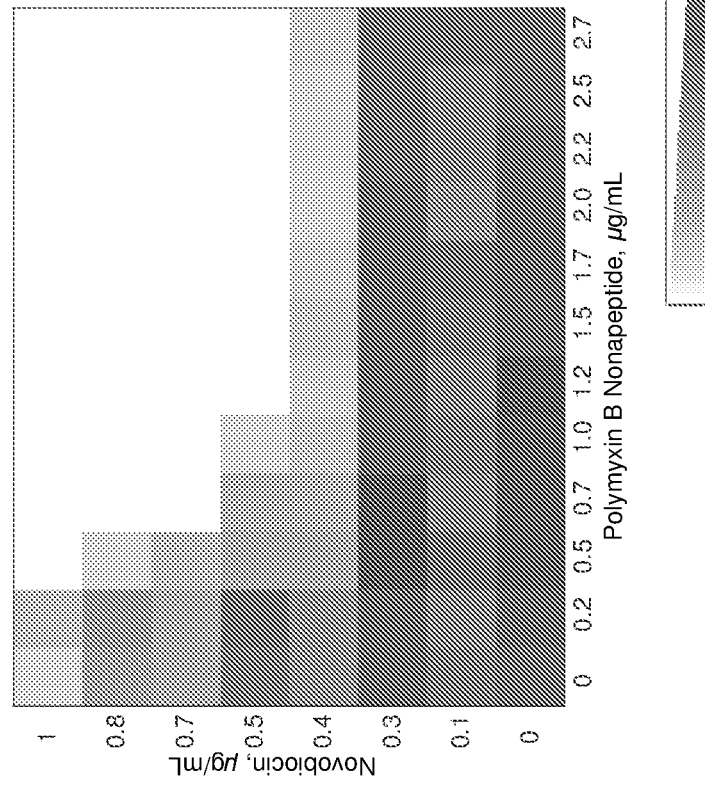
Figure 2E:
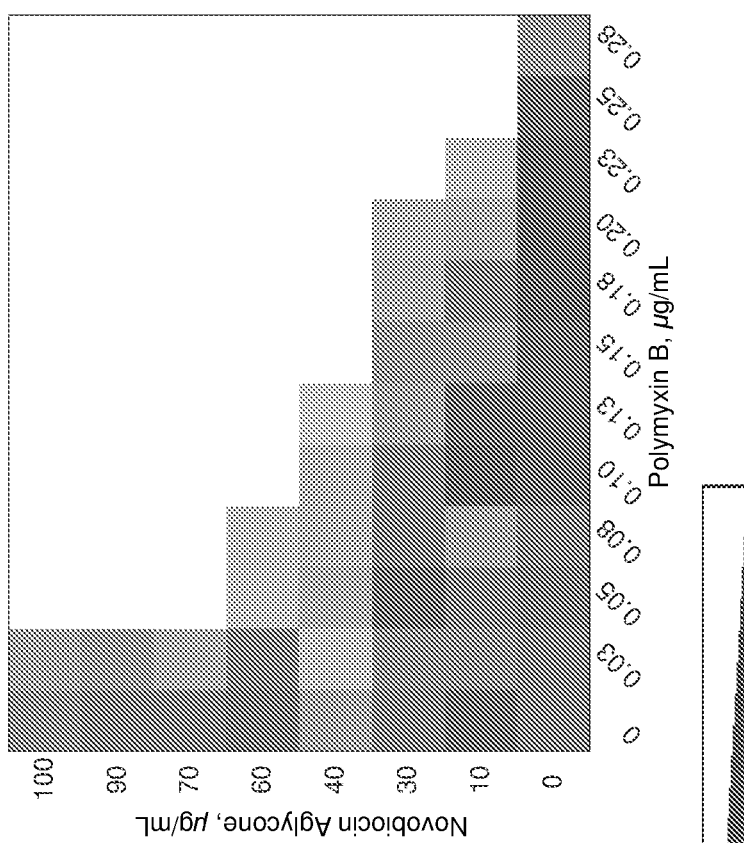
Figure 2D:
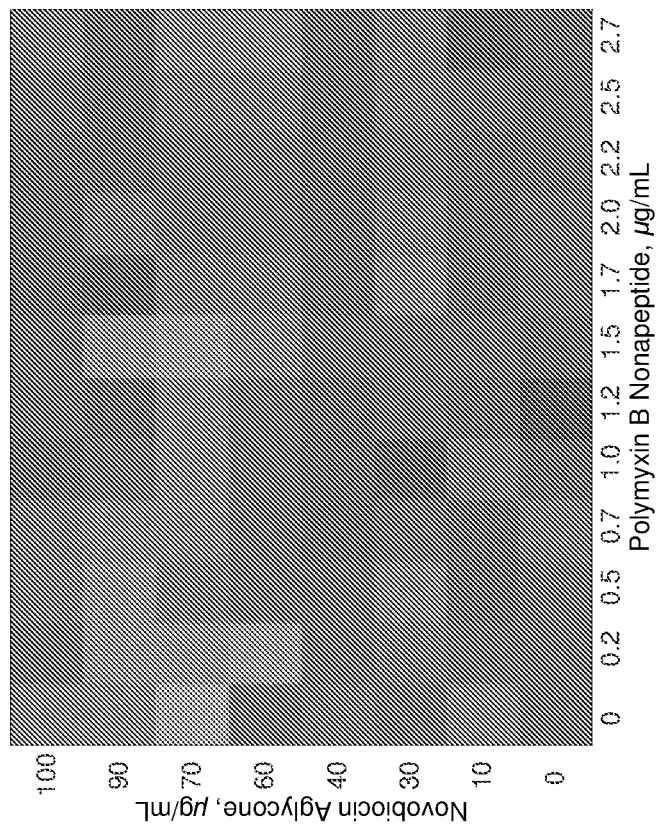
Figure 2F:
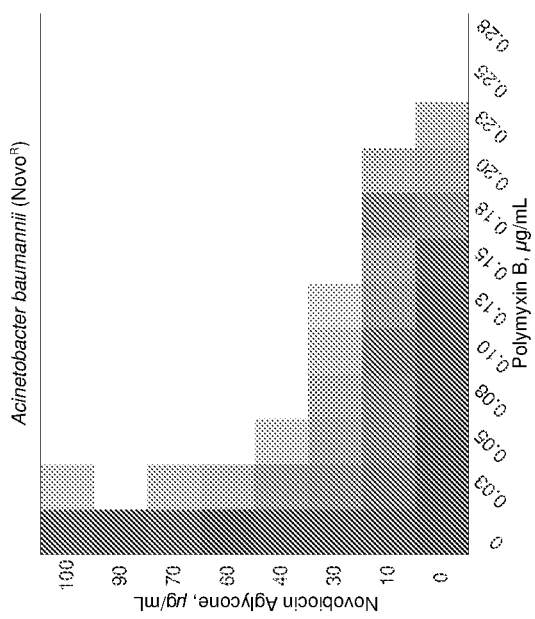
Figure 2G:
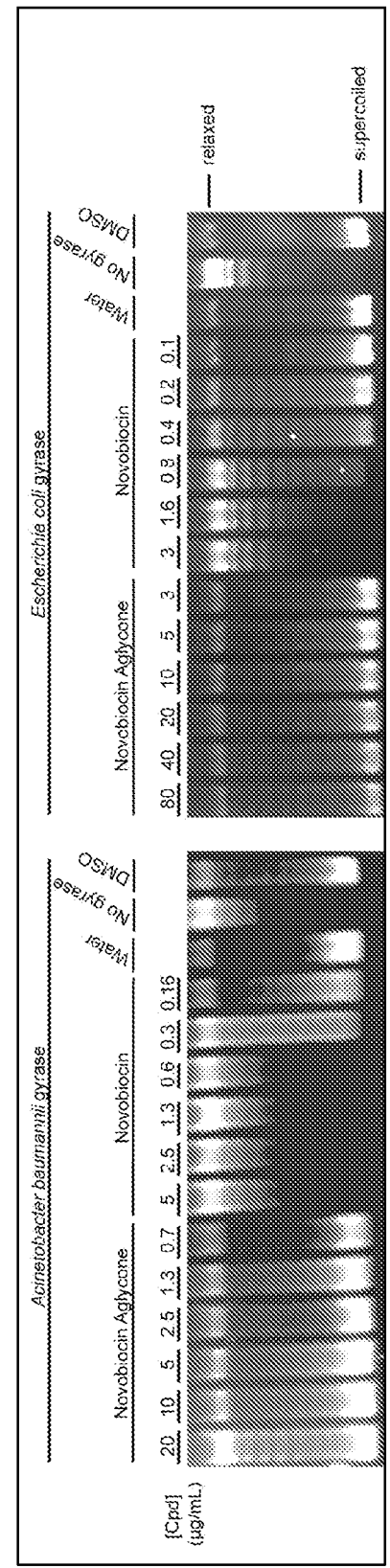
Figure 3B:
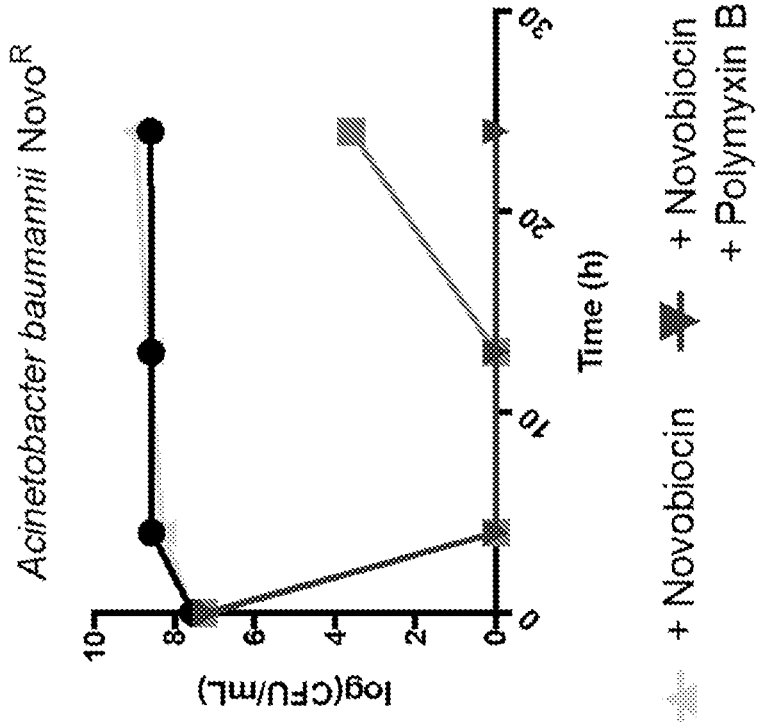
FIGS. 3A-3D are a set of plots of colony forming units/ml (CFU/ml) over time when untreated, or treated with polymyxin B, novobiocin, or a combination of both.
Figure 3A:
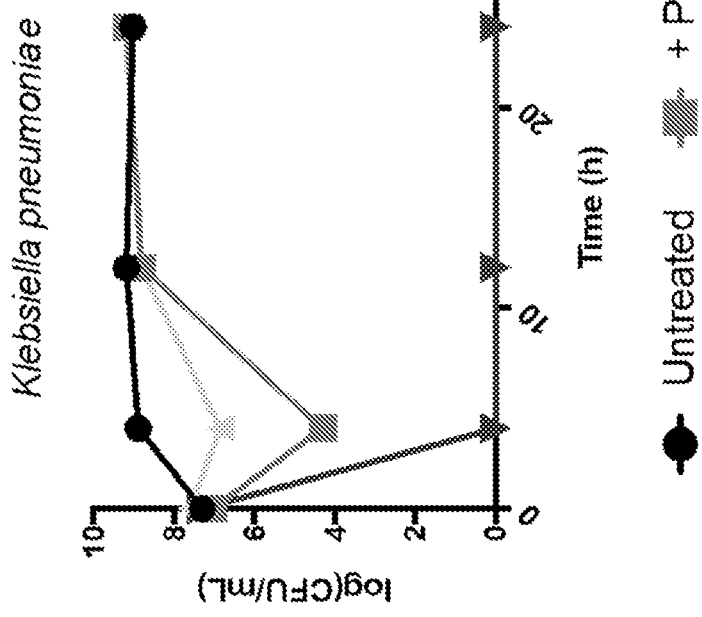
Figure 3D:
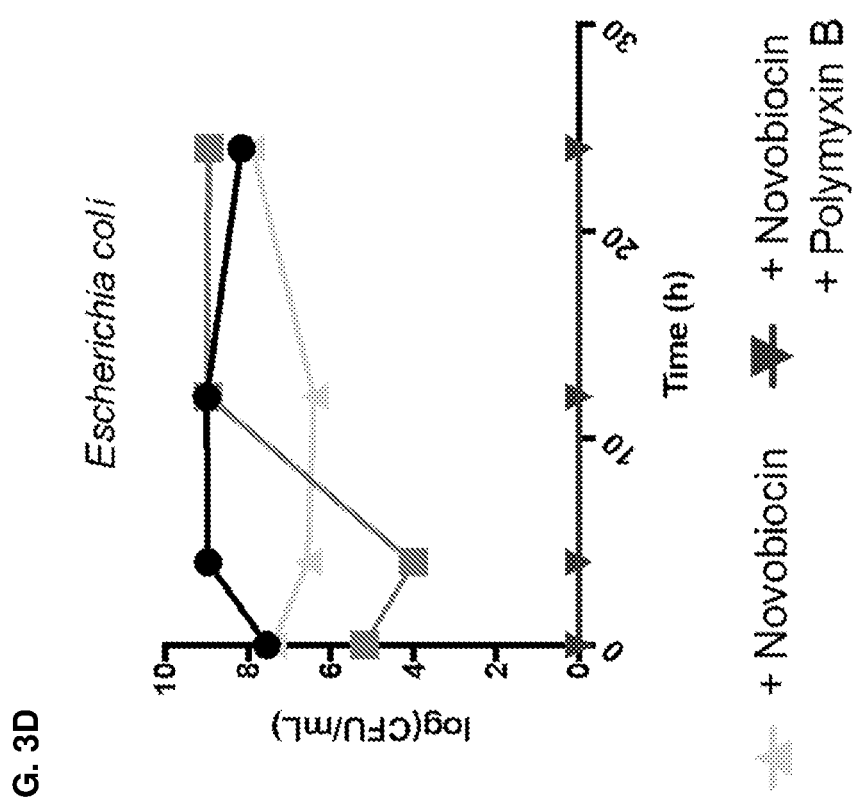
Figure 3C:
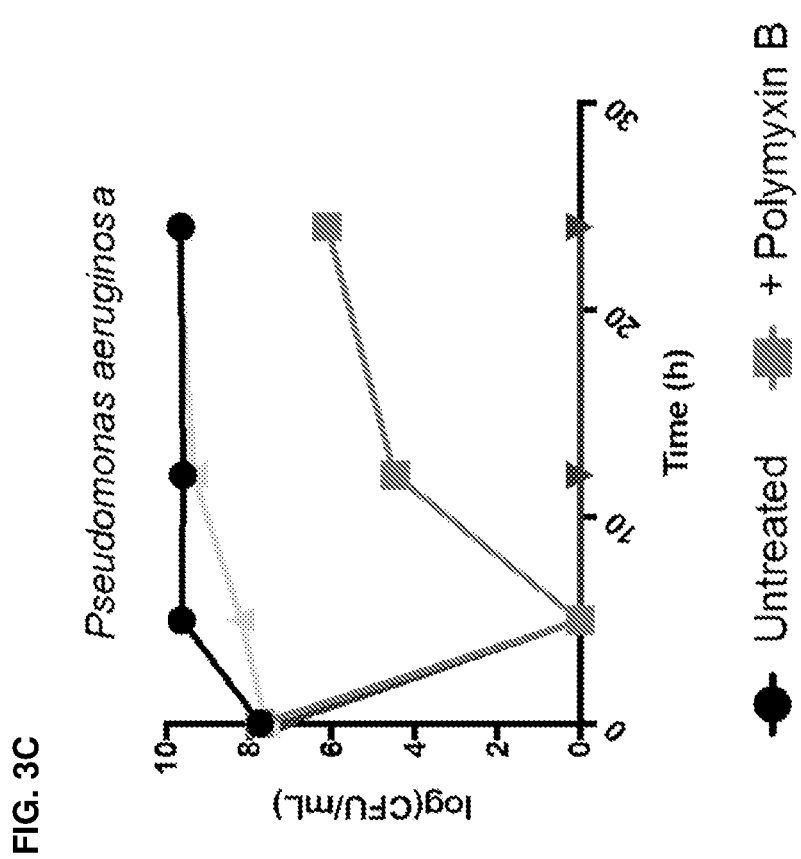

Checkerboard microdilution assays were also performed with PMB, PMBN, novobiocin, and novobiocin aglycone. As shown in FIG. 2A are the structures of PMB, PMBN, novobiocin (Novo), and novobiocin aglycone (NovoAgly). In FIG. 2B wild-type *A. baumannii* exhibits synergy between PMBN and novobiocin. In FIG. 2C, novo-resistant *A. baumannii* is resistant to the same combination of novobiocin and PMBN as in FIG. 2B. In FIG. 2D, novobiocin aglycone does not synergize with PMBN in wild-type *A. baumannii* (and Novo[R]; data not shown). In FIGS. 2E-2F, novobiocin aglycone synergizes with PMB in wild-type and Novo[R] *A. baumannii*. FIG. 2G shows that novobiocin aglycone has at least 70× reduce activity against *A. baumannii* and at least 100× reduced activity against *E. coli* gyrase. The data indicate that polymyxin B nonapeptide (PMBN) potentiates the gyrase inhibitor novobiocin, while having no effect on the gyrase-inactive novobiocin aglycone. Descarbamyl novobiocin also exhibited synergy with polymyxin B (data not shown).

A series of growth curves is shown in FIG. 3. Log(CFU/mL) vs. time curves. Overnight cultures were diluted 1:100 and grown at 37° C., 220 rpm until $OD_{600}=0.1$. This culture was transferred to four sterile 5 mL tubes and treated with polymyxin B, novobiocin, polymyxin B+novobiocin, or no drug and incubated at 37° C., 220 rpm. At each timepoint, 10 µL from each condition was $log_{10}$ diluted to $10^{-7}$ and subsequently plated on LB Miller agar containing no antibiotic. Time=0 h represents the CFU/mL count immediately after the initial treatment. Y-values of zero indicate fewer than 10,000 CFUs (limit of detection). Strains are identical to those used in FIG. 1. *K. pneumoniae*: [Novobiocin]=130 µg/mL, [Polymyxin B]=1.4 µg/mL; *A. baumannii*: [Novobiocin]=100 µg/mL, [Polymyxin B]=2.0 µg/mL; *P. aeruginosa*: [Novobiocin]=100 µg/mL, [Polymyxin B]=2.0 µg/mL; *E. coli*: [Novobiocin]=50 µg/mL, [Polymyxin B]=2.0 µg/mL. The data indicate that novobiocin and polymyxin B synergy is bactericidal.

Figure 18A:
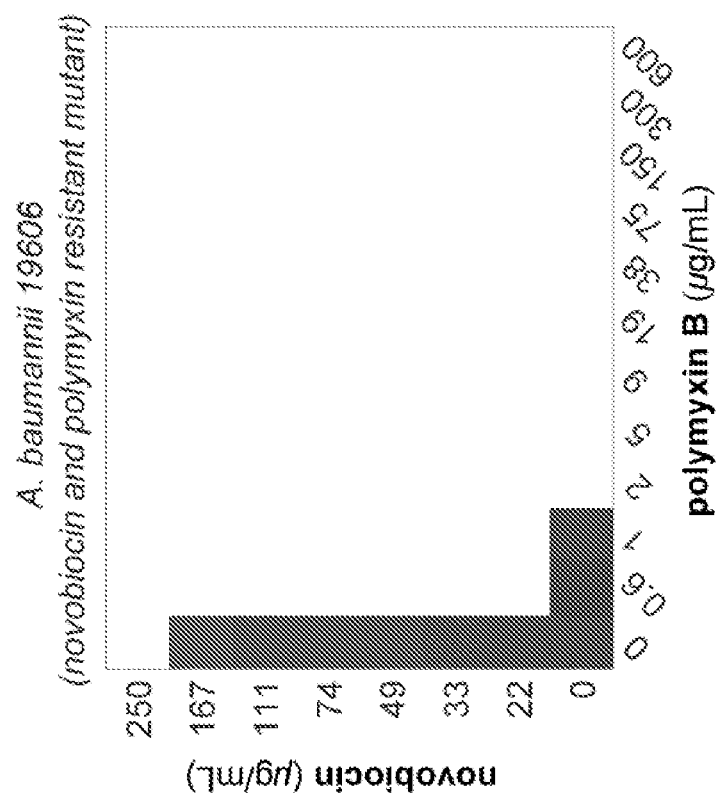
FIG. 18A is a graph of a checkerboard microdilution assay between polymyxin B and novobiocin in a polymyxin-resistant strain grown at 37° C. for 24 h, showing that novobiocin synergizes with polymyxin B to kill the Gram-negative, polymyxin-resistant *E. coli* (clinical isolate from Brigham and Women's Hospital) in vitro.
Figure 18B:
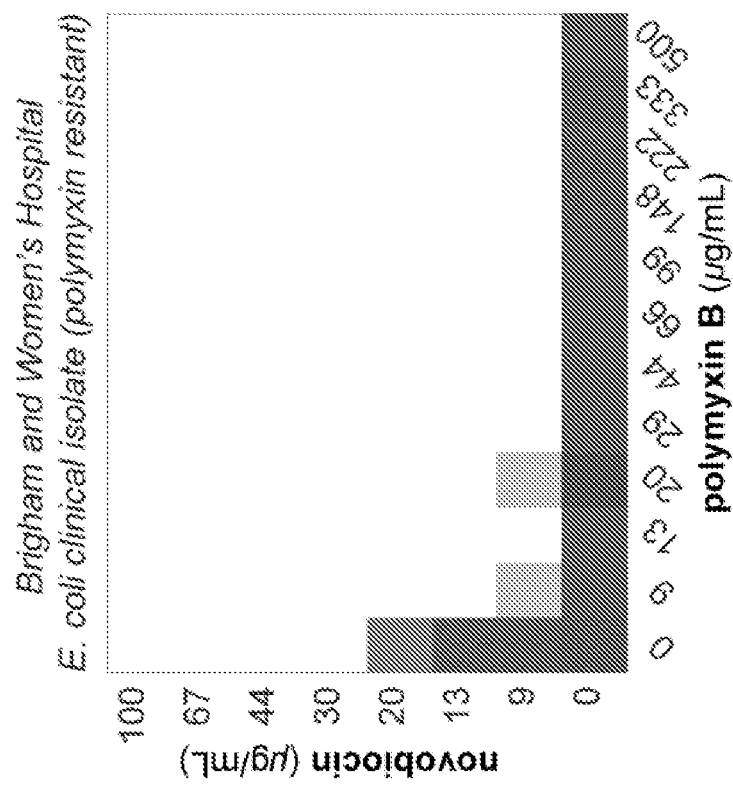
FIG. 18B is a graph of a checkerboard microdilution assay between polymyxin B and novobiocin in a novobiocin and polymyxin-resistant strain grown at 37° C. for 24 h, showing that novobiocin synergizes with polymyxin B to kill in vitro the Gram-negative *A. baumannii* (ATCC: 19606) mutant that is novobiocin and polymyxin-resistant.
Figure 18C:
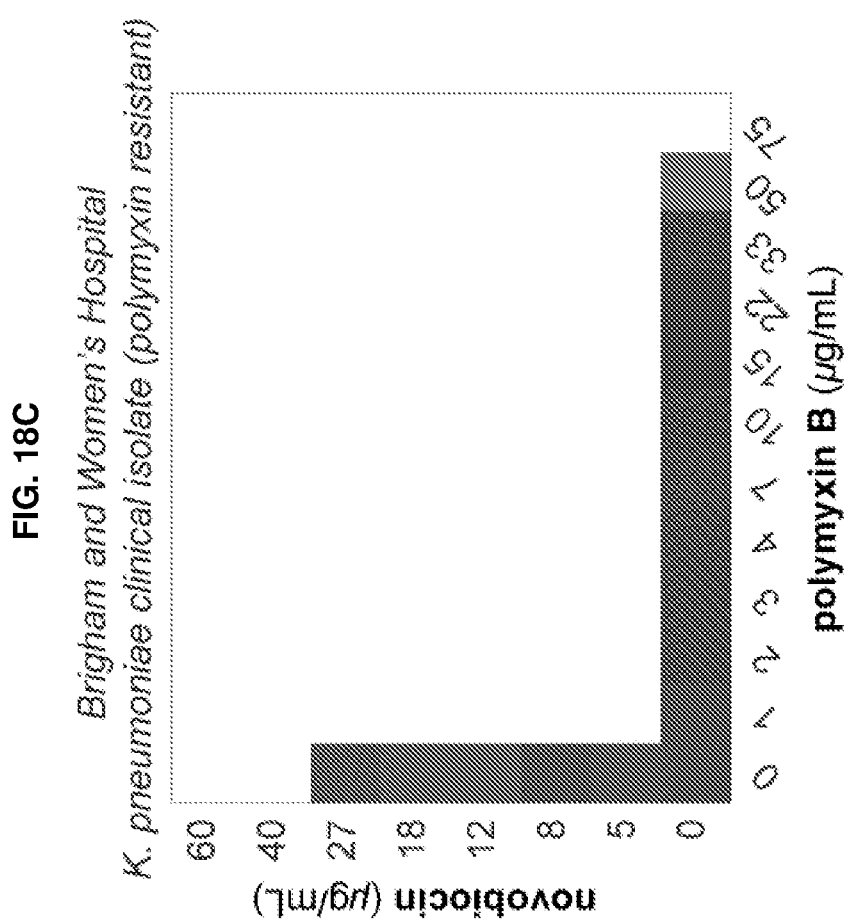
FIG. 18C is a graph of a checkerboard microdilution assay between polymyxin B and novobiocin in a polymyxin-resistant strain grown at 37° C. for 24 h, showing that novobiocin synergizes with polymyxin B to kill in vitro the Gram-negative, polymyxin-resistant *K. pneumoniae* (clinical isolate from Brigham and Women's Hospital) in vitro.

The effect of novobiocin/polymyxin combination was further assessed in polymyxin-resistant strains using checkerboard microdilution assays. In these assays, polymyxin-resistant strains (*E. coli* (clinical isolate from Brigham and Women's Hospital); *A. baumannii* (ATCC: 19606) mutant that is novobiocin and polymyxin-resistant; and *K. pneumoniae* (clinical isolate from Brigham and Women's Hospital)) were grown at 37° C. for 24 h. The results of these assays are illustrated in FIGS. 18A, 18B, and 18C. FIG. 18A shows that novobiocin synergizes with polymyxin B to kill the Gram-negative, polymyxin-resistant *E. coli* (clinical isolate from Brigham and Women's Hospital) in vitro. FIG. 18B shows that novobiocin synergizes with polymyxin B to kill in vitro the Gram-negative *A. baumannii* (ATCC: 19606) mutant that is novobiocin and polymyxin-resistant. FIG. 18C shows that novobiocin synergizes with polymyxin B to kill in vitro the Gram-negative, polymyxin-resistant *K. pneumoniae* (clinical isolate from Brigham and Women's Hospital) in vitro.

Example 2. Neutropenic Mouse Thigh Infection Efficacy

Animals

Female CD-1 mice from Charles River Laboratories were allowed to acclimate for 5 days prior to start of study.

Animals were housed four per cage with free access to food and water. Mice received two doses of cyclophosphamide on days −4 and −1 with 150 mg/kg and 100 mg/kg delivered IP, respectively. All procedures were performed to NeoSome IACUC policies and guidelines as well as OLAW standards.

Inoculum Preparation

*E. coli* strain ATCC 25922 was prepared for infection from an overnight plate culture. A portion of the plate was resuspended in sterile saline and adjusted to an OD of 0.15 at 625 nm. The adjusted bacterial suspension was further diluted to target an infecting inoculum of $1.5 \times 10^5$ CFU/mouse, the actual inoculum size for *E. coli* was $1.45 \times 10^5$ CFU/mouse. Plate counts of the inoculum was performed to confirm inoculum concentration.

Infection

Mice were inoculated with 100 μL of the prepared bacterial suspension via intramuscular injection into the right rear thigh.

Efficacy

Beginning at two hours post infection, mice were dosed with test agents subcutaneously at 10 mL/kg. A second dose of test agents was delivered at 6 hours post infection. For co-administered therapy, test agents were delivered separately at two different injection sites. Four animals were dosed per group. One group of four mice were euthanized at initiation of therapy (T=2 h) and CFUs determined. All remaining mice were euthanized at 26 hours post infection. At termination, thighs were aseptically excised, weighed, and homogenized to a uniform consistency in 2 mL of sterile saline. The homogenate was serially diluted and plated on bacterial growth media. The CFUs were enumerated after overnight incubation. The average and standard deviations for each group were determined.

Results

Neutropenic mice infected with *E. coli* were treated with novobiocin, polymyxin B, or a combination of the two for the evaluation of efficacy is a thigh infection model. Mice were infected with *E. coli* ATCC 25922 demonstrated a 4.09 $\log_{10}$ CFU increase in bio-burden from the 2 hour to 26 hour sampling in the infection control groups. The results are summarized in Table 2 below.

TABLE 2

*E. coli* infection of mouse thighs

| Group ID | Dose (mg/kg) | Total Dose (mg/kg) | Route/ regimen | Average $\log_{10}$ CFU/g of thigh | St. Dev. | change in $\log_{10}$ CFU/g of thigh from 2 hour control | change in $\log_{10}$ CFU/g of thigh from 26 hour controls |
|---|---|---|---|---|---|---|---|
| T = 2 hr | n/a | | | 5.54 | 0.07 | | −4.09 |
| 26 hr. Inf. Cntrl | n/a | | n/a | 9.62 | 0.29 | 4.09 | |
| Novobiocin | 200 | 400 | BID/SC | 9.12 | 0.71 | 3.58 | −0.51 |
| Polymyxin B (PMB) | 1 | 2 | BID/SC | 6.02 | 0.92 | 0.49 | −3.60 |
| | 0.3 | 0.6 | BID/SC | 8.92 | 0.97 | 3.38 | −0.70 |
| | 0.1 | 0.2 | BID/SC | 9.49 | 0.14 | 3.95 | −0.13 |
| | 0.03 | 0.06 | BID/SC | 9.44 | 0.24 | 3.91 | −0.18 |
| PMB:novobiocin | 0.3:200 | 0.6:400 | BID/SC | 4.79 | 0.25 | −0.75 | −4.83 |
| | 0.1:200 | 0.2:400 | BID/SC | 8.63 | 0.66 | 3.10 | −0.99 |
| | 0.03:200 | 0.06:400 | BID/SC | 8.72 | 1.01 | 3.19 | −0.90 |

Novobiocin delivered at 200 mg/kg did not demonstrate significant activity against this isolate. Polymyxin B delivered as a single agent demonstrated significant activity at 0.2 and 1 mg/kg with reductions in CFUs from the 26 hour infection controls of 0.70 and 3.60 $\log_{10}$ CFU/gram of thigh, respectively. Polymyxin B co-administered with novobiocin demonstrated an increase in antibacterial activity over the polymyxin B monotherapy. PMB:novobiocin delivered at 0.3 mg/kg:200 mg/kg demonstrated a 4.83 $\log_{10}$ CFU reduction from the 26 hour infection controls and a 0.75 $\log_{10}$ CFU reduction from the 2 hour infection controls, a 4.13 $\log_{10}$ reduction of CFU/g relative to the polymyxin B only therapy at the equivalent dose.

Example 3. Bactericidal Synergy Between Novobiocin Aglycone and Polymyxin B

Figure 5A:
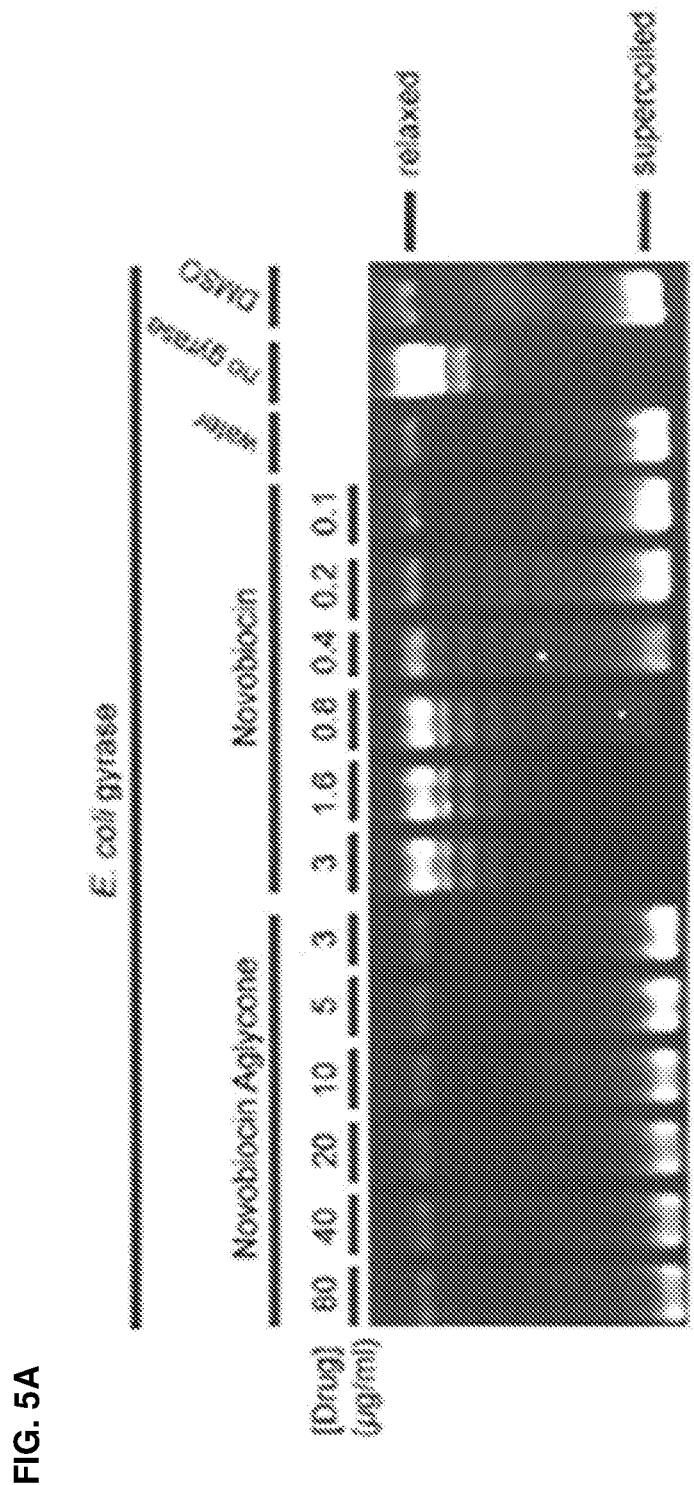
FIG. 5A is a picture of a gel showing an in vitro gyrase supercoiling assay that shows that novobiocin aglycone does not inhibit E. coli gyrase activity.
Figure 5B:
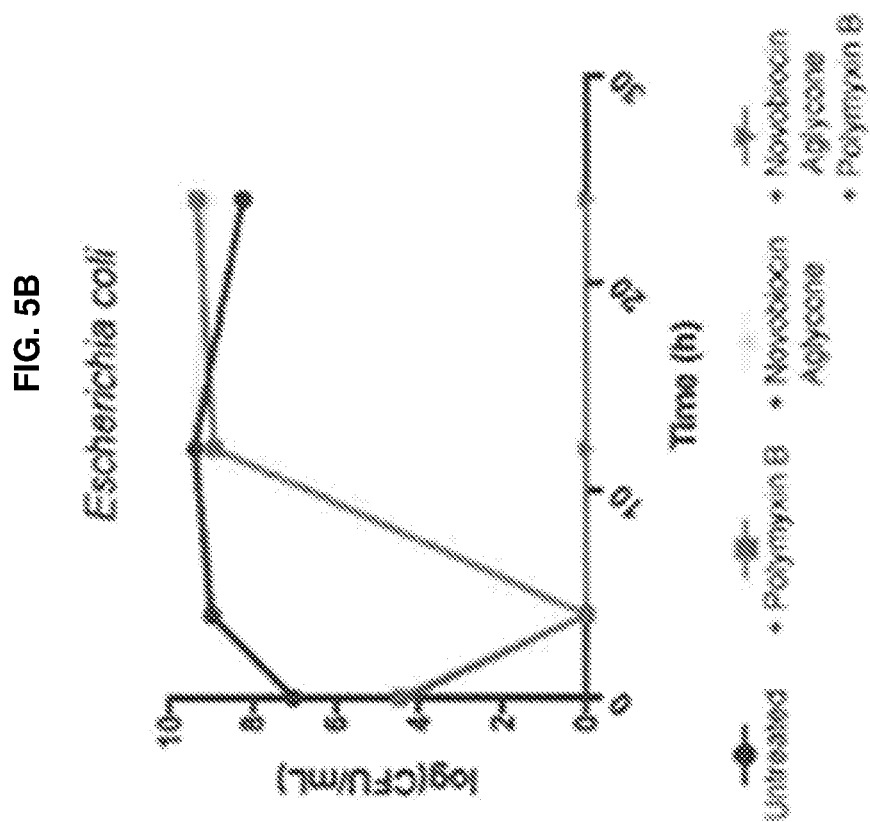
FIG. 5B is a graph showing that the combination of novobiocin aglycone and polymyxin B is bactericidal.

An in vitro gyrase supercoiling assay was performed with novobiocin aglycone and novobiocin (FIG. 5A) that shows that novobiocin aglycone does not inhibit *E. coli* gyrase activity. The combination of novobiocin aglycone and polymyxin B is bactericidal, as shown in FIG. 5B. These results suggest a killing mechanism that does not involve gyrase inhibition.

Example 4. Investigating the Novobiocin Binding Site

To better understand how LptB$_2$FG functions, we made *E. coli* strains that have defects in the assembly machinery that make them permeable to antibiotics. One such strain, IptB1, was sensitive to a panel of antibiotics that do not kill wild-type *E. coli* (FIG. 6B, Table 3).

TABLE 3 lptB1(R144H) selectively suppresses novobiocin sensitivity.

| | Zone of inhibition (in mm) | | | | |
|---|---|---|---|---|---|
| | Bacitracin | Novobiocin | Erythromycin | Rifampicin | Nalidixic acid |
| wild type | <6 | <6 | (8) | 8(9) | 11(14) |
| lptB1 | 17 | 14(24) | 16(21) | 17 | 18(21) |
| lptB1(G33C) | (8) | <6 | (11) | 9 | 12(14) |
| lptB1(R144H) | 17 | <6 | (16) | 24 | 17(20) |

Figure 6B:
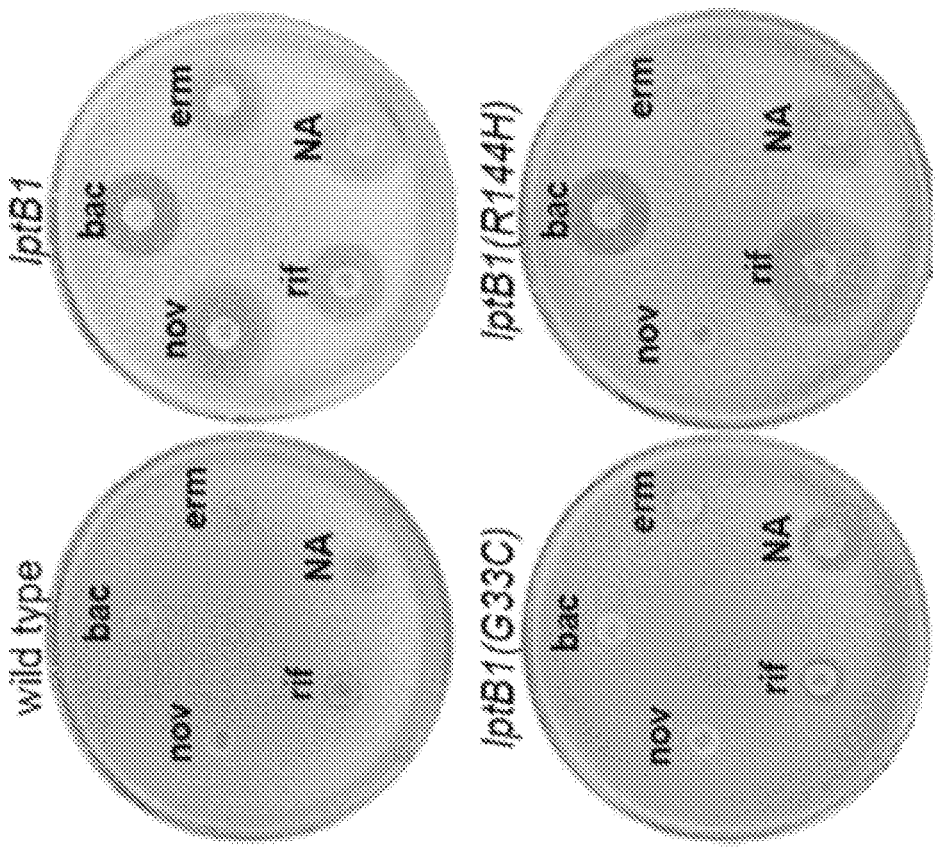
FIG. 6B is a picture of bacterial lawns grown on plates in the presence of disks containing antibiotics. A zone of growth inhibition around the disks was taken as an indicator of susceptibility to novobiocin (nov), bacitracin (bac), erythromycin (erm), rifampicin (rif), and nalidixic acid (NA). The genotype of the strains tested is indicated above each plate; IptB$_I$ encodes a defective LptB ATPase that renders the strain generally susceptible to antibiotics when compared to the wild-type strain. Additional suppressor mutations in IptB$_I$ can make it less sensitive to all antibiotics [IptB$_I$ (G33C)] or to novobiocin only [IptB$_I$ (R144H)].
Figure 6A:
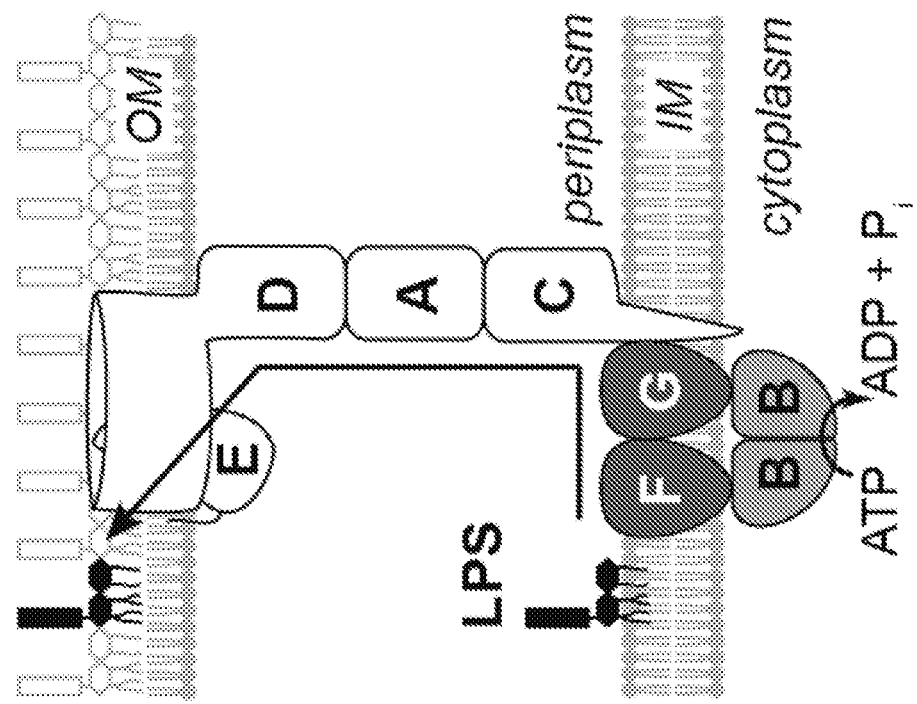
FIG. 6A is a schematic drawing of the lipopolysaccharide (LPS) transport system.

Zones of inhibition were measured in disk diffusion assays of wild type, lptB1, and suppressors lptB1(R144H) and lptB1(G33C) pictured in FIG. 6B. Assays were conducted with 6-mm disks. Numbers outside of parentheses report the diameter of the zone of total growth inhibition (in mm), while numbers inside parenthesis report the diameter of the zone of partial growth inhibition.

We raised resistant mutants to these antibiotics in the lptB1 background and obtained two classes of suppressor alleles encoding amino acid changes in lptB1. One class, exemplified by lptB1(G33C), conferred resistance to all antibiotics tested, presumably by correcting the defect in lptB1 function (FIG. 6B bottom left, Table 3). The other class of suppressors, exemplified by lptB1(R144H), conferred resistance only to novobiocin (FIG. 6B bottom right, Table 3), a known DNA gyrase inhibitor. 11 We found that lptB1(R144H) does not confer resistance to another gyrase inhibitor, 12 nalidixic acid (FIG. 6B bottom right, Table 3). Therefore, we speculated that novobiocin might interact directly with LptB and affect the function of LptB2FG. This idea was supported by studies indicating that novobiocin inhibits the human BCRP ABC transporter through an unknown mechanism.

Figure 8A:
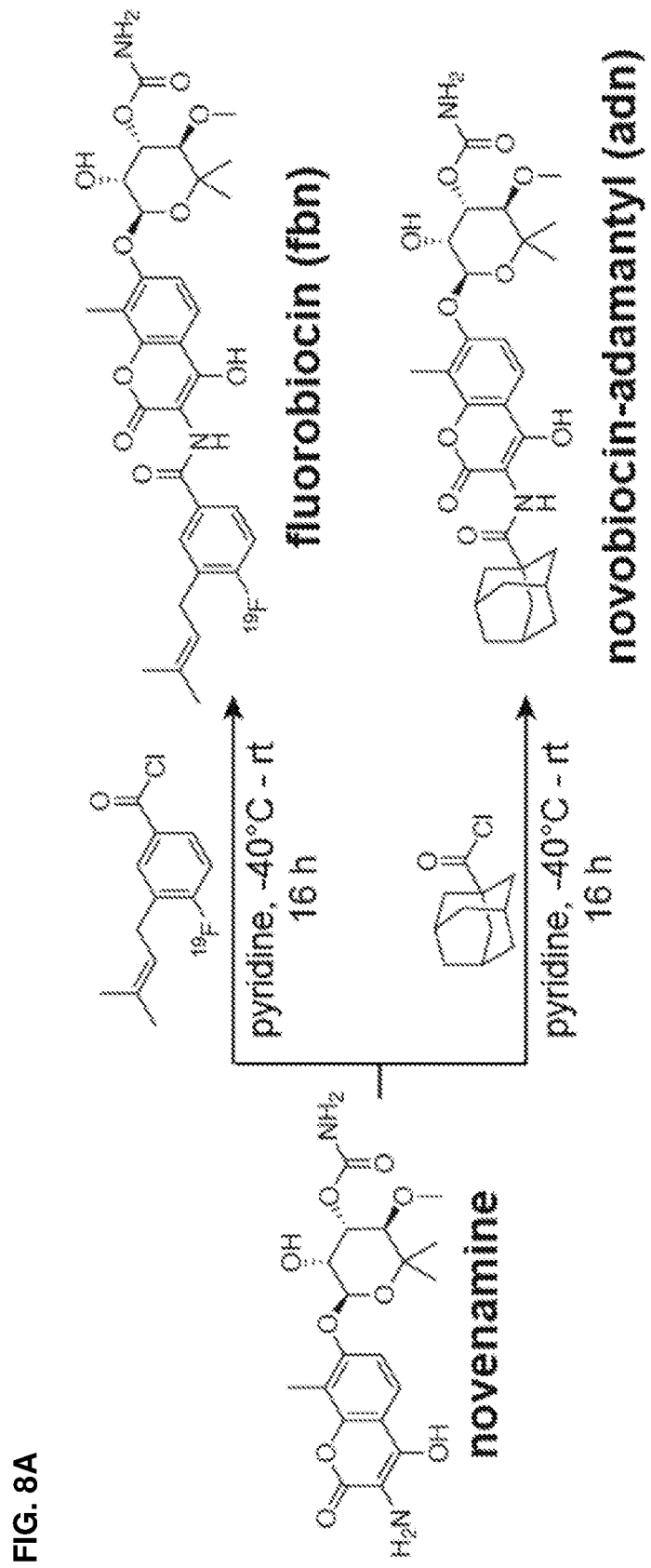
FIG. 8A is a scheme showing the synthesis of fluorobiocin (fbn) and nonobiocin-adamantyl (adn).
Figure 11B:
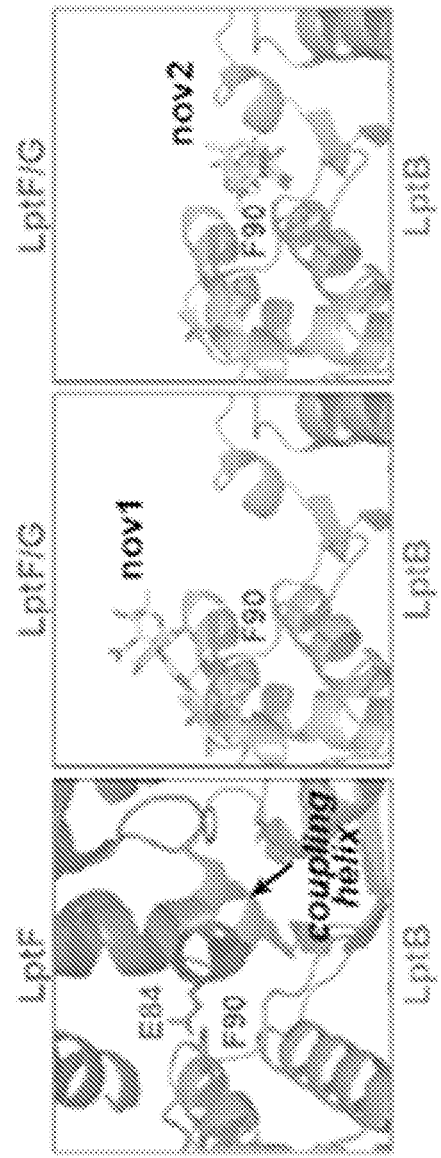
FIG. 11B is a set of three schematic drawings comparing the groove region of LptB and LptF from *Pseudomonas aeruginosa* (PDB: 5X5Y) with that of LptB-ADP-NOV. As each LptB monomer contacts both novobiocin molecules, there are two potential novobiocin binding sites (nov1 and nov2). The nov1 site is positioned to the side of the groove, while the nov2 site occludes the groove, suggesting it is not the relevant site.
Figure 11A:
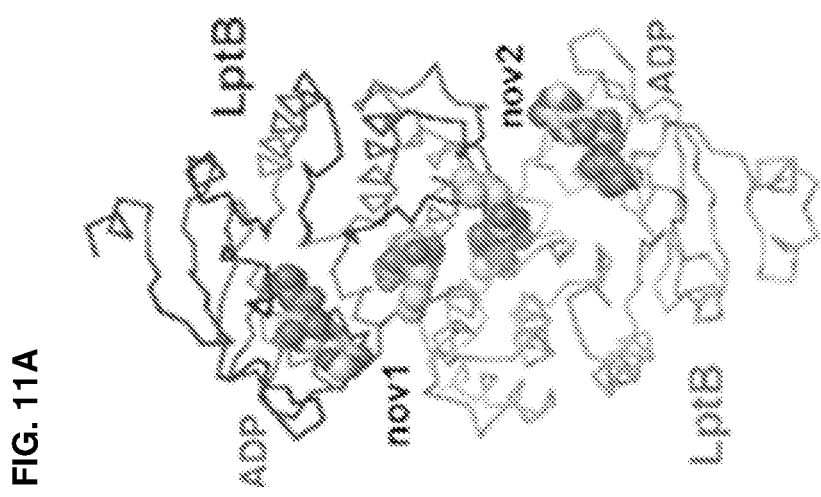
FIG. 11A is schematic drawing of two molecules of novobiocin found in the structure (LptB-ADP-NOV) bound symmetrically at the crystallographic dimer interface.
Figure 11C:
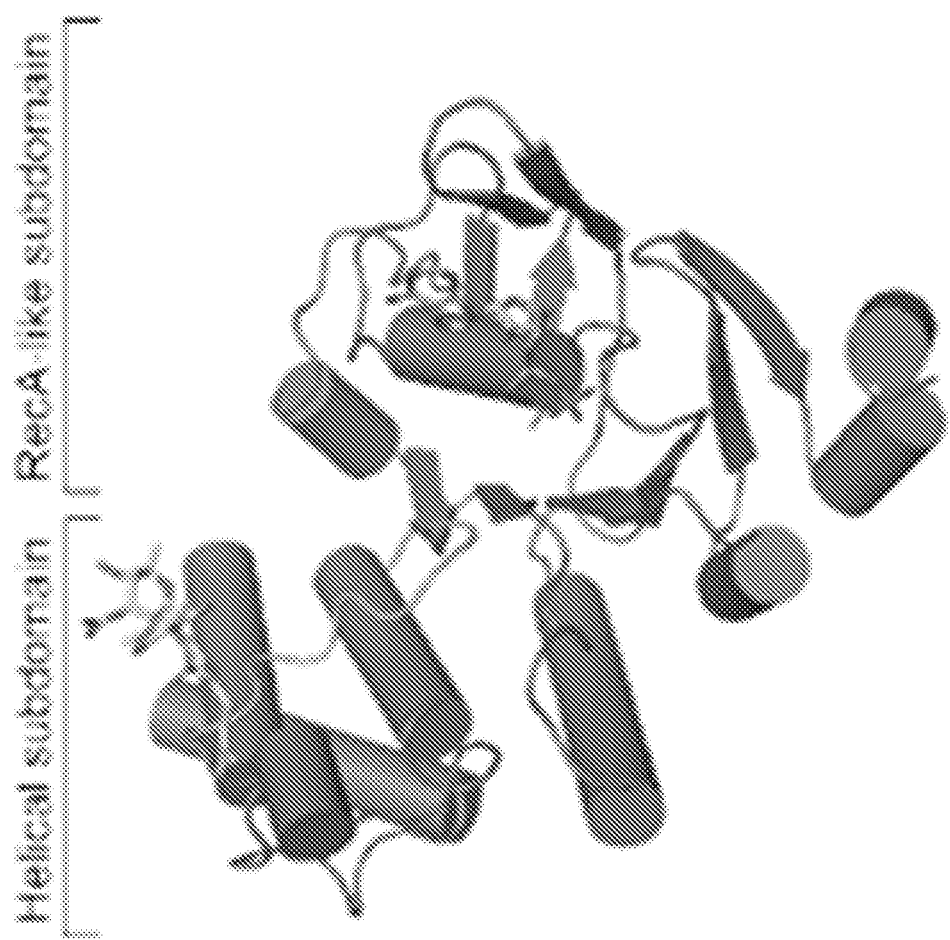
FIG. 11C is a schematic drawing showing that the nov1 site is located in the helical subdomain, which coordinates interactions with the transmembrane domains.
Figure 12:
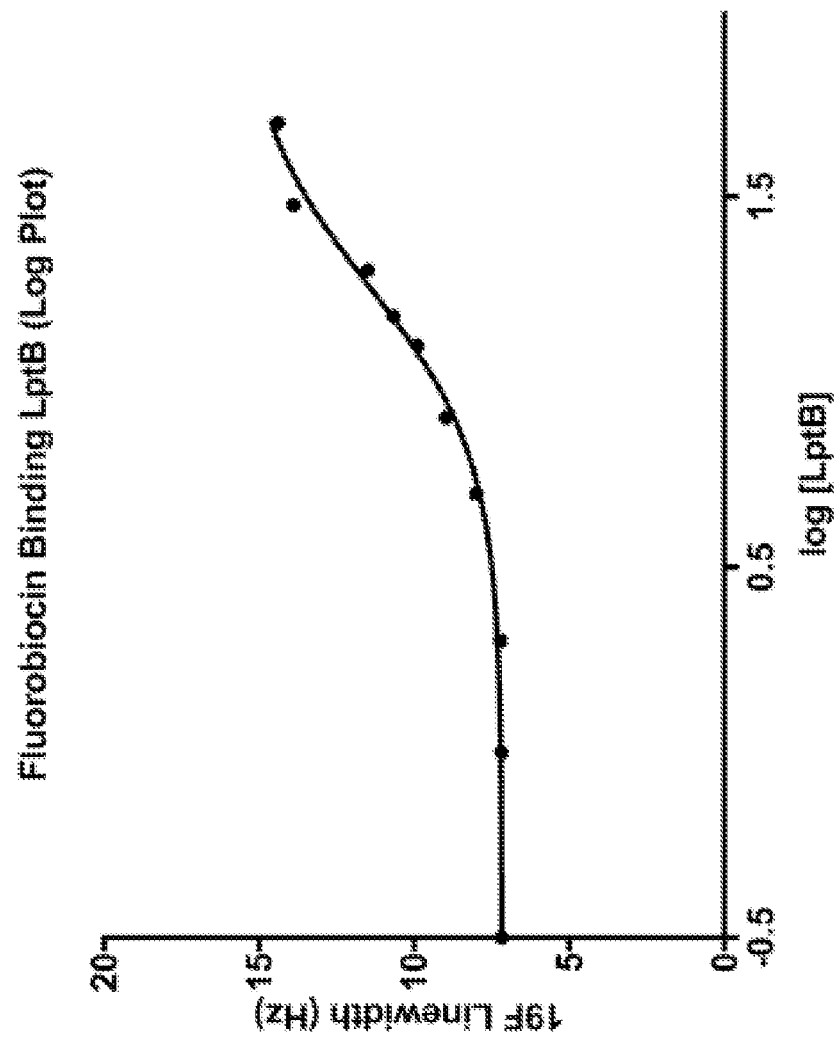
FIG. 12 is a graph showing the $^{19}$F NMR linewidth of fluorobiocin (fbn) plotted vs. log[LptB]. Data were analyzed with GraphPad Prism 7 software using a nonlinear fit, log(agonist) vs. response with an R$^2$=0.9909. The K$_D$ was calculated to be 18 μM.

We soaked novobiocin into LptB-ADP crystals and obtained a 2.0-Å structure of a co-complex (FIG. 7A, FIG. 11). ADP is still present in the co-complex, and novobiocin binds adjacent to the groove in LptB that accommodates the coupling helices from LptFG (FIG. 7B, FIG. 11). Coupling helices are a conserved motif in ABC systems that connect the transmembrane domains (here, LptFG) to the nucleotide-binding domains (here, LptB). Notably, novobiocin contacts LptB residue F90 (FIG. 7C), which interacts with LptFG. This residue is invariant in LptB, and non-conservative substitutions at this position are lethal because they disrupt proper formation of the LptB2FG complex. Novobiocin thus binds a critical position at the LptBLptFG interface. To estimate the affinity of novobiocin for LptB, we synthesized an otherwise identical analogue in which a phenolic hydroxyl was substituted with a 19F-label (fluorobiocin, FIG. 8A). Solution NMR binding experiments indicate that fluorobiocin is a low micromolar binder (FIG. 12).

Figure 8B:
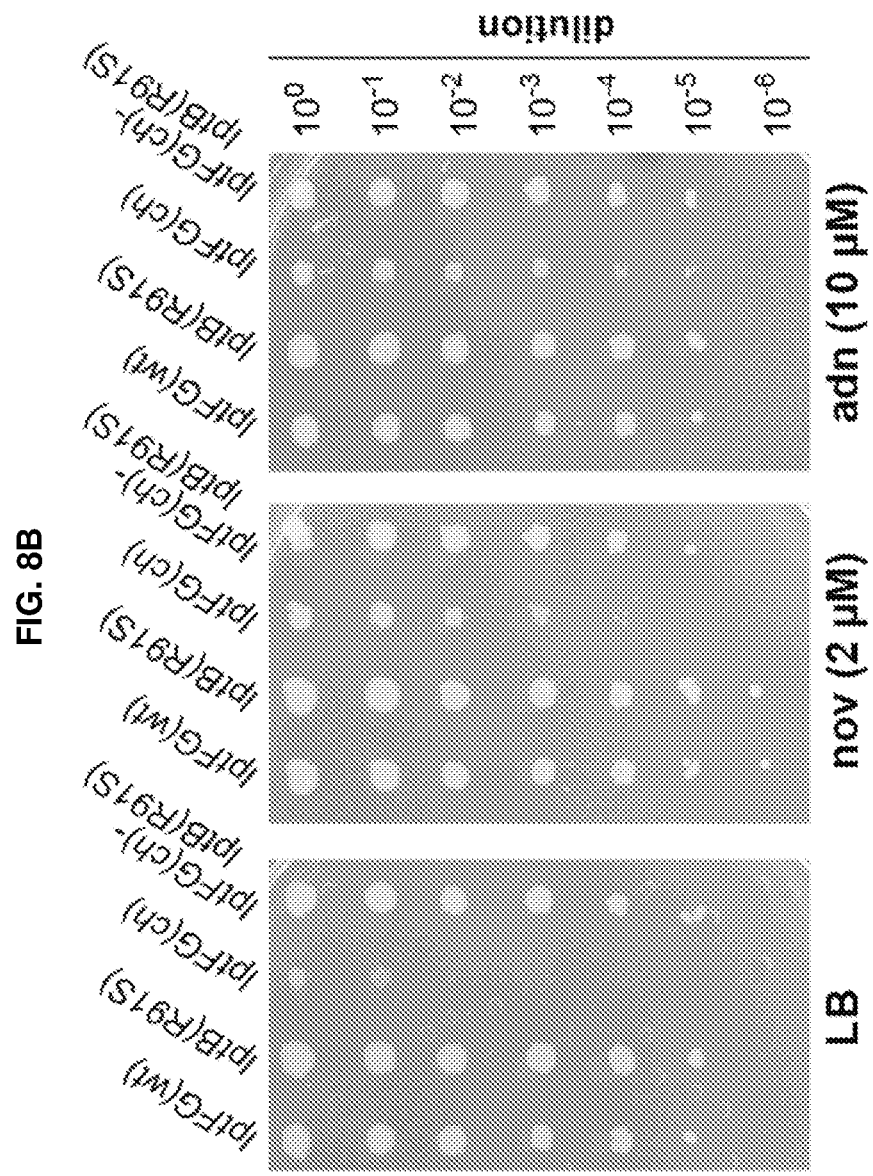
FIG. 8B is a series of pictures of bacterial overnight cultures grown in minimal medium. The cultures were serially diluted ten-fold and spotted onto LB agar plates with and without compounds. Novobiocin and novobiocin-adamantyl rescued growth defects of the coupling helix mutant IptFG(ch) similarly to the genetic suppressor IptFG(ch)-IptB(R91S).

We wondered whether novobiocin binds to LptB in cells, as suggested by the resistance mutation in lptB1. The coupling helices in LptFG each contain a strictly-conserved glutamate, and changing both glutamates to alanine (lptFG (ch)) causes a lethal loss of function (FIG. 8B, LB panel). We previously found that the lptFG(ch) mutant can be rescued by replacing the charged arginine side chain at position 91 in LptB to an uncharged serine (FIG. 8B, compare lptFG(ch) and lptFG(ch)-lptB(R91S)). Because novobiocin also contacts R91 (FIG. 7C), we speculated that it might rescue growth of lptFG(ch) by masking the charge. Indeed, we found that novobiocin enables the lptFG(ch) mutant to grow (FIG. 8B). We conclude that novobiocin suppresses Lpt defects in vivo by interacting with LptB at R91; therefore, novobiocin interacts with LptB in cells in a similar manner to that observed in the crystal structure.

Figure 8C:
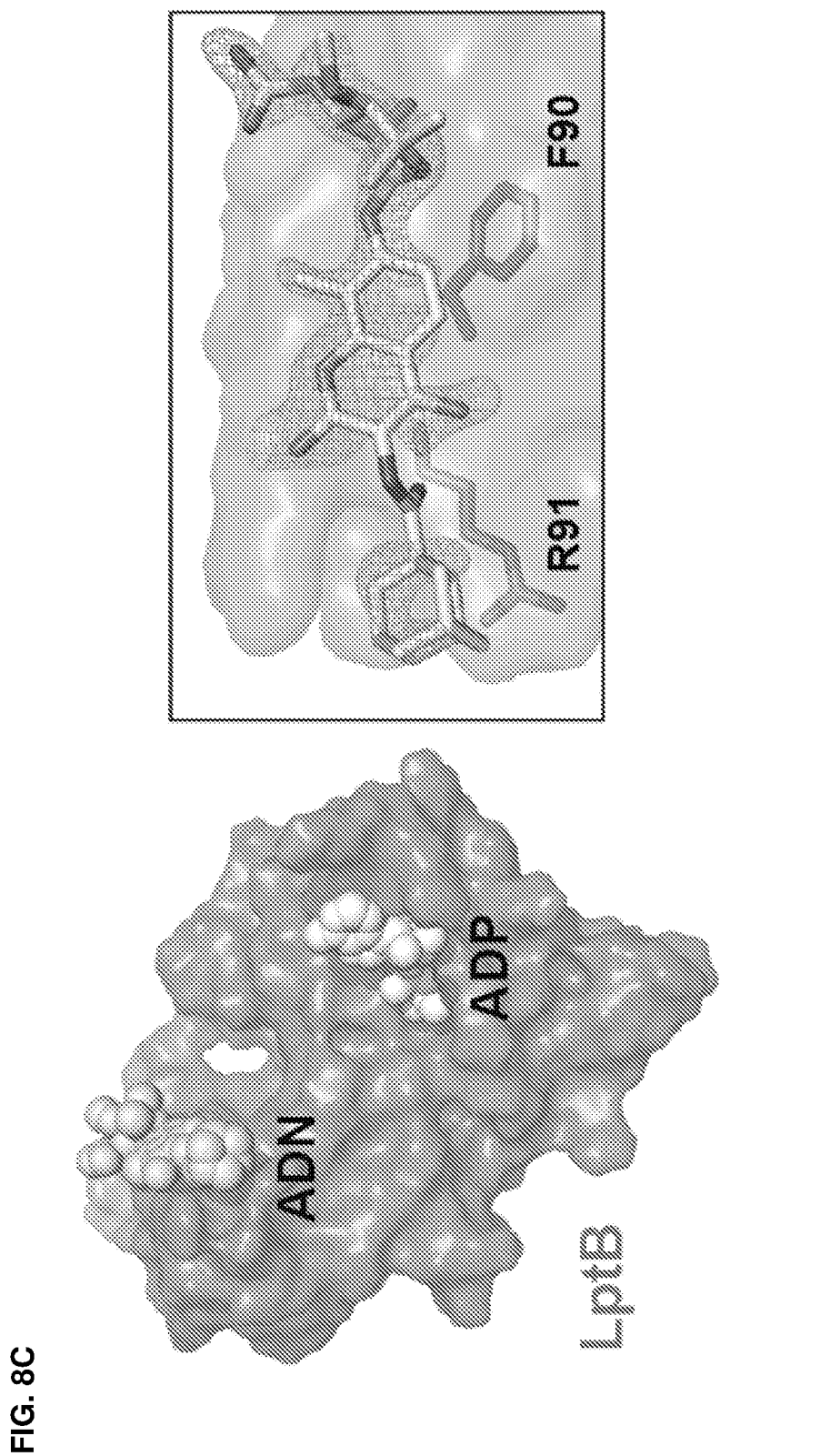
FIG. 8C is a surface rendering of novobiocin-adamantyl co-crystallized with LptB showing that it binds to LptB in the novobiocin-binding site (LptB-ADP-ADN). The Fo-Fc omit map is contoured at 3σ
Figure 13:
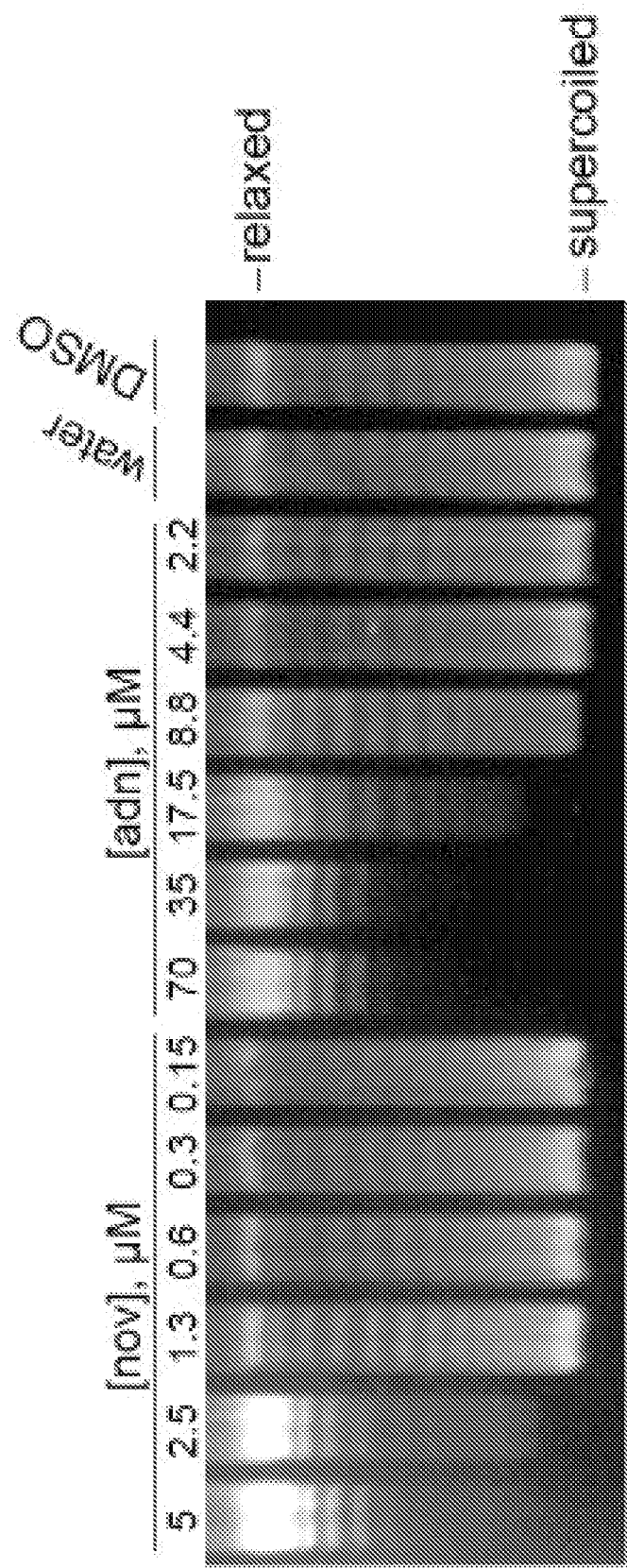
FIG. 13 is a picture of a gel showing that novobiocin-adamantyl (adn) has reduced activity against DNA gyrase in vitro compared to novobiocin (nov). Relaxed DNA was incubated with purified DNA gyrase with and without nov and adn.
Figure 14:
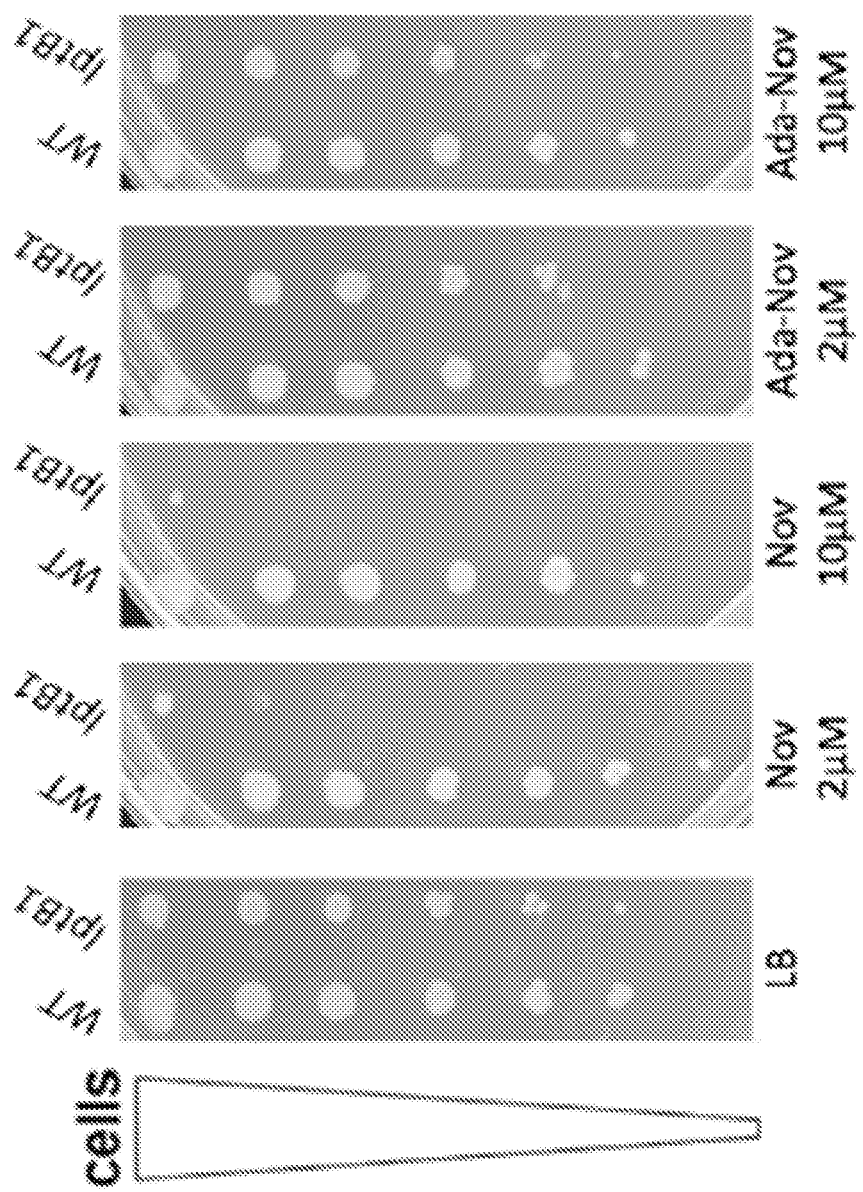
FIG. 14 is a picture of a plating assay showing that novobiocin-adamantyl is less potent than novobiocin against wild type and IptB1 in vivo.
Figure 15:
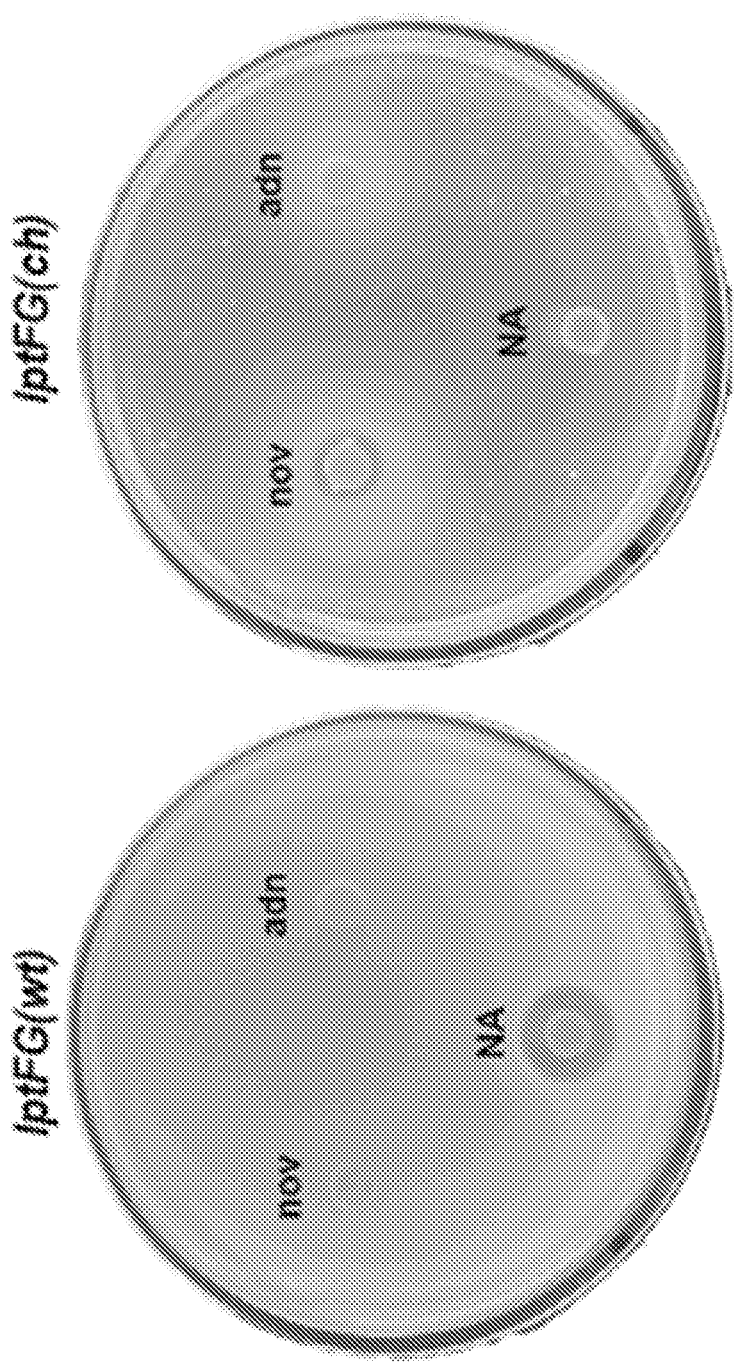
FIG. 15 is a picture of bacterial lawns grown on plates in the presence of disks containing antibiotics. Novobiocin (nov) and novobiocin-adamantyl (adn), but not nalidixic acid (NA), suppressed the lethality of IptFG(ch). Strains were grown overnight in minimal media and then plated on LB plates. Each disk contained 5 μg compound.

We wondered whether it would be possible to separate novobiocin's ability to suppress the lptFG(ch) defects in vivo from its activity against DNA gyrase, its presumed primary target. To test this, we synthesized a carboxamide derivative, novobiocin-adamantyl (FIG. 8A), containing a bulky group that we predicted would impair binding to DNA gyrase, but hoped would not affect binding to LptB. Compared to novobiocin, novobiocin-adamantyl showed reduced activity against DNA gyrase in vitro (FIG. 13) and was ~100× less potent in vivo against the leaky lptB1 strain and an efflux pump-deficient ΔtolC strain (Table 4, FIG. 14). Minimum inhibitory concentrations were measured after a 15-hr incubation period at 37° C. Nevertheless, novobiocin-adamantyl completely suppressed the lethality of lptFG(ch) (FIG. 8B, compare lptFG(ch) between panels, and FIG. 15). We concluded that novobiocin-adamantyl, like novobiocin, interacts directly with LptB. In support of this hypothesis, we obtained a 1.95-Å complex of LptB-ADP-novobiocin-adamantyl that shows that novobiocin-adamantyl binds to the same site as novobiocin (FIG. 8C). These data imply that we can decouple the gyrase and LptB activities of novobiocin.

TABLE 4

Novobiocin-adamantyl is less potent than novobiocin against wild type, lptB1, and efflux pump-deficient ΔtolC strains.

| | Minimum inhibitory concentration (μM) | |
|---|---|---|
| | Novobiocin | Novobiocin-adamantyl |
| wild type | 62.5-125 | >500 |
| lptB1 | <0.5 | 125 |
| ΔtolC | 2 | 125-250 |

Example 5. Tracking LPS Release

Figure 9A:
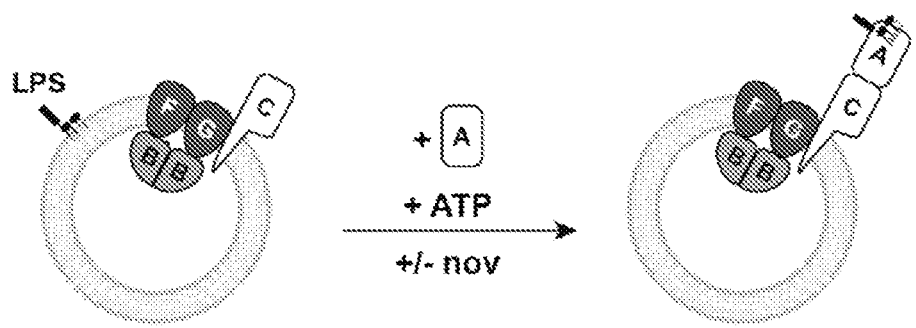
FIG. 9A is a schematic drawing showing the assay to monitor LPS release from right-side-out vesicles to LptA* (LptA(I36pBPA)). Vesicles containing overexpressed wild-type or mutant LptB2FGC complexes were incubated with LptA* and ATP at 30° C. to initiate LPS extraction and transport from the vesicles to LptA*. Samples were taken at different time points and UV-irradiated to crosslink LPS to LptA*, and accumulation of LPS-LptA* adducts was detected using LPS immunoblots.
Figure 9B:
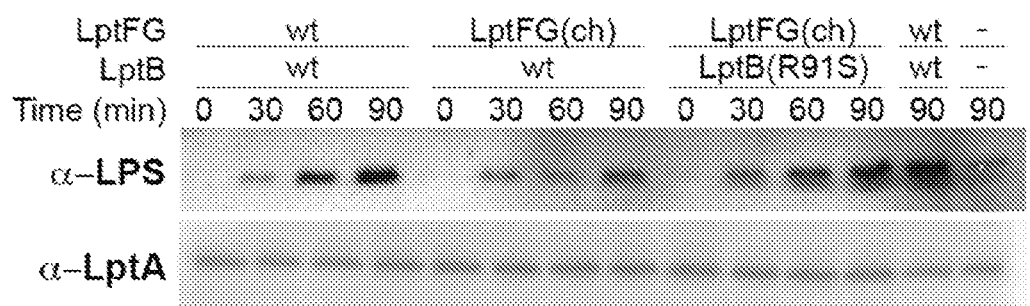
FIG. 9B is a picture of a gel showing that LPS was released from vesicles containing wild-type complexes of LptB2FGC in a time-dependent manner. Complexes containing LptFG(ch) and wild-type LptB released less LPS than fully wild-type complexes; this defect of LptFG(ch) in LPS release was suppressed by LptB(R91 S) in place of wild-type LptB.
Figure 9C:
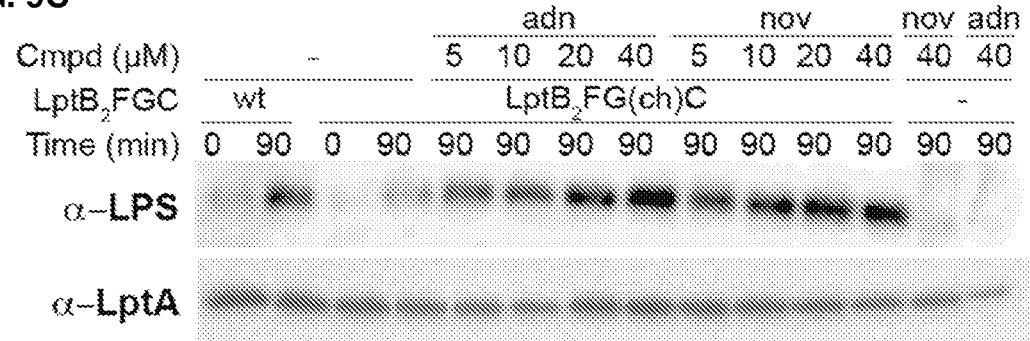
FIG. 9C is a picture of a gel showing that the defect in LPS release seen with complexes containing LptFG(ch) and wild-type LptB was also suppressed by novobiocin or novobiocin-adamantyl. Addition of either agent restored LPS release from vesicles to LptA* in a dose-dependent manner.
Figure 16:
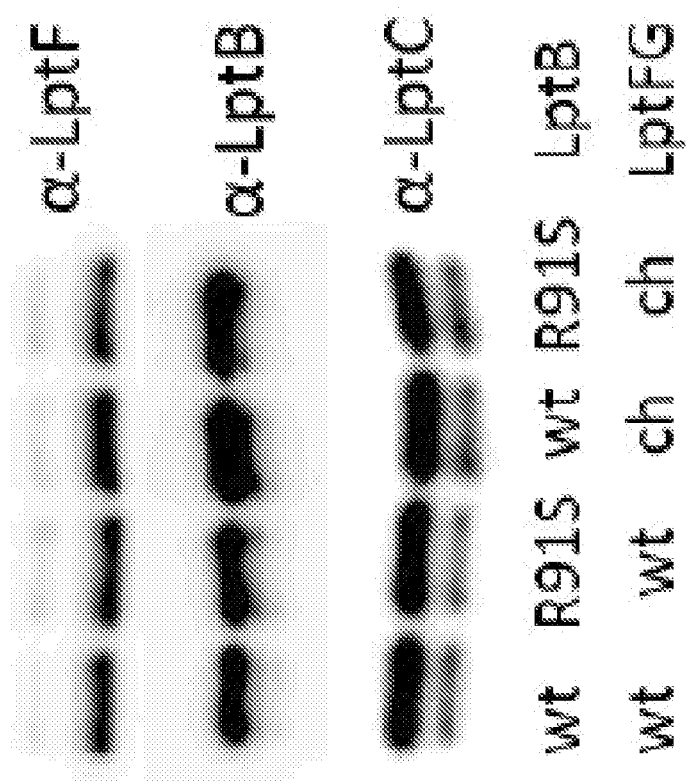
FIG. 16 is a picture of a gel showing that protein levels were consistent across vesicle preparations. Levels of LptB, LptF, and LptC in vesicles were assayed via immunoblot.
Figure 17:
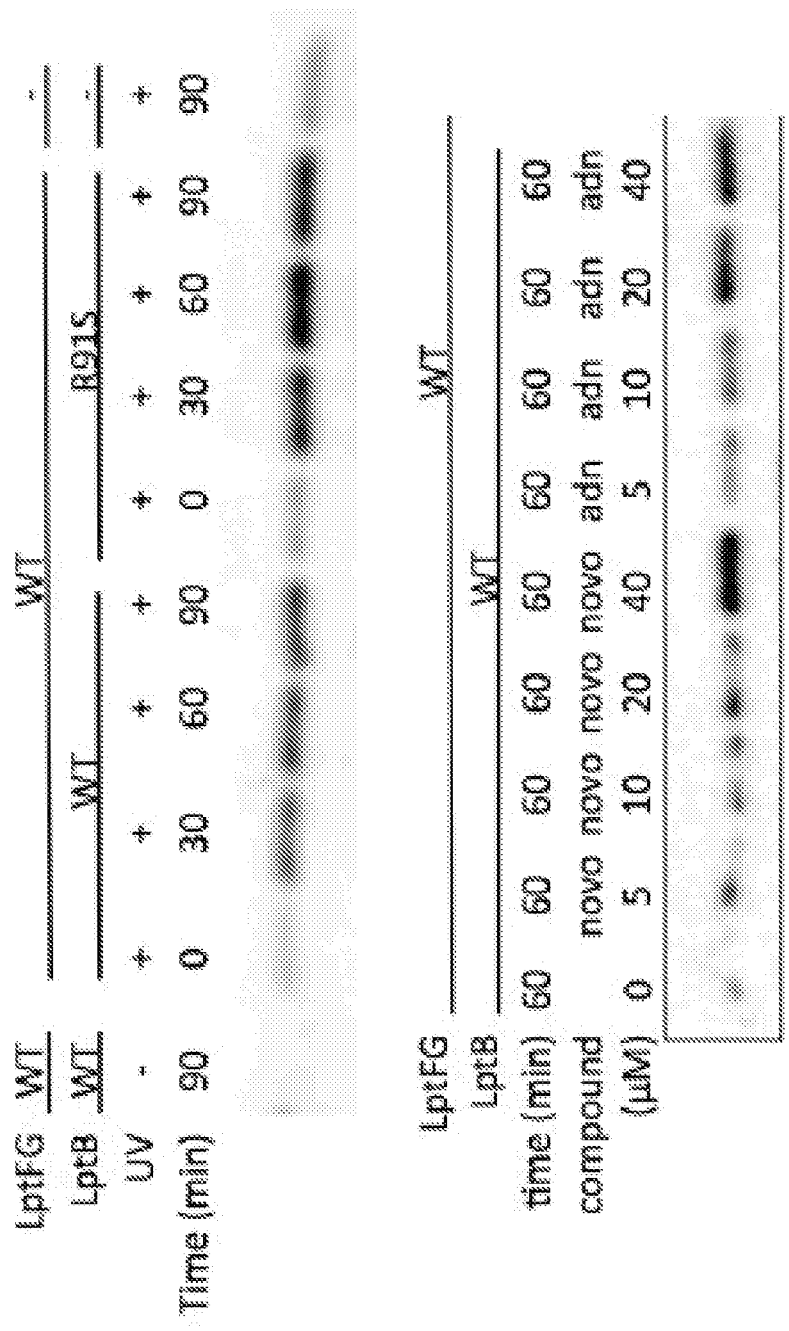
FIG. 17 is a picture of a gel showing the activity of LptB(R91 S) is similar to wild-type LptB in vitro. In the top panel is shown the time-course of LPS release to LptA (I36pBPA) from RSO vesicles containing LptB2FGC with wild-type LptB or LptB(R91 S). Accumulation of the cross-linked LptA-LPS adduct is dependent on overexpression of inner membrane Lpt proteins and UV light. In the bottom panel, novobiocin stimulates LPS release from RSO vesicles containing wild-type LptB inner membrane complexes.

To investigate how lptB(R91S) and novobiocin or novobiocin-adamantyl suppress impaired growth of the lptFG (ch) strain, we used a previously established assay to evaluate time-dependent LPS release from inner membrane vesicles to an LptA variant (LptA*) containing the UV-crosslinkable unnatural amino acid para-benzoyl-phenylalanine (pBPA). The assay detects via immunoblot LPS that becomes crosslinked to LptA* in the presence of UV light. Right-side-out vesicles were made from E. coli cells over-expressing either wild-type or substituted LptB2FGC complexes, soluble LptA* was added, and reactions were incubated with a vehicle control, novobiocin, or novobiocin-adamantyl before being UV irradiated at different time points (FIG. 9A). Protein levels across vesicle preparations were assayed via immunoblot and found to be comparable (FIG. 16). Vesicles containing wild-type complexes of LptB2FGC showed a pronounced time-dependent increase in LPS-LptA* adducts (FIG. 9B, lanes 1-4). By comparison, vesicles containing LptB$_2$LptFG(ch)C complexes released less LPS over time (FIG. 9B, lanes 5-8). These experiments provide direct evidence that the amino acid changes in LptFG(ch), which were known to affect complex formation with LptB, impair LPS release. We found that wild-type levels of LPS release could be restored by preparing vesicles from cells expressing LptB(R91 S) rather than LptB with LptFG(ch)C (lanes 9-12). We also found that novobiocin and novobiocin-adamantyl stimulate LPS release from the LptB$_2$LptFG(ch)C vesicles in a concentration dependent manner (FIG. 9C). These compounds also increase LPS release from vesicles containing wild-type LptB$_2$FGC complexes or LptB(R91 S)2FGC complexes (FIG. 17). Therefore, we conclude that novobiocin and novobiocin-adamantyl rescue lptFG(ch) in vivo by binding LptB and activating LPS release by the inner membrane Lpt components.

Figure 9D:
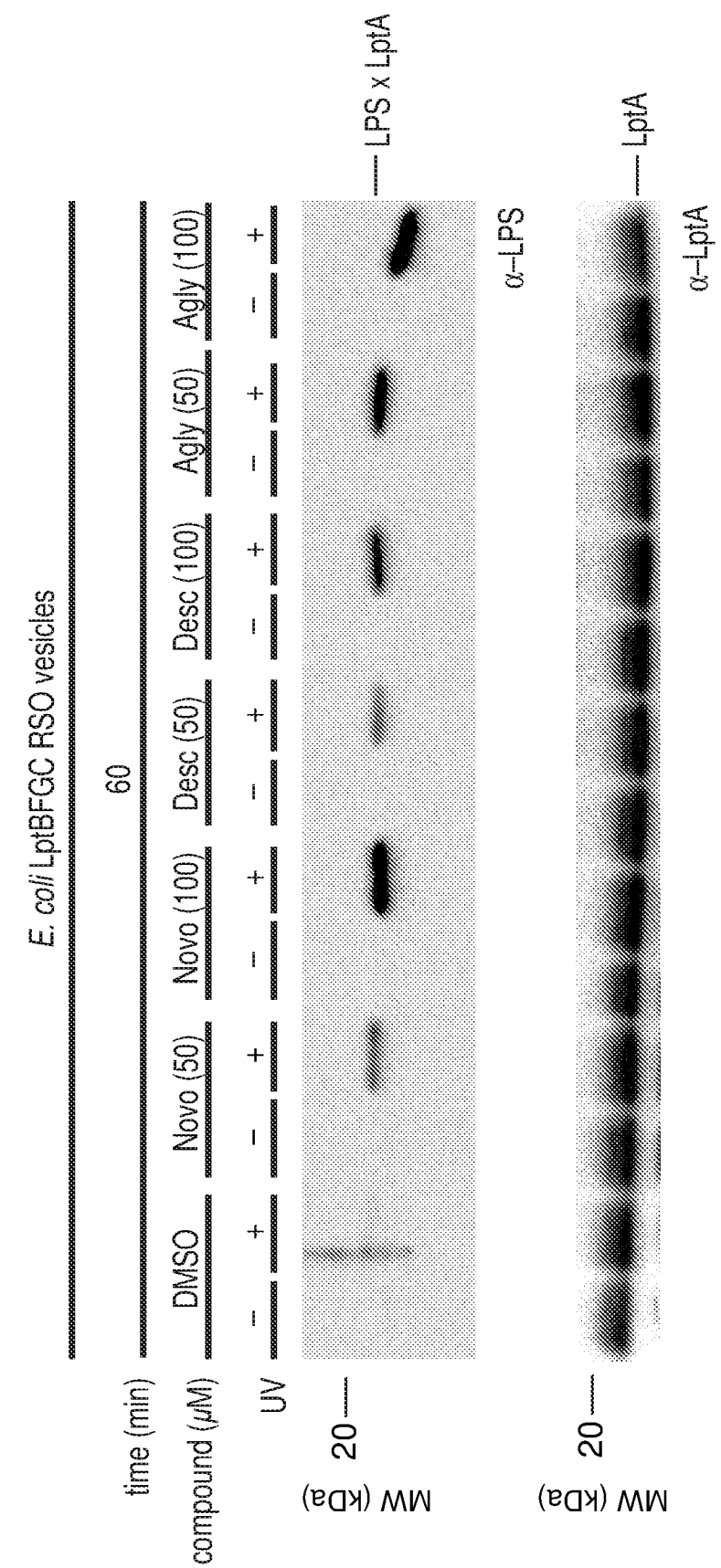
FIG. 9D is a picture of an immunoblot showing that novobiocin and derivatives with impaired gyrase activities stimulate LPS transport in *E. coli* in vitro. Right-side-out vesicles containing overexpressed LptB2FGC were incubated with DMSO, novobiocin (Novo), descarbamyl novobiocin (Desc), or novobiocin aglycone (Agly) at the corresponding concentration and LptA(I36pBPA)His at 30° C. for 1 hour. Samples were UV irradiated at 365 nm for 5 minutes and then quenched with 2X SDS/5% β-mercaptoethanol. Samples were immunoblotted.

FIG. 9D shows right-side-out vesicles containing overexpressed LptBFGC were incubated with DMSO, novobiocin (Novo), descarbamyl novobiocin (Desc), or novobiocin aglycone (Agly) at the corresponding concentrations and LptA(I36pBPA)His at 30° C. for 1 hour. Samples were UV irradiated at 365 nm for 5 minutes and then quenched with 2X SDS/5% β-mercaptoethanol. Samples were immunoblotted. The results indicate that novobiocin and derivatives with impaired gyrase activities stimulate LPS transport in vitro.

Figure 9E:
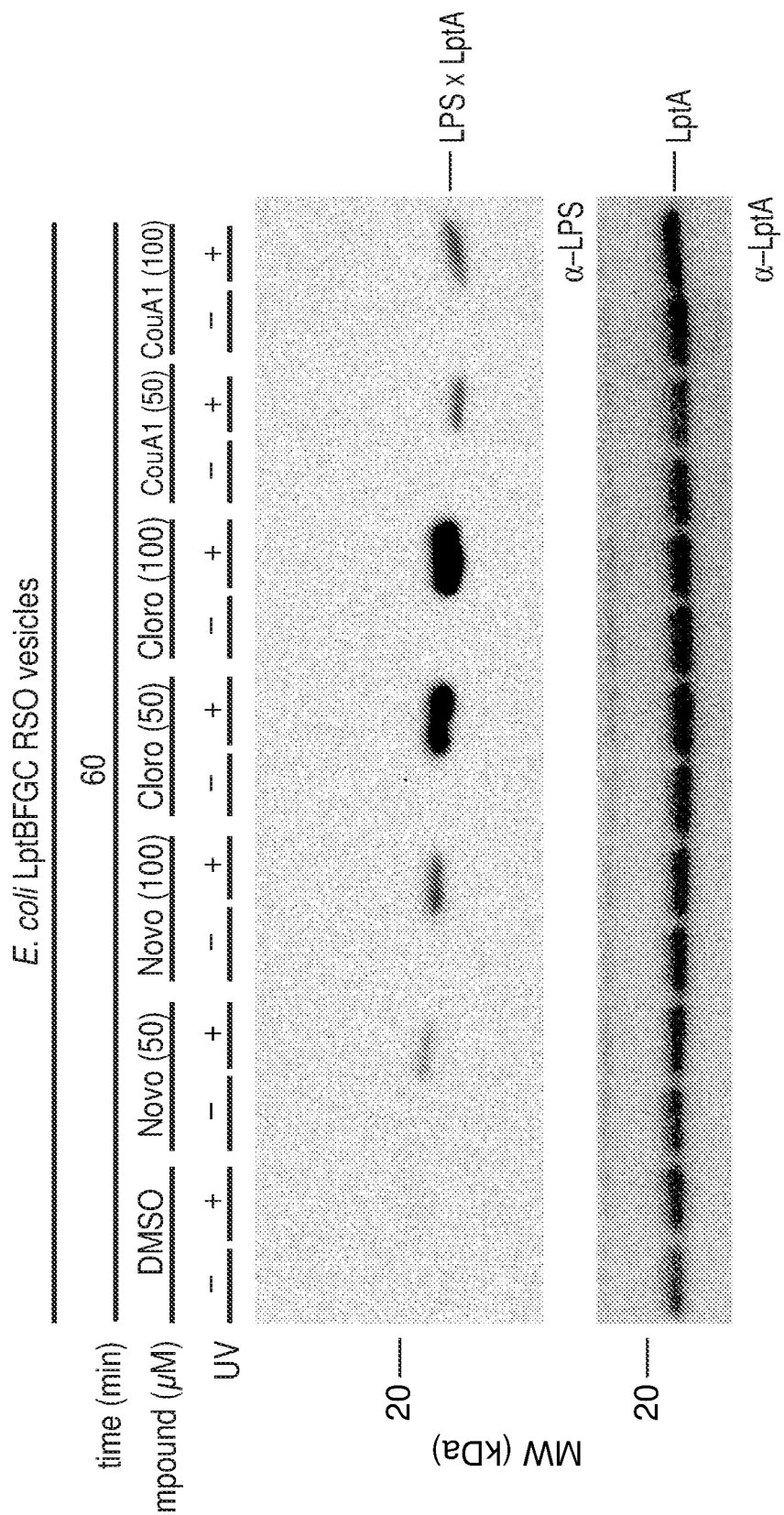
FIG. 9E is a picture of an immunoblot showing that clorobiocin stimulates LPS transport in *E. coli* in vitro. Right-side-out vesicles containing overexpressed LptB$_2$FGC were incubated with DMSO, novobiocin (Novo), clorobiocin (Cloro), or coumermycin A1 (CouA1) and assayed using the same procedure as described for FIG. 9E.
Figure 9F:
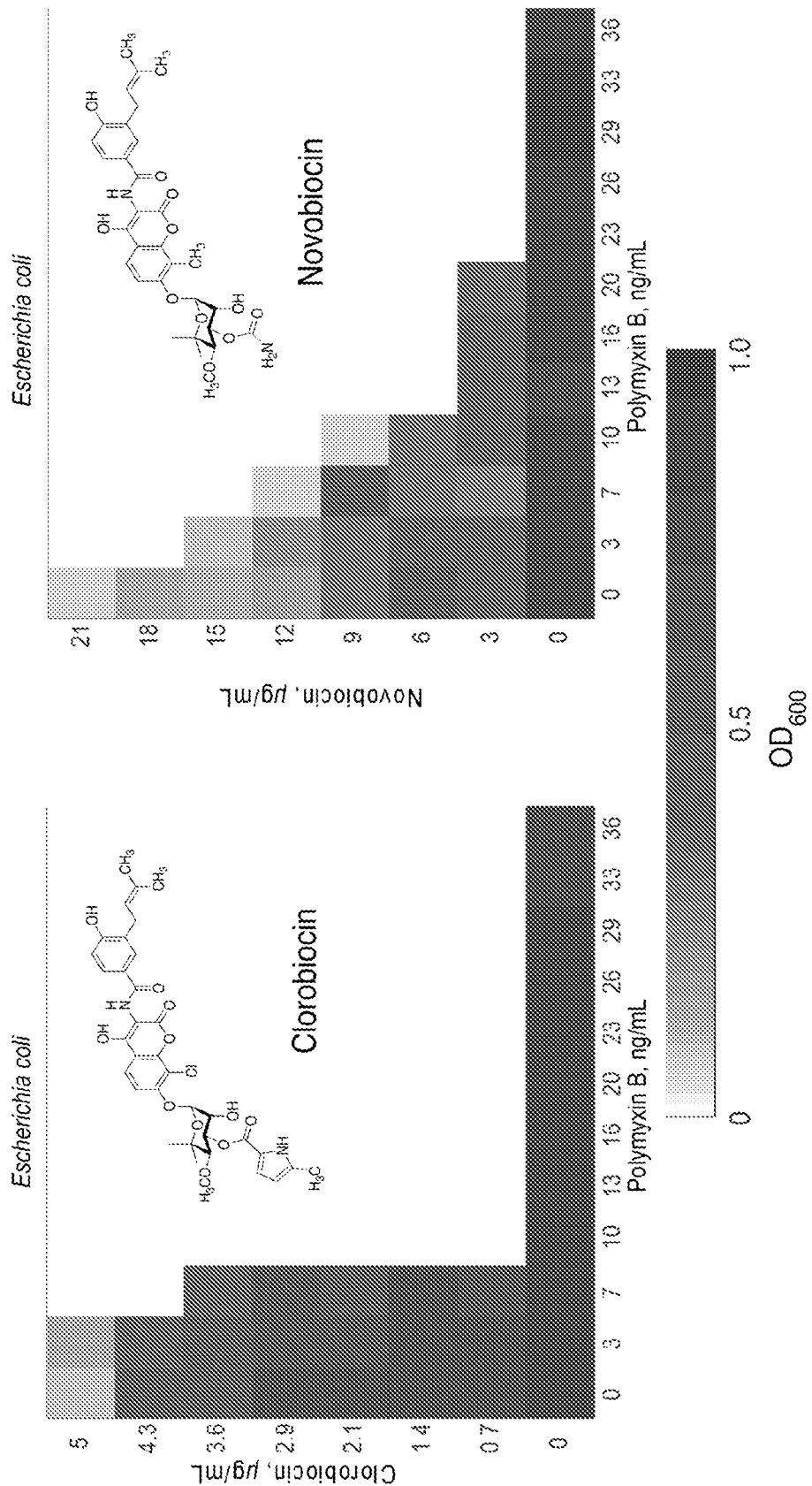
FIG. 9F is a set of graphs of a checkerboard microdilution assay between PMB and clorobiocin (left) and between PMB and novobiocin (right) in wild-type *E. coli* grown at 37° C. for 24, showing that clorobiocin can also synergize with polymyxin B to kill Gram-negative bacteria in vitro.

In FIG. 9E, right-side-out vesicles containing overexpressed LptB$_2$FGC were incubated with DMSO, novobiocin, clorobiocin, or coumermycin A1 and the same procedure was followed. In FIG. 9F, a checkerboard assay was performed which shows that clorobiocin exhibits more potent synergy with PMB than novobiocin. Taken together, the results indicate that clorobiocin highly stimulates LPS transport in vitro and exhibits potent synergy with PMB.

Materials and Methods
Strains

*E. coli* strain Nova Blue [endA1 hsdR17 ($r_{K12}^-$ $m_{K12}^+$) supE44 thi-1 recA1 gyrA96 relA1 lac F'[proA+B+ laclqZΔM15::Tn10] (Tet$^R$)] from Novagen was used for plasmid manipulations. *E. coli* strain KRX [F', traD36, ΔompP, proA+B+, laclq, Δ(lacZ)M15] ΔompT, endA1, recA1, gyrA96 (Nalr), thi-1, hsdR17 ($r_K^-$, $m_K^+$), e14- (McrA-), relA1, supE44, Δ(lac-proAB), Δ(rhaBAD)::T7 RNA polymerase] from Promega was used for protein purification. *E. coli* strain BL-21(λDE3) [F-ompT gal dcm lon hsdSB(rB-, mB-) λ(DE3)] from Novagen was used for right-side-out vesicle preparation. Other strains used in this study are listed in Table 5.

TABLE 5

Strains used in this study.

| Name | Description |
|---|---|
| NR754 | MC4100 ara* |
| NR1250 | NR754 ΔtolC::frt |
| NR1768 | NR754 lptB1-kan |
| NR1962 | MR754 lptB1/G33C-kan |
| NR1963 | NR754 lptB1/R144H-kan |
| NR2761 | NR754 ΔlptFG::frt (pBAD18LptFG3) |
| NR3327 | NR754 ΔlptFG::frt (pBAD18LptFG3/LptFE84A/LptGE88A) |
| NR3602 | NR754 tet2 lptBR91S |
| NR4127 | NR754 tet2 lptBR91S ΔlptFG::frt (pBAD18LptFG3/LptFE84A/LptGE88A) |

The plasmids used in this study are listed in Table 6. Point mutations in pCDFduet-LptB-LptFG were introduced by site-directed mutagenesis using the oligonucleotides listed in Table 7. PCR amplification was performed with KOD Hot Start DNA polymerase from Novagen. Restriction enzyme DpnI was purchased from New England Biolabs. All other materials were purchased from Sigma Aldrich unless noted otherwise.

TABLE 6

Plasmids used in this study

| Name | Description |
|---|---|
| pET22/42-LptB-His$_g$ | Encodes LptB with a C-terminal His$_g$ tag |
| pBAD/HisA-LptC | Encodes LptC for the RSO vesicle assay |
| pCDFduet-LptB-LptFG | Encodes LptB and LptFG for the RSO vesicle assay |
| pET22b-LptA(I36Am)-His | LptA with amber codon (TAG) for substitution with pBPA |
| pSup-BpaRS-6TRN | Encodes amino-acyl tRNA synthetase as well as tRNAs for incorporation of pBPA at TAG codons |

TABLE 7

Oligonucleotides used in this study

| Name | Sequence (5' to 3') | SEQ ID NO. |
|---|---|---|
| LptF_E84A_f | ggc aaa ctg tat acc gaa agt gcg att acg gta atg cat gcc tgc ggc c | SEQ ID NO. 1 |
| LptF_E84A_r | ggc cgc agg cat gca tta ccg taa tcg cac ttt cgg tat aca gtt tgc c | SEQ ID NO. 2 |
| LptG_E88A_f | ggg atg ctg gcg cag cgc agc gcg ctg gtg gtg atg cag gct tct gg | SEQ ID NO. 3 |
| LptG_E88A_r | cca gaa gcc tgc atc acc acc agc gcg ctg cgc tgc gcc agc atc cc | SEQ ID NO. 4 |
| LptB_R91S_f | ctg cca cag gaa gcc tcc att ttc agc cgc ctc agc gtt tac gat aac ctg | SEQ ID NO. 5 |

TABLE 7-continued

Oligonucleotides used in this study

| Name | Sequence (5' to 3') | SEQ ID NO. |
|---|---|---|
| LptB_R91S_f | cag gtt atc gta aac gct gag gcg gct gaa aat gga ggc ttc ctg tgg cag | SEQ ID NO. 6 |

Disk Diffusion Assay

Disk diffusion assays were performed as described in Sherman et al., Proc. Natl. Acad. Sci. USA 2014, 111, 4982-4987. Premade Sensi-Disc (BD-Beckton, Dickinson and Company) were used for bacitracin 10IU, erythromycin 15 µg, novobiocin 30 µg, and rifampin 5 µg. When needed, 5 µg disks of nalidixic acid, novobiocin, and novobiocin-adamantyl were prepared by soaking into sterile 7 mm disks hole-punched from Whatman grade:17chr chromatography paper.

Efficiency of Plating Assay

Efficiency of plating assays were performed on indicated media using the method described in Butler et al., J. Bacteriol. 2013, 195, 4639-4649.

LptB-his Overexpression and Purification for Crystallography

LptB-His (full-length LptB with a C-terminal His8 tag) was purified as described in (Sherman et al., Proc. Natl. Acad. Sci. USA 2014, 111, 4982-4987) with minor modifications. Overnight cultures of KRX cells (Promega) transformed with plasmid pET22/42-LptB-His8 were diluted 100× into LB Miller media containing 50 µg/mL carbenicillin. Cultures were grown at 37° C., 220 rpm to OD 0.8, at which point the temperature was reduced to 16° C. Following 30 min of shaking at 16° C., overexpression was induced with 0.2% L-rhamnose monohydrate. Cultures were grown at 16° C., 220 rpm for 14 h.

Cells were harvested by centrifugation at 5000×g, 4° C. for 20 min. Pellet was resuspended in Buffer A: Tris-buffered saline (TBS; 20 mM Tris [pH 8.0], 150 mM NaCl), 20% (vol/vol) glycerol, and 0.5 mM Tris(3-hydroxypropyl) phosphine (THP: EMD Milipore). To facilitate lysis, 0.5 mM phenylmethylsulfonyl fluoride (PMSF), 50 µg/mL lysozyme, and 50 µg/mL DNAse I were added to the cell suspension. Cells were lysed 3× through a high-pressure cell disruptor. Unbroken cells were removed by centrifugation at 6000×g, 4° C. for 10 min. To pellet membranes, cell lysate was centrifuged at 100,000×g, 4° C. for 30 min. Membranes were discarded and 10 mM imidazole was added to the supernatant.

In preparation for nickel affinity chromatography, Ni-NTA Superflow resin (Qiagen) was washed with water and equilibrated with Buffer A supplemented with 10 mM imidazole. Cell lysate supernatant was incubated with equilibrated Ni-NTA resin at 4° C. for 1 h with gentle rocking. Following incubation, flow-through was removed and resin was washed with 20 column volumes of Buffer A with 20 mM imidazole. Protein was eluted in one batch with 2.7 column volumes of Buffer A with 200 mM imidazole. Eluate was concentrated in a 10-kDa molecular weight cutoff (MWCO) centrifugation filter (Amicon; Millipore) to ~50 mg/mL and flash frozen.

Protein was further purified by size exclusion chromatography on Superdex 200 10/30 GL column in Buffer A. Fractions containing protein were pooled and concentrated in a 10-kDA MWCO centrifugation filter to ~50 mg/mL. Protein aliquots were flash-frozen and stored at −80° C. Protein concentration was measured using the Biorad DC protein assay.

LptB-his Crystallization and Novobiocin Soak

LptB-His was crystallized using conditions described in Sherman et al., Proc. Natl. Acad. Sci. USA 2014, 111, 4982-4987. Purified LptB-His was diluted into Buffer A to a concentration of 20 mg/mL. The 20 mg/mL stock was diluted 2× into TBS, yielding a final protein concentration of 10 mg/mL and glycerol concentration of 10%. This solution was incubated with 2.5 mM ATP and 2.5 mM $MgCl_2$ for 1 h on ice before setting up drops.

Crystals were grown by vapor diffusion in hanging drops at room temperature. 1 µL protein solution was mixed with 1 µL reservoir solution consisting of 100 mM MES (pH 6.5) and 30% (wt/vol) PEG 4000. As observed in (Sherman et al., Proc. Natl. Acad. Sci. USA 2014, 111, 4982-4987), flat, triangular crystals appeared after several days.

For the novobiocin soaks, crystals were transferred to 2-µL drops of reservoir solution (100 mM MES (pH 6.5), 30% PEG 4000) containing 2.5 mM novobiocin sodium salt. Crystals were soaked for ~90 min at room temperature and then flash-frozen in cryoprotectant containing 100 mM MES (pH 6.5), 33% PEG 4000, 24% glycerol, and 2.5 mM novobiocin.

LptB-his Co-Crystallization with Novobiocin-Adamantyl

LptB-His was crystallized using conditions described above. The 20 mg/mL stock was diluted 2× into TBS, yielding a final protein concentration of 10 mg/mL and glycerol concentration of 10%. This solution was incubated with 2.5 mM ATP, 2.5 mM $MgCl_2$ for 1 h on ice before setting up drops.

Crystals were grown by vapor diffusion in hanging drops at room temperature. 1 µL protein solution was mixed with 1 µL reservoir solution consisting of 100 mM MES (pH 6.5), 30% (wt/vol) PEG 4000, and 1.3 mM novobiocin-adamantyl solution (final droplet [DMSO]=7%). As observed in (Sherman et al., Proc. Natl. Acad. Sci. USA 2014, 111, 4982-4987), flat, triangular crystals appeared after several days. Crystals were flash-frozen in cryoprotectant containing 100 mM MES (pH 6.5), 33% PEG 4000, 24% glycerol, and 2.5 mM novobiocin-adamantyl.

Crystallography Data Collection

The X-ray diffraction data for the LptB-ADP-NOV and LptB-ADP-ADN crystals were collected at 0.97918 Å at beamline 24-ID-E of the Advanced Photon Source at Argonne National Laboratory. LptB-ADP-NOV and LptBADP-ADN belong to the space group C121 (Table 8).

Crystallography Data Processing and Structure Determination

The LptB-ADP-NOV dataset was indexed and integrated using iMosflm and scaled using the CCP4 program AIMLESS. The structure was solved by molecular replacement with Phaser using the complete LptB-ADP structure from (Sherman et al., Proc. Natl. Acad. Sci. USA 2014, 111, 4982-4987) as a search model (PDB: 4P32). Initial rounds of refinement in Phenix were performed with rigid body refinement, simulated annealing, and ADP (atomic displacement parameter or B-factor) refinement, yielding a model with $R_{free}$ and $R_{work}$ values of 29.9% and 25.0%, respectively. This model contained clear unassigned density at the LptB dimer interface.

Following manual placement of novobiocin into the unassigned density in COOT, the model was further refined in Phenix with cycles of minimization, simulated annealing, and ADP refinement, interspersed with manual editing in COOT. Waters and magnesium ions were placed, and the refinement was completed using cycles of minimization, ADP refinement, and translation/libration/screw (TLS) refinement with TLS parameters from the TLS motion determination server. Ligand restraints were generated using the Mogul geometry optimization in eLBOW, and coordination sphere restraints were generated with ReadySet. The $R_{free}$ and $R_{work}$ values for the final LptB-ADP-NOV structure are 22.0% and 17.9%, respectively.

The LptB-ADP-ADN dataset was processed with the same procedure as the LptB-ADP-NOV dataset, except that an adamantyl group was modeled in to fit the electron density. The $R_{free}$ and $R_{work}$ values for the final LptB-ADPADN structure are 22.4% and 18.0%, respectively.

Much of the software used in this project was installed and configured by SBGrid. Figures were prepared using Pymol.

shake at 220 rpm, 37° C. overnight. 15 μL of overnight culture was diluted in 15 mL of LB Miller in a Falcon tube and was vortexed to mix. In a 96-well plate, 100 μL of diluted culture was added to each well. To column #1, an additional 100 μL of diluted culture and test compound was added (93.7 μL culture+6.35 μL 10 mg/mL novobiocin) or (94.2 μL culture+5.87 μL 10 mg/mL 1-adamantyl-novobiocin) such that the highest concentration tested was 500 μM. Transferred 100 μL from column #1 into column #2, etc, and mixed each time thoroughly. Repeated serial dilution until column #11. Incubated the plate at 37° C. overnight (~16 h) and read the turbidity ($OD_{600}$) using a Spectramax 384 plus plate reader (Molecular Devices). The minimum inhibitory concentration (MIC) was defined as the lowest concentration of compound needed to completely inhibit bacterial growth.

Gyrase Activity Assay

The *Escherichia coli* gyrase supercoiling inhibition assay kit was purchased from the Inspiralis company (Norwich, UK). The assay was conducted according to the provided instructions. 1 U of DNA gyrase was incubated with 0.5 μg of relaxed pBR322, and the stated compound concentration, in a reaction volume of 30 μL at 37° C. for 30 minutes in Assay Buffer (35 mM Tris-HCl, pH 7.5; 24 mM KCl; 4 mM $MgCl_2$, 2 mM DTT, 1.8 mM spermidine, 1 mM ATP, 6.5% (w/v) glycerol, 0.1 mg/mL albumin). The supercoiling reac-

TABLE 8

Data collection and refinement statistics

| Data Set | LptB-ADP-NOV | LptB-ADP-ADN |
|---|---|---|
| Space group | C121 | C121 |
| | Unit cell | |
| Dimensions (a, b, c), Å | 190.32, 35.10, 63.05 | 104.03, 34.78, 62.71 |
| Angles (α, β, γ), ² | 90.00, 91.52, 90.00 | 90.00, 101.38, 90.00 |
| | Data collection* | |
| Wavelength, Å | 0.97918 | 0.97918 |
| Resolution range, Å | 63.03-2.00 (2.05-2.00) | 43.71-1.95 (2.02-1.95) |
| $R_{merge}$ | 0.128 (0.622) | 0.068 (0.587) |
| Completeness, % | 99.4 (99.2) | 99.2 (98.9) |
| Mean I/σ(I) | 8.7 (2.1) | 9.56 (1.95) |
| Unique reflections | 28,483 | 16,230 |
| Multiplicity | 3.5 (3.5) | 1.9 (1.9) |
| | Refinement* | |
| $R_{work}$ %/$R_{free}$ % | 17.94/22.03 | 18.01/22.36 |
| No. of LptB molecules per asymmetrical unit | 2 | 1 |
| No. of modeled LptB residues per chain | 234 (A)/226 (B) | 233 (A) |
| No. of water molecules | 101 | 105 |
| No. of ions | 2 | 1 |
| | Average B-factor, Å² | |
| Protein | 20.61 | 33.98 |
| Ligands | 18.26 | 43.42 |
| Solvent | 17.76 | 37.10 |
| | Ramachandran plot | |
| Favored, % | 98.9 | 98.27 |
| Disallowed, % | 0 | 0 |
| | rmsd from ideal geometry | |
| Bond lengths, Å | 0.007 | 0.004 |
| Bond angles, ° | 0.747 | 0.72 |

*Values in parentheses are for the shell with the highest resolution.

Minimum Inhibitory Concentration Assay

Overnight cultures were prepared by transferring 5 mL of sterile LB Miller media to culture tubes and inoculating with the corresponding organism. The tubes were allowed to tions were quenched by the addition of 30 μL of STEB buffer (40% (w/v) sucrose, 100 mM Tris.HCl pH 8, 10 mM EDTA, 0.5 mg/mL bromophenol blue) and 30 μL of chloroform/isoamyl alcohol (v/v, 24:1). Samples were vortexed for 5 minutes and centrifuged at max speed for 1 minute. 20 μL of the upper aqueous layer were loaded on a 1% (w/v) agarose gel free of DNA intercalator and run at 85 V for 2 h. The gel was then stained with DNA intercalator and visualized with an Azure imaging system.

Right-Side-Out Vesicle Preparation

Right-side-out (RSO) vesicles were prepared as described in (Okuda et al. *Science* 2012, 338, 1214-1217) with minor modifications. BL-21(λDE3) *E. coli* were transformed with plasmid pBAD18HisA-LptC along with one of pCDFduet (empty vector), pCDFduet-LptB-LptFG (encoding wild-type *E. coli* proteins), pCDFduet-LptB-LptFG(ch) (encoding wild-type LptB and LptF(E84A)LptG(E88A)) or pCDFduet-LptB(R91 S)-LptFG. Overnight cultures were diluted 1:100 into 50 mL of LB Miller media containing 50 μg/mL carbenicillin and 50 μg/mL spectinomycin and grown at 24° C. to $OD_{600}$~1. Growth temperature was then increased to 37° C. and expression induced by addition of 0.02% arabinose and 10 μM Isopropyl β-D-1-thiogalactopyranoside (IPTG). After two hours, cells were pelleted, resuspended in 5 mL 50 mM Tris-HCl (pH 7.4) 250 mM sucrose, 300 μg/mL lysozyme and 150 μg/mL DNaseI, and converted to spheroplasts by dropwise addition of 5 mL buffer containing 50 mM Tris-HCl (pH 7.4), 250 mM sucrose and 3 mM EDTA followed by incubation on ice for 30 minutes.

To convert spheroplasts to RSO-vesicles, spheroplasts were pelleted, 6000 g×10 minutes, resuspended in 5 mL lysis buffer (20 mM Tris (pH 8), 150 mM NaCl, 0.1 mM EDTA, 5 mM $MgCl_2$, and 5 mM sodium-ATP (pH ~7)), pelleted at 10,000 g×15 minutes, and resuspended in the supernatant to complete lysis. RSO-vesicles were collected by centrifugation at 200,000 g×30 minutes and resuspended in 1 mL of 10% v/v glycerol, 20 mM Tris (pH 8.0), 150 mM NaCl, 5 mM $MgCl_2$, and 5 mM sodium-ATP (pH ~7). Total protein concentration in RSO-vesicle samples was determined by DC-protein assay (BioRad), and samples were either used immediately in LPS release assays or flash-frozen and stored at –80° C.

Purification of LptA* (LptA(I36pBPA))

LptA* was purified as described in (Okuda et al. *Science* 2012, 338, 1214-1217) with minor modifications. BL-21 (λDE3) *E. coli* containing pSup-BpaRS-6TRN and pET22b-LptA(I36Am) were grown to $OD_{600}$~0.6 at 37° C. in 1.5 L LB Miller media containing 50 μg/mL carbenicillin, 30 μg/mL chloramphenicol and 0.7 mM para-benzoylphenylalanine (pBPA, BaChem), and induced for 2 hours with 50 μM IPTG. These cells were pelleted, converted to spheroplasts as described above, and the spheroplasts pelleted at 6000 g×10 minutes. Supernatant from the spheroplasts was collected and supplemented with 1 mM PMSF and 10 mM imidazole, and clarified by ultracentrifugation at 100,000 g×30 minutes. Supernatant was applied twice to Ni-NTA resin, washed with 2×20 column volumes of wash buffer (20 mM Tris (pH 8.0), 150 mM NaCl, 10% v/v glycerol) with 20 mM imidazole, and eluted with 2×2.5 column volumes of wash buffer with 200 mM imidazole. Eluate was concentrated to ~1 mg/mL using an Amicon 10 kDa cut-off Amicon centrifugal filter (Millipore), aliquoted, and stored at –80° C.

LPS-Release Assay

The in vitro LPS-transport experiments in FIGS. 9B, 9C, and 17 were set-up as described in (Okuda et al. *Science* 2012, 338, 1214-1217) with some modifications. RSO-vesicles (50 μg total protein) were diluted into 100 μL reaction buffer (10% v/v glycerol, 20 mM Tris (pH 8.0), 150 mM NaCl, 5 mM sodium-ATP, 5 mM $MgCl_2$), and incubated on ice with novobiocin, 1-adamantyl-novobiocin, or no compound for 15 minutes (50× compound stocks in water were used for each concentration). To start the assay, 3 μg of LptA* was added to each sample, with each time-point its own 100 μL sample, and samples were then incubated at 30° C. for the stated time. To cross-link LptA* to LPS, samples were transferred to a 96-well plate and irradiated with 365 nm UV-light for 5 minutes. Cross-linked samples were then mixed 1:1 with 2× SDS loading dye (100 mM Tris-HCl pH 6.8, 4% w/v SDS, 0.05% w/v bromothymol blue, 20% glycerol) with 5% β-mercaptoethanol, and boiled for 10 minutes.

Immunoblotting was used to assess LptA*-LPS levels in each sample. Boiled samples were run on home-made 4%/15% polyacrylamide stacking gels at 0.02 A constant-current until the 15 kDa ladder band (BioRad Precision Plus all Blue standards) had run out of the gel, transferred to PVDF, and immunoblotted with mouse anti-LPS core antiserum (HyCult Biotechnology) followed by sheep-anti-mouse IgG horseradish peroxidase conjugate (GE Healthcare). LptA levels were assessed similarly, using rabbit anti-LptA antiserum followed by donkey anti-rabbit horseradish peroxidase conjugate (GE Amersham). ECL Prime Western Blotting Detection Reagent (GE Amersham) was used to visualize antibody-label bands in conjunction with an Azure c400 imaging system (Azure Biosystems).

To assess the expression levels of inner-membrane Lpt components in the different RSO preparations, samples from LPS release assays were also individual to SDS-PAGE and immunoblotting as described above. Rabbit anti-LptC, rabbit anti-LptF, or rabbit anti-LptB antisera were used to label Lpt proteins on PVDF and in turn detected and imaged as described for LptA.

Fbn-LptB Binding Assay 5 mL of the buffered Fbn ligand solution was prepared by mixing 200 μL of 25× TBS pH 8.0, 125 μL 200 mM ADP pH 7.0, 125 μL 200 mM $MgCl_2$, 4.43 μL of 56.5 mM Fbn, 4.55 mL of D20. Final [Tris-Cl]=50 mM, [NaCl]=150 mM, [ADP]=5 mM, $[MgCl_2]$=5 mM, [Fbn]=50 μM. In ten 1.5 mL Eppendorf tubes, on ice, the corresponding volume of stock LptB-His protein was added to the buffered Fbn solution. The tubes were vortexed briefly, the solutions transferred to Bruker Biospin 5.0×103.5 mm NMR tubes (for SampleJet) and stored at +4° C. until acquisition. Data were acquired using a Bruker 500 MHz Avance III with multi-nuclear smart probe operating at a frequency of 470.5453180 MHz for $^{19}F$ and 500.1320005 MHz for $^1H$. A standard fluorine 1D pulse program with proton decoupling was used; temperature (T)=298.1 K, number of scans (NS)=3072, relaxation delay (D1)=0.75 s, pulse angle=70°. After acquisition, FIDs were Fourier transformed, phased, and processed with the exponential multiplication window function (LB=3.00 Hz) in MestReNova MNova v10. The $^{19}F$ linewidths were plotted against log [LptB] in GraphPad Prism 7 software using the nonlinear fit log(agonist) vs. response model, variable slope (four parameters).

General Synthetic Methods

Unless otherwise noted, all reactions were performed under anhydrous $N_2$. Solvents were purchased in Sure-Seal bottles from Sigma-Aldrich and used without further purification. Thin layer chromatography (TLC) was carried out using EM Science silica gel 60 F254 plates; the developed plate was analyzed by UV lamp (254 nm). Column chromatography was performed with the Teledyne-Isco Combi-Flash Rf 200 system using pre-packed silica gel column cartridges and hexanes/ethyl acetate or dichloromethane/methanol as the solvent system. $^1H$ NMR and $^{13}C$ NMR spectra were recorded in DMSO-d6 or $CDCl_3$ on a Varian Inova-500 MHz spectrometer unless otherwise noted.

Chemical shifts are reported in ppm with the residual solvent signal as the reference, and coupling constants (J) are given in hertz. The peak information is described as: br=broad singlet, s=singlet, d=doublet, t=triplet, q=quartet, m=multiplet. High-resolution mass spectra (HRMS) were performed on a Bruker microTOFII ESI LCMS system mass spectrometer using sodium formate as the standard. Novenamine and N-acylated derivatives were obtained by existing literature methods (Gunaherath et al., *Bioorg. Med. Chem.* 2013, 21, 5118-5129).

Synthesis of Novobiocin-Adamantyl (adn)

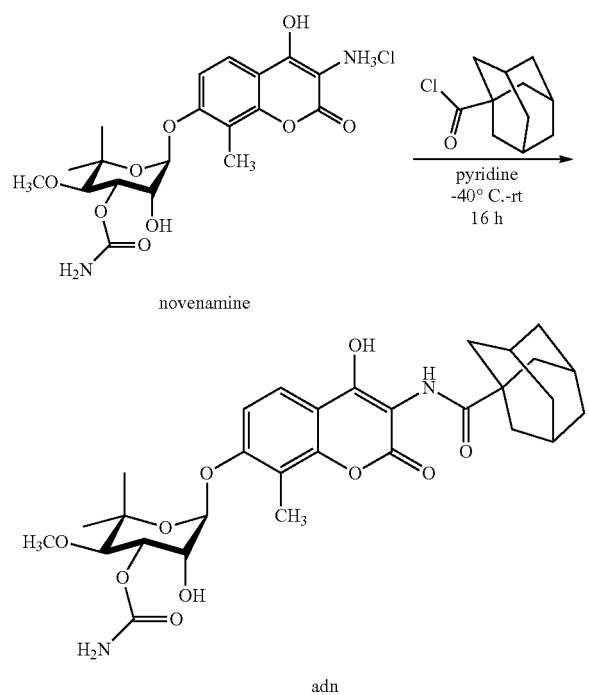

Novenamine hydrochloride (40 mg, 0.09 mmol, 1.0 eq.) and a magnetic stirbar were added to a 25 mL conical flask and sealed with a rubber septum. A vent needle was inserted and the flask was sparged with $N_2$ for 5 minutes (free novenamine begins to oxidize upon exposure to O2!). 2 mL of pyridine were added under positive $N_2$ pressure and the flask was cooled to −40° C. in a dry ice/acetonitrile bath. 1-adamantanecarbonyl chloride (17.2 mg, 0.09 mmol, 1.0 eq.) was dissolved in 0.5 mL of pyridine and added to the stirring novenamine solution. The solution was stirred for 16 h while allowing the bath to warm to room temperature. The reaction mixture was concentrated by rotary evaporation and then subjected to flash column chromatography with DCM/MeOH (10 mg, 16% isolated yield). The product was further purified by reversed-phase column chromatography with a Zorbax C18 column with acetonitrile/water as the eluent (90% MeCN to 100% MeCN over the course of 15 minutes), and the final product was obtained as a white solid (6.7 mg, 13% isolated yield).

Synthesis of Fluorobiocin (fbn)

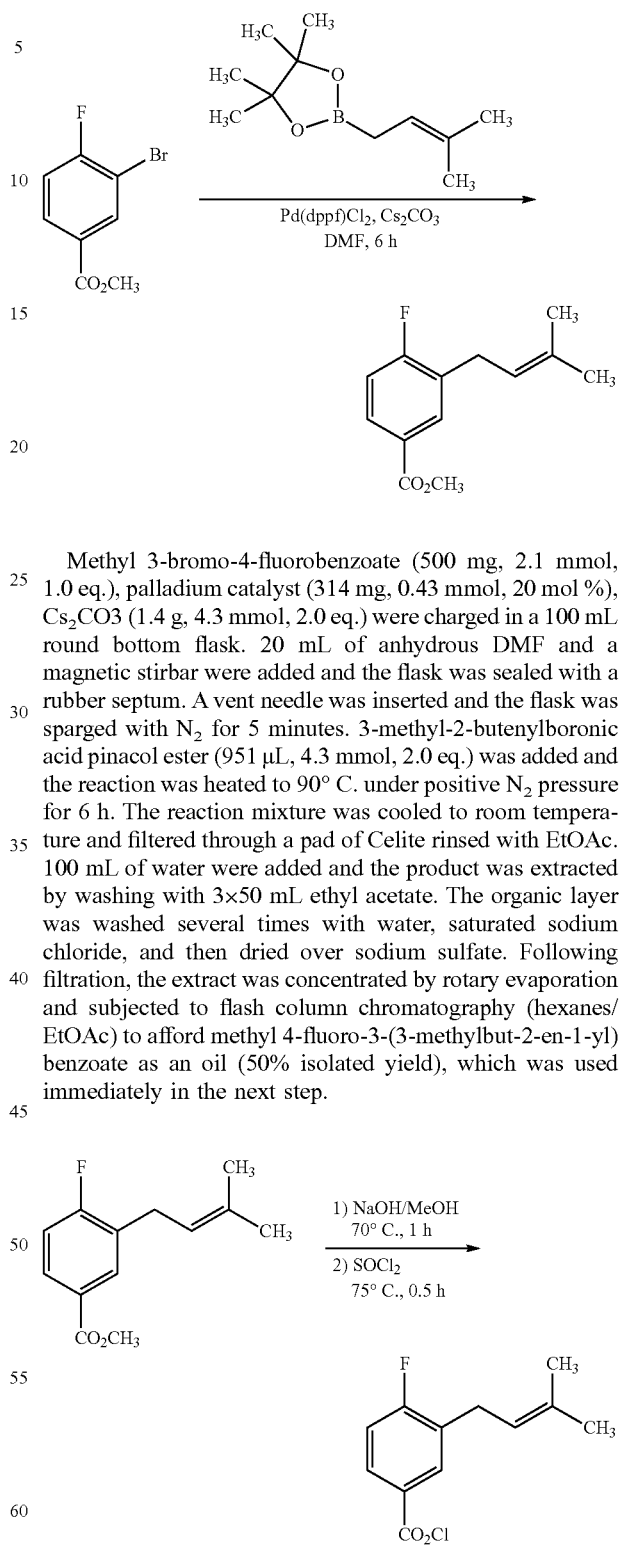

Methyl 3-bromo-4-fluorobenzoate (500 mg, 2.1 mmol, 1.0 eq.), palladium catalyst (314 mg, 0.43 mmol, 20 mol %), $Cs_2CO3$ (1.4 g, 4.3 mmol, 2.0 eq.) were charged in a 100 mL round bottom flask. 20 mL of anhydrous DMF and a magnetic stirbar were added and the flask was sealed with a rubber septum. A vent needle was inserted and the flask was sparged with $N_2$ for 5 minutes. 3-methyl-2-butenylboronic acid pinacol ester (951 μL, 4.3 mmol, 2.0 eq.) was added and the reaction was heated to 90° C. under positive $N_2$ pressure for 6 h. The reaction mixture was cooled to room temperature and filtered through a pad of Celite rinsed with EtOAc. 100 mL of water were added and the product was extracted by washing with 3×50 mL ethyl acetate. The organic layer was washed several times with water, saturated sodium chloride, and then dried over sodium sulfate. Following filtration, the extract was concentrated by rotary evaporation and subjected to flash column chromatography (hexanes/EtOAc) to afford methyl 4-fluoro-3-(3-methylbut-2-en-1-yl)benzoate as an oil (50% isolated yield), which was used immediately in the next step.

Methyl 4-fluoro-3-(3-methylbut-2-en-1-yl)benzoate (220 mg, 1 mmol) was added to a 15 mL scintillation vial equipped with a magnetic stirbar. 2 mL of 1M NaOH in methanol and a few drops of water were added to the vial.

The reaction was heated to 70° C. for 1 h. The carboxylate product precipitated upon completion of the reaction, and the mixture was concentrated by rotary evaporation. The carboxylate salt was protonated by the dropwise addition of 1M HCl. Ethyl acetate (5 mL) and water (5 mL) were added and the acid product was extracted from the organic layer. The extract was dried over sodium sulfate, filtered, and concentrated by rotary evaporation. The carboxylic acid product was a white solid and was used without further purification. Thionyl chloride (700 μL, 14 eq.) was added and the mixture was heated to 75° C. for 0.5 h. The leftover thionyl chloride was removed by rotary evaporation and 150 mg of a sticky orange gel (88% isolated yield).

Characterization and NMR Spectra

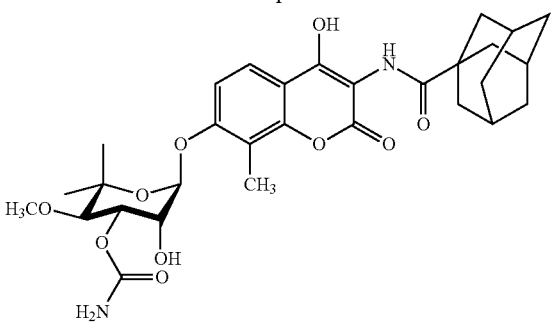

1-adamantyl-novobiocin (adn)
(3R,4S,5R,6R)-6-((3-((3R,5S)-adamantane-1-carboxamido)-4-hydroxy-8-methyl-2-oxo-2H-chromen-7-yl)oxy)-

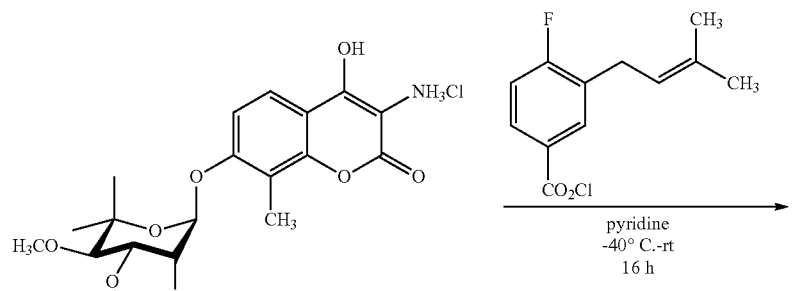

novenamine

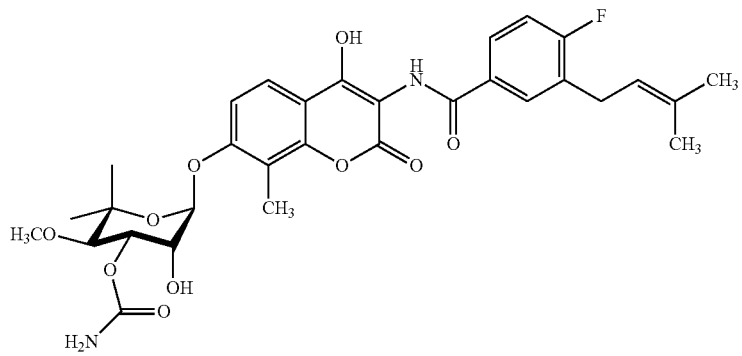

fbn

Novenamine hydrochloride (118 mg, 0.26 mmol, 1.0 eq.) and a magnetic stirbar were added to a 25 mL conical flask and sealed with a rubber septum. A vent needle was inserted and the flask was sparged with $N_2$ for 5 minutes (free novenamine begins to oxidize upon exposure to O2!). 2 mL of pyridine were added under positive $N_2$ pressure and the flask was cooled to −40° C. in a dry ice/acetonitrile bath. 4-fluoro-3-prenylbenzoyl chloride (75 mg, 0.31 mmol, 1.2 eq.) was dissolved in 0.5 mL of pyridine and added to the stirring novenamine solution. The solution was stirred for 16 h while allowing the bath to warm to room temperature. The reaction mixture was concentrated by rotary evaporation and then subjected to flash column chromatography with DCM/MeOH. The product was further purified by reversed phase column chromatography with a Zorbax C18 column with acetonitrile/water as the eluent (90% MeCN to 100% MeCN over the course of 15 minutes), 12.7 mg (8% isolated yield after semi-preparative HPLC).

5-hydroxy-3-methoxy-2,2-dimethyltetrahydro-2H-pyran-4-yl carbamate (1-adamantyl novobiocin, "adn"). White solid; TLC Rf=0.4 (5% MeOH/DCM); $^1$H NMR (400 MHz, DMSO-d6) δ 8.21 (s, 1H), 7.70 (d, J=8.8 Hz, 1H), 7.10 (d, J=9.1 Hz, 1H), 6.62 (d, J=61.5 Hz, 2H), 5.58 (s, 1H), 5.50 (d, J=2.4 Hz, 1H), 5.15 (dd, J=9.7, 3.1 Hz, 1H), 4.07 (d, J=3.0 Hz, 1H), 3.49-3.44 (m, 4H), 3.23 (br, 1H), 2.19 (s, 3H), 1.99-1.91 (m, 3H), 1.90-1.84 (m, 6H), 1.69-1.56 (m, 6H), 1.25 (s, 3H), 1.04 (s, 3H); $^{13}$C NMR (101 MHz, DMSO-d6) δ 177.9, 163.1, 160.6, 156.5, 156.3, 150.6, 122.0, 112.5, 111.7, 109.6, 100.9, 98.4, 80.8, 78.0, 70.3, 68.8, 61.0, 40.4, 38.4, 36.1, 28.5, 27.6, 22.7, 8.3; HRMS (ESI Neg) m/z calculated for $C_{30}H_{37}N_2O_{10}$ [M−H]$^-$ 585.2454, found: 585.2471.

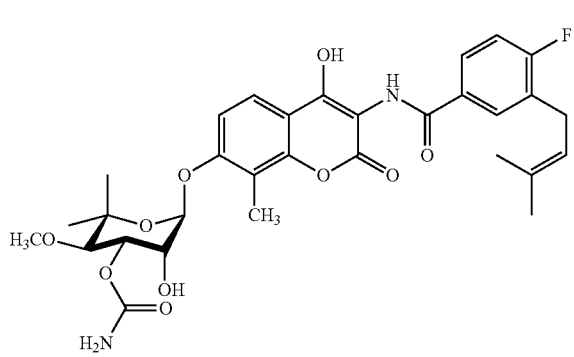

fluorobiocin (fbn)

(3R,4S,5R,6R)-6-((3-(4-fluoro-3-(3-methylbut-2-en-1-yl)benzamido)-4-hydroxy-8-methyl-2-oxo-2H-chromen-7-yl)oxy)-5-hydroxy-3-methoxy-2,2-dimethyltetrahydro-2H-pyran-4-yl carbamate (fluorobiocin, "fbn"). White solid; TLC Rf=0.5 (10% MeOH/DCM); $^1$H NMR (500 MHz, DMSO-d6) δ 12.5 (br, 1H), 9.3 (s, 1H), 7.9-7.8 (m, 2H), 7.6 (d, J=8.8 Hz, 1H), 7.2 (t, J=9.1 Hz, 1H), 7.1 (d, J=8.9 Hz, 1H), 6.8-6.5 (m, 2H), 5.6 (d, J=5.2 Hz, 1H), 5.5 (d, J=2.5 Hz, 1H), 5.3 (t, J=7.5 Hz, 1H), 5.2 (dd, J=9.9, 3.1 Hz, 1H), 4.1-4.0 (m, 1H), 3.5-3.5 (m, 4H), 3.3 (d, J=7.5 Hz, 2H), 2.2 (s, 3H), 1.7-1.7 (m, 6H), 1.3 (s, 3H), 1.1 (s, 3H); $^{13}$C NMR (126 MHz, DMSO-d6) δ 165.4, 162.1 (d, J=248.8 Hz), 161.8 (br), 160.8, 156.7, 156.3, 150.9, 132.8, 130.5 (d, J=5.8 Hz), 130.3 (d, J=2.5 Hz), 127.9 (d, J=8.8 Hz), 127.7 (d, J=16.9 Hz), 121.9, 121.2, 114.8 (d, J=22.8 Hz), 112.5, 111.0, 109.5, 100.1, 98.5, 80.7, 78.0, 70.3, 68.8, 61.0, 28.5, 27.0, 25.5, 22.7, 17.6, 8.3; $^{19}$F NMR (471 MHz, DMSO-d6) δ −114.6; HRMS (ESI Neg) m/z calculated for $C_{31}H_{34}FN_2O_{10}$ [M-H]$^-$ 613.2197, found: 613.2199.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of treating an individual having a bacterial infection caused by a Gram-negative bacterium, the method comprising administering to the individual a single pharmaceutical composition comprising both an aminocoumarin compound or a salt thereof and a polymyxin compound or a salt thereof;
wherein the polymyxin compound is polymyxin B or a salt thereof; and
wherein the Gram-negative bacterium is *Klebsiella pneumoniae, Acinetobacter baumannii, Pseudomonas aeruginosa, Escherichia coli,* or an *Enterobacter* spp.

2. The method of claim 1, wherein the aminocoumarin compound or salt thereof binds a Lpt protein in the Gram-negative bacterium.

3. The method of claim 2, wherein the Lpt protein is LptB.

4. The method of claim 1, wherein the aminocoumarin compound is a novobiocin analog, or a salt thereof.

5. The method of claim 4, wherein the novobiocin analog is descarbamyl novobiocin or a salt thereof, novobiocin-adamantyl or a salt thereof, or novobiocin-aglycone or a salt thereof.

6. The method of claim 1, wherein the aminocoumarin compound is clorobiocin, a clorobiocin analog, or a salt thereof.

7. The monotherapy method of claim 1, wherein the aminocoumarin compound is coumermycin A1, a coumermycin A1 analog, or a salt thereof.

8. The method of claim 1, wherein the pharmaceutical composition further comprises a pharmaceutically acceptable excipient.

9. The method of claim 1, wherein the pharmaceutical composition is in unit-dose form.

10. The method of claim 1, wherein the pharmaceutical composition is formulated for parenteral administration, intranasal administration, topical administration, or oral administration.

11. The method of claim 1, wherein the pharmaceutical composition is formulated for intramuscular administration, intravenous administration, intrathecal administration, or ophthalmic administration.

12. The method of claim 1, wherein the bacterial infection is a urinary tract infection, meningeal infection, eye infection, lung infection, or bacteremia.

13. The method of claim 1, wherein the Gram-negative bacterium is a non-opportunistic pathogen.

14. The method of claim 1, wherein the method is effective at substantially reducing or eliminating the bacterial infection.

15. The method of claim 1, wherein the aminocoumarin compound is novobiocin, or a salt thereof.

16. The method of claim 1, wherein the Gram-negative bacterium is a polymyxin-resistant bacterium.

17. The method of claim 1, wherein the Gram-negative bacterium is a novobiocin-resistant bacterium.

18. The method of claim 1, wherein the Gram-negative bacterium is a novobiocin- and polymyxin-resistant bacterium.

* * * * *

UNITED STATES PATENT AND TRADEMARK OFFICE
CERTIFICATE OF CORRECTION

PATENT NO. : 11,191,773 B2
APPLICATION NO. : 16/631717
DATED : December 7, 2021
INVENTOR(S) : Daniel E. Kahne et al.

Page 1 of 1

It is certified that error appears in the above-identified patent and that said Letters Patent is hereby corrected as shown below:

In the Specification

At Column 1, under Statement as to Federally Funded Research:
"This invention was made with government support under AI109764 awarded by the National Institutes of Health, and DGE-1144152 awarded by the National Science Foundation. The government has certain rights in the invention."

Should read:
-- This invention was made with government support under AI109764 and GM100951 awarded by the National Institutes of Health, and DGE-1144152 awarded by the National Science Foundation. The government has certain rights in the invention --

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: Synthetic Construct

<400> SEQUENCE: 1
ggcaaactgt ataccgaaag tgcgattacg gtaatgcatg cctgcggcc         49

<210> SEQ ID NO 2
<211> LENGTH: 49
<212> TYPE: DNA
<213> ORGANISM: Artificial Sequence
<220> FEATURE:
<223> OTHER INFORMATION: Synthetic Construct

<400> SEQUENCE: 2
ggccgcaggc atgcattacc gtaatcgcac tttcggtata cagtttgcc         49

<210> SEQ ID NO 3
<211> LENGTH: 47
<212> TYPE: DNA
<213> ORGANISM: Artificial Sequence
<220> FEATURE:
<223> OTHER INFORMATION: Synthetic Construct

<400> SEQUENCE: 3
gggatgctgg cgcagcgcag cgcgctggtg gtgatgcagg cttctgg           47

<210> SEQ ID NO 4
<211> LENGTH: 47
<212> TYPE: DNA
<213> ORGANISM: Artificial Sequence
<220> FEATURE:
<223> OTHER INFORMATION: Synthetic Construct

<400> SEQUENCE: 4
```

```
ccagaagcct gcatcaccac cagcgcgctg cgctgcgcca gcatccc                    47

<210> SEQ ID NO 5
<211> LENGTH: 51
<212> TYPE: DNA
<213> ORGANISM: Artificial Sequence
<220> FEATURE:
<223> OTHER INFORMATION: Synthetic Construct

<400> SEQUENCE: 5
ctgccacagg aagcctccat tttcagccgc ctcagcgttt acgataacct g               51

<210> SEQ ID NO 6
<211> LENGTH: 51
<212> TYPE: DNA
<213> ORGANISM: Artificial Sequence
<220> FEATURE:
<223> OTHER INFORMATION: Synthetic Construct

<400> SEQUENCE: 6
caggttatcg taaacgctga ggcggctgaa aatggaggct tcctgtggca g               51
```